US010981974B2

(12) United States Patent
Pettit et al.

(10) Patent No.: US 10,981,974 B2
(45) Date of Patent: Apr. 20, 2021

(54) CELL CULTURE MEDIA CONTAINING COMBINATIONS OF PROTEINS

(71) Applicant: Ventria Bioscience Inc., Junction City, KS (US)

(72) Inventors: Steven Clyde Pettit, Junction City, KS (US); Mary Ann Michelle Fernandez Santos, Junction City, KS (US); Ning Huang, Junction City, KS (US)

(73) Assignee: Ventria Bioscience Inc., Junction City, KS (US)

( * ) Notice: Subject to any disclaimer, the term of this patent is extended or adjusted under 35 U.S.C. 154(b) by 0 days.

(21) Appl. No.: 16/847,337

(22) Filed: Apr. 13, 2020

(65) Prior Publication Data

US 2020/0247871 A1    Aug. 6, 2020

Related U.S. Application Data

(63) Continuation of application No. 15/188,478, filed on Jun. 21, 2016, now Pat. No. 10,618,951, which is a continuation of application No. 12/708,462, filed on Feb. 18, 2010, now abandoned.

(60) Provisional application No. 61/154,204, filed on Feb. 20, 2009.

(51) Int. Cl.
*C07K 14/76* (2006.01)
*C07K 14/79* (2006.01)
*C12N 5/00* (2006.01)

(52) U.S. Cl.
CPC ............. *C07K 14/76* (2013.01); *C07K 14/79* (2013.01); *C12N 5/0043* (2013.01); *C12N 5/0056* (2013.01); *C12N 2500/24* (2013.01); *C12N 2500/25* (2013.01); *C12N 2501/105* (2013.01); *C12N 2501/998* (2013.01); *C12N 2510/02* (2013.01)

(58) Field of Classification Search
None
See application file for complete search history.

(56) References Cited

U.S. PATENT DOCUMENTS

| | | |
|---|---|---|
| 4,075,197 A | 2/1978 | Schuck |
| 4,093,612 A | 2/1978 | Travis |
| 4,086,222 A | 4/1978 | Lindquist |
| 4,097,473 A | 6/1978 | Lewis |
| 4,136,094 A | 1/1979 | Condie |
| 4,228,154 A | 10/1980 | Fisher |
| 5,250,662 A | 10/1993 | Chang |
| 5,656,729 A | 8/1997 | Fuluhata |
| 5,677,424 A | 10/1997 | Rucheton |
| 5,710,253 A | 1/1998 | Ohtani |
| 5,728,553 A | 3/1998 | Goodey |
| 5,780,593 A | 7/1998 | Lihme |
| 5,780,594 A | 7/1998 | Carter |
| 5,914,022 A | 6/1999 | Lowry |
| 5,917,022 A | 6/1999 | Davies |
| 5,985,289 A | 11/1999 | Potter et al. |
| 5,994,507 A | 11/1999 | Pilotii |
| 6,001,974 A | 12/1999 | Demmer |
| 6,034,221 A | 3/2000 | Berezenko et al. |
| 6,406,909 B1 | 6/2002 | Shibuya |
| 6,586,206 B1 | 7/2003 | Dixit |
| 6,617,133 B1 | 9/2003 | Noda |
| 6,617,161 B2 | 9/2003 | Luyten |
| 6,638,740 B1 | 10/2003 | Goodey |
| 6,733,746 B2 | 5/2004 | Daley |
| 6,787,636 B1 | 9/2004 | Carter |
| 6,991,824 B2 | 1/2006 | Huang |
| 7,138,150 B2 | 11/2006 | Huang |
| 7,223,561 B2 | 5/2007 | Goodey |
| 7,304,208 B2 | 12/2007 | Huang |
| 7,351,801 B2 | 4/2008 | Belew |
| 7,354,902 B2 | 4/2008 | Legrand |
| 7,417,178 B2 | 8/2008 | Huang |
| 7,423,124 B2 | 9/2008 | Belew |
| 7,531,327 B2 | 5/2009 | Goldenberg |
| 7,531,631 B2 | 5/2009 | Shibata |
| 7,537,930 B2 | 5/2009 | Goldenberg |
| 7,585,955 B2 | 9/2009 | Sang |
| 2002/0076747 A1 | 6/2002 | Price |
| 2003/0177537 A1 | 9/2003 | Moloney |
| 2003/0221223 A1 | 11/2003 | Huang |
| 2004/0063617 A1 | 4/2004 | Huang |
| 2004/0111766 A1 | 6/2004 | Huang |
| 2005/0050602 A1 | 3/2005 | Altosaar |
| 2007/0078851 A1 | 4/2007 | Grell |
| 2007/0289033 A1 | 12/2007 | Yang |

(Continued)

FOREIGN PATENT DOCUMENTS

| | | |
|---|---|---|
| EP | 0947581 | 7/2004 |
| WO | 9836085 | 8/1998 |

(Continued)

OTHER PUBLICATIONS

Kwon, Secretory Production of hGM-CSF with a high specific biological activity by transgenic plant cell suspension culture, 2003, Biotech Bioprocess. Eng. 8 135-141.

Suzuki, Expression, Characterization, and Biologic Activity of Recombitant Human Lactoferrin in Rice, 2003, J. Ped. Gast. Nutr. 36 190-199.

Zhang, Expression and production of bioactive human interleukin-18 in transgenic tobacco plants, 2003, Biotechnology Lett. 25 1629-1635.

Newman, Serum-free cell culture—the ethical, scientific, and economic choice, 2003, Biomed. Sci. 941-942.

(Continued)

*Primary Examiner* — Paul J Holland
(74) *Attorney, Agent, or Firm* — Hovey Williams LLP

(57) ABSTRACT

The present invention relates to cell culture media supplemented with a plant-produced recombinant mammalian albumin supplement, as well as methods of making the cell culture media, and methods of using the supplemented cell culture media to improve growth characteristics of cultured cells.

26 Claims, 20 Drawing Sheets

Specification includes a Sequence Listing.

(56) References Cited

U.S. PATENT DOCUMENTS

| | | | |
|---|---|---|---|
| 2008/0318277 | A1 | 12/2008 | Huang |
| 2009/0170165 | A1 | 7/2009 | Lee |
| 2009/0181426 | A1 | 7/2009 | Dileo |
| 2009/0258004 | A1 | 10/2009 | Huang |
| 2010/0015713 | A1 | 1/2010 | Deeter |
| 2011/0189751 | A1 | 8/2011 | Barnett |
| 2013/0157356 | A1 | 6/2013 | Barnett |

FOREIGN PATENT DOCUMENTS

| | | |
|---|---|---|
| WO | 1998050543 | 11/1998 |
| WO | 200003012 | 1/2000 |
| WO | 0172959 | 10/2001 |
| WO | 02099067 | 12/2002 |
| WO | 2005001094 | 1/2005 |
| WO | 05011367 | 2/2005 |
| WO | 2005056578 | 6/2005 |
| WO | 2007002762 | 1/2007 |

OTHER PUBLICATIONS

Conley, Derivation, propagation, and differentiation of human embryonic stem cells, 2004, Int. J. Biochem. Cell. Biol. 36(4) 555-67.
Panahi, Recombinant protein expression plasmids optimized for industrial *E. coli* fermentation and plant systems produce biologically active human insulin-like growth factor-1 in transgenic rice and tobacco plants, 2004, Transgenic Res. 13 245-259.
Tidwell, Administration of Hsp70 in vivo inhibits motor and sensory neuron degeneration, 2004, Cell Stress & Chap. 9 (1) 88-90.
Wirth, Expression of active human epidermal growth factor (hEGF) in tobacco plants by integrative and non-integrative systems, 2004, Mol. Breeding 13 23-35.
Baker, Lactoferrin and Iron: structural and dynamic aspects of binding and release, 2004, Biometals 17 209-216.
Sugita, Genetically modified rice seeds accumulating GLP-1 analogue stimulate insulin secretion from a mouse pancreatic beta-cell line, 2005, Febs Lett 579 1085-1088.
Marillonnet, Systemic Agrobacterium tumefaciens-mediated transfection of viral replicons for efficient transient expression in plants, Nature Biotech 23(6) 718-723, 2005.
Huang, Production of human serum albumin by sugar starvation induced promoter and rice cell culture, 2005, Transgenic Res. 14 569-581.
Novoselova, Treatment with extracellular HSP70/HSC70 protein can reduce polyglutamine toxicity and aggregation, 2005, Neurochem 94 597-606.
Keenan, Evaluation of recombinant human transferrin (DeltaFerrin) as an iron chelator in serum-free media for mammalian cell culture, 2006, Cytotechnology 51 29-37.
Invitria, Ventria Bioscience announces third bioprocessing product: cellastim, animal-free recombinant human serum albumin, Press release Jul. 13, 2006.
Wally, A structural comparison of human serum transferrin and human lactoferrin, Biometals 20 249-262, 2007.
Shaner, All in the family:atypical Hsp70 chaperones are conserved modulators of Hsp70 activity, 2007, Cell Stress Chap. 12(1) 1-8.
Wandinger, The Hsp90 Chaperone Machinery, J. Biol. Chem. 283 (27) 18473-18477, 2008.
Brocchieri, Hsp70 genes in the human genome: conservation and differentiation patterns predict a wide array of overlapping and specialized functions, 2008, BMC Evol. Biol. 819 1-20.
Invitria, Zap-CHO Media Supplement Optimizes the Growth kinetics and productivity of CHO cells, Poster, Summer 2008.
Invitria, InVitria's Cellastim delivers superior results in mammalian cell culture, Press release Sep. 25, 2008.
Invitria, InVitria's Cellastim showcased in Nature article, Press release—Oct. 7, 2008.
Ying, The ground state of embryonic stem cell self-renewal, 2008, Nature 453 519-524.
Wong, Lactoferrin is a survival factor for neutrophils in rheumatoid synovial fluid, 2009, Rheumatology 48 39-44.
Blindauer, Structure, properties, and engineering of the major zinc blinding site on human albumin, 2009, J. Biol. Chem. 281(34) 23116-24.
Sarkar, Rice sHsp genes: genomic organization and expression profiling under stress and development, 2009, BMC Genomics 10 393 1-18.
Kampinga, Guidelines for the nomenclature of the human heat shock proteins, 2009, Cell. Stress Chap. 14 105-111.
Petitt, Enhanced growth and productivity of a hybridoma with recombinant human albumin and lactoferrin, 2009, Bioprocess J. 8(1) 50-55.
Invitria, Recombinant Human Serum Albumin Expressed in Plants Improves the Productivity and Growth Kinetics of CHO, Press release, Mar. 2009.
Mantei, et al, 1981, Nature 293 620-625.
Hashizume, 1987, Meth. Enzmol. 147 303-314.
Huang, 2008, In Vitro Cell Dev. Biol. 44 464-471.
Invitria, Press release—Sep. 2009.
Invitria, Press release—Oct. 2009.
Tang, 2010, Wound Rep. Reg. 18 123-131.
Invitria, Poster Jan. 2010.
Office Action in corresponding U.S. Appl. No. 12/708,462, dated Feb. 19, 2013.
Office Action in corresponding U.S. Appl. No. 12/708,462, dated Sep. 18, 2013.
Office Action in corresponding U.S. Appl. No. 12/708,462, dated Jun. 3, 2015.
Office Action in corresponding U.S. Appl. No. 12/708,462, dated Dec. 21, 2015.
Office Action in corresponding U.S. Appl. No. 15/188,478, dated Oct. 16, 2018.
Mawal, 1987, Bioscience Reports, vol. 7, issue 1.
Final Office Action in corresponding U.S. Appl. No. 15/188,478, dated Jun. 17, 2019.
Okabayshi et al, J. Biochem, Japanese Biochem Soc., 110 (1), 103-110, 1991.
Ravagnan, Nature Cell Biol., 2001, 3, 839-843, 2001.
Wartmann et al., FEMS yeast Res 3 (2), 223-232, 2003.
Millan, A chloroplast transgenic approach to hyper-express and purify Human Serum Albumin, a protein highly susceptible to proteolytic degradation, Plant Biotech. J. 1 71-79, 2003.
Daniell, et al., Vaccine, 23 (15), 1779-1783, 2005.
Ying, et al., Nature, 453, 519-524, 2008.
Barnes, Serum-free Cell Culture: a Unifying Approach, Cell, 1980, vol. 22, 649-655.
Gething, Cell-surface expression of influenza haemagglutinin from a cloned DNA copy of the RNA gene, 1981, Nature 293 620-625.
Welch, Purification of the Major Mammalian Heat Shock Proteins, 1982, J. Biol. Chem. 257 (24) 14949-14959.
Murakami, Growth of hybridoma cells in serum-free medium: Ethanolamine is an essential component, 1982, PNAS 79 1158-1162.
Hashizume, et al, Identification of Lactoferrin as an essential growth factor for human lymphocytic cell lines in serum-free medium, 1983, Biochem. Biophys. Acta. 763 377-382.
Kovar, Serum-free medium for hybridoma and parental myeloma cell cultivation: a novel composition of growth-supporting substances, 1984, Immunol. Lett. 7 339-345.
Amouric, Effect of Lactoferring on the growth of a human colon adenocarcinoma cell line—comparison with transferrin, In vitro 20 (7) 543-548, 1984.
Cole, Antibody production by human x human hybridomas in serum-free medium, J. Imm. Meth. 78 271-278, 1985.
Welch, Rapid Purification of Mammalian 70,000-Dalton stress proteins: Affinity of the proteins for nucleotides, Mal. Cell. Biol. 5(6) 1229-1237, 1985.
Kovar, Serum-free medium for hybridoma and parental myeloma cell cultivation, Methods Enz. 121 277-292, 1986.
Brower, Growth of cell lines and clinical specimens of human non-small cell lung cancer in a serum-free defined medium, Cancer Res. 46 798-806, 1986.

(56) References Cited

OTHER PUBLICATIONS

Mizrahi, Biologicals produced from animal cells in culture—an overview, Biotechnology Adv. 6(2) 207-220, 1988.

Mizrahi, Media for cultivation of animal cells—an overview, Cytotechnology 1 199-214, 1988.

Butler, Nutritional aspects of the growth of animal cells in culture, J. Biotechnol. 12 97-110, 1989.

Anderson, Structure of Human Lactoferrin: Crystallographic Structure Analysis and Refinement at 2-8 A resolution, J. Mal. Biol. 209 711-734, 1989.

Sijmons, Production of correctly processed human serum albumin in transgenic plants, Biotechnology (NY) 8 217-221, 1990.

Yamada, Stimulation of proliferation and immunoglobulin M production by lactoferrin in human-human and mouse-mouse hybridomas cultures in serum-free conditions, Cytotechnology 3 123-131, 1990.

Lang, Optimization of Growth and secretion of human monoclonal antibodies by hybridomas cultured in serum-free media, Hybridoma 10 (3) 401-408, 1991.

Butler, Nutritional aspects of the growth of animal cells in culture, Mammalian cell Biotechnology, 1991.

Litwin, The growth of Vero cells in suspension as cell-aggregates in serum-free media, Cytotechnology 10(2) 169-74, 1992.

Johnson, Exogenous HSP70 Becomes cell associated, but not internalized, by stressed arterial smooth muscle cells, In vitro Dev. Biol. 29A 807-812, 1993.

Chua, Enhanced IgG production in eRDF media with and without serum, J. Imm. Meth. 167 109-119, 1994.

Carter, Structure of serum albumin, Adv. Pro!. Chem. 45 153-203, 1994.

Matsumoto, Characterization of a human glycopreotein (erythropoietin) produced in cultured tobacco cells, Plant Mol. Biol. 27 1163-1172, 1995.

Kwon, Expression of Active Human Interleikin-6 in Transgenic Tobacco, Mol. Cells 5 (5) 486-492, 1995.

Vianes, Development of an Efficient Serum-Free Semisolid Culture System for the Evaluation of HEmatopoietic Progenitors, J. Hematotherapy 4 105-111.

Hounenou, Exogenous heat shock cognate Hsc70 prevents axotomy-induced death of spinal sensory neurons, Cell Stress & Chap 1 (3) 161-166, 1996.

Bi, Effect of Lactoferring on Proliferation and Differentiation of the Jurkat Human Lymphoblastic T Cell Line, 1997, Arch. Immunol. Ther. Exp.45(4) 315-20.

Guzhova, Effects of exogenous stress protein 70 on the functional properties of human promonocytes through binding to cell surface and internalization, Cell Stress & Chap. 3 (1) 67-77, 1998.

Bai, Multi-metal binding site of serum albumin, J. Inorg. Biochem. 70 (1) 33-39, 1998.

Arakawa, Improvements in human health through production of human milk proteins in transgenic food plants, 1999, Adv. Exp. Med. Biol. 464 149-159.

Wiles, Embryonic Stem Cell Development in a Chemically Defined Medium, 1999, Exp. Cell. Res. 247(1) 241-8.

James, Production and Characterization of Biologically Active Human GM-CSF Secreted by Genetically Modified Plant Cells, Prat. Express. Pur. 19 131-138, 2000.

Leite, Expression of correctly processed human growth hormone in seeds of transgenic plants, 2000, Mol. Breeding 6 47-53.

Chadd, Therapeutic antibody expression technology, Curr. Opin. Biotechnol. 12(2) 188-194, 2001.

Zeilinger, Three-dimensional Co-culture of Primary Human Liver Cells in Bioreactors for In Vitro Drug Studies: Effects of the Initial Cell Quality on the Long-Term Maintenance of Hepatocyte-specific Functions, 2002, Altern. Lab. Anim. 30(5) 525-38.

Blake, Protein Supplementation of Human IVF Culture Media, 2002, J. Assisi. Reprod. Genet. 19(3) 137-143.

Bungum, Recombitant human albumin as protein source in culture media used for IVF: a prospective randomized study, 2002, Reprod. Biomed. Online 4(3) 233-6.

Chuang, Pharmaceutical Strategies Utilizing Recombitant Human Serum Albumin, Pharm Res 19(5) 569-577, 2002.

Huang, Expression of functional recombinant human lysozyme in transgenic rice cell culture, Transgenic Res. 11(3) 229-39, 2002.

Lonnerdal, Expression of Human Milk Proteins in Plants, 2002, J. Am. Coll. Nutr. 21(3) 218S-221S.

Farran, Targeted Expression of human serum albumin to potato tubers, 2002, Transgenic Res. 11(3) 229-39.

Sardana, Biological activity of human granulocyte-macrophage colony stimulating factor is maintained in a fusion with seed glutelin peptide, 2002, Transgenic Res. 11 521-531.

Balaban, Embryo culture as a diagnostic tool, 2003, Reprod. Biomed. Online 7(6) 671-682.

```
               1730       1740       1750       1760       1770       1780       1790       1800
native lac  TGC CTC GAT GGC AAA CGG AAG CCT GTG ACT GAG GCT AGA AGC TGC CAT CTT GCC ATG GCC CCG AAT CAT GCC GTG
             C   L   D   G   K   R   K   P   V   T   E   A   R   S   C   H   L   A   M   A   P   N   H   A   V
               1730       1740       1750       1760       1770       1780       1790       1800
cod opt lac TGC CTC GAC GGC AAG CGC AAG CCC GTC ACC GAG GCG CGG TCC TGC CAC CTG GCG ATG GCC CCC AAC CAC GCC GTC
            ||| ||| ||  ||| ||  ||| ||  ||  ||  ||  ||| ||   ||  ||  ||| ||| ||   || ||| ||| ||   || ||| ||| |||
native lac  TGC CTC GAT GGC AAA CGG AAG CCT GTG ACT GAG GCT AGA AGC TGC CAT CTT GCC ATG GCC CCG AAT CAT GCC GTG
                      1810       1820       1830       1840       1850       1860       1870
native lac  GTG TCT CGG ATG GAT AAG GTG GAA CGC CTG AAA CAG GTG TTG CTC CAC CAA CAG GCT AAA TTT GGG AGA AAT GGA
             V   S   R   M   D   K   V   E   R   L   K   Q   V   L   L   H   Q   Q   A   K   F   G   R   N   G
                      1810       1820       1830       1840       1850       1860       1870
cod opt lac GTC TCC CGC ATG GAC AAG GTC GAG CGC CTC AAG CAG GTG CTC CTG CAC CAG CAG GCC AAG TTC GGC CGG AAC GGC
            ||  ||  ||  ||| ||  ||| ||  ||  ||| ||  ||  ||| ||| ||  ||  ||| ||   || ||  ||  ||| ||  ||   || |||
native lac  GTG TCT CGG ATG GAT AAG GTG GAA CGC CTC AAA CAG GTG TTG CTC CAC CAA CAG GCT AAA TTT GGG AGA AAT GGA
               1880       1890       1900       1910       1920       1930       1940       1950
native lac  TCT GAC TGC CCG GAC AAG TTT TGC TTA TTC CAG TCT GAA ACC AAA AAC CTT CTG TTC AAT GAC AAC ACT GAG TGT
             S   D   C   P   D   K   F   C   L   F   Q   S   E   T   K   N   L   L   F   N   D   N   T   E   C
               1880       1890       1900       1910       1920       1930       1940       1950
cod opt lac AGC GAC TGC CCG GAC AAG TTC TGC CTG TTC CAG AGC GAG ACC AAG AAC CTC CTC TTC AAC GAC AAC ACC GAG TGC
            ||| ||| ||| ||| ||| ||| ||  ||| ||  ||| ||| ||  ||| ||| ||  ||| ||  ||  ||| ||  ||| ||| ||  ||| |||
native lac  TCT GAC TGC CCG GAC AAG TTT TGC TTA TTC CAG TCT GAA ACC AAA AAC CTT CTG TTC AAT GAC AAC ACT GAG TGT
               1960       1970       1980       1990       2000       2010       2020
native lac  CTG GCC AGA CTC CAT GGC AAA ACA ACA TAT GAA AAA TAT TTG GGA CCA CAG TAT GTC GCA GGC ATT ACT AAT CTG
             L   A   R   L   H   G   K   T   T   Y   E   K   Y   L   G   P   Q   Y   V   A   G   I   T   N   L
               1960       1970       1980       1990       2000       2010       2020
cod opt lac CTG GCG CGC CTC CAC GGC AAG ACC ACC TAC GAG AAG TAC CTG GGC CCG CAG TAC GTC GCC GGC ATC ACC AAC CTC
            ||| ||   |  ||| ||  ||| ||  ||  ||  ||  ||| ||  ||  ||  ||   || ||| ||  ||| ||| ||| ||  ||  ||  |||
native lac  CTG GCC AGA CTC CAT GGC AAA ACA ACA TAT GAA AAA TAT TTG GGA CCA CAG TAT GTC GCA GGC ATT ACT AAT CTG
               2030       2040       2050       2060       2070
native lac  AAA AAG TGC TCA ACC TCC CCC CTC CTG GAA GCC TGT GAA TTC CTC AGG AAG TAA      (SEQ ID NO: 8)
             K   K   C   S   T   S   P   L   L   E   A   C   E   F   L   R   K   *           (SEQ ID NO: 10)
               2030       2040       2050       2060       2070
cod opt lac AAG AAG TGC TCC ACC TCC CCC CTC CTG GAG GCG TGC GAG TTC CTC CGC AAG TGA      (SEQ ID NO: 9)
            ||| ||| ||| ||  ||| ||| ||| ||| ||| ||  ||  ||  ||  ||| ||| |   ||| ||       (SEQ ID NO: 8)
native lac  AAA AAG TGC TCA ACC TCC CCC CTC CTG GAA GCC TGT GAA TTC CTC AGG AAG TAA
```

2079 = Total number of nucleotides

467 = Number of nucleotides changed

693 = Total Number of codons

413 = Number of codons changed

FIG 5A

```
            10             20             30             40
ATG GCA TCC ATA AAT CGC CCC ATA GTT TTC TTC ACA GTT TGC TTG
 M   A   S   I   N   R   P   I   V   F   F   T   V   C   L>
___a___a___a___a___a___a__GT1 SP___a___a___a___a___a___a___>

50             60             70             80             90
TTC CTC TTG TGC GAT GGC TCC CTA GCC GAC GCC CAC AAG AGC GAG
 F   L   L   C   D   G   S   L   A>
___a___a___a__GT1 SP___a___a___a___>
                                         D   A   H   K   S   E>
                                        ___OPTIMIZED HSA _b___>

100            110            120            130
GTG GCC CAC CGC TTC AAG GAC CTC GGC GAG GAG AAC TTC AAG GCC
 V   A   H   R   F   K   D   L   G   E   E   N   F   K   A>
___b___b___b___b___b__OPTIMIZED HSA ___b___b___b___b___b___>

140            150            160            170            180
CTC GTG CTC ATC GCC TTC GCC CAG TAC CTC CAG CAG TGC CCG TTC
 L   V   L   I   A   F   A   Q   Y   L   Q   Q   C   P   F>
___b___b___b___b___b__OPTIMIZED HSA ___b___b___b___b___b___>

190            200            210            220
GAG GAC CAC GTG AAG CTC GTG AAC GAG GTG ACC GAG TTC GCC AAG
 E   D   H   V   K   L   V   N   E   V   T   E   F   A   K>
___b___b___b___b___b__OPTIMIZED HSA ___b___b___b___b___b___>

230            240            250            260            270
ACC TGC GTG GCC GAC GAG AGC GCC GAG AAC TGC GAC AAG AGC CTC
 T   C   V   A   D   E   S   A   E   N   C   D   K   S   L>
___b___b___b___b___b__OPTIMIZED HSA ___b___b___b___b___b___>

280            290            300            310
CAC ACC CTC TTC GGC GAC AAG CTC TGC ACC GTG GCC ACC CTC CGC
 H   T   L   F   G   D   K   L   C   T   V   A   T   L   R>
___b___b___b___b___b__OPTIMIZED HSA ___b___b___b___b___b___>

320            330            340            350            360
GAG ACC TAC GGC GAG ATG GCC GAC TGC TGC GCC AAG CAG GAG CCG
 E   T   Y   G   E   M   A   D   C   C   A   K   Q   E   P>
___b___b___b___b___b__OPTIMIZED HSA ___b___b___b___b___b___>

370            380            390            400
GAG CGC AAC GAG TGC TTC CTC CAG CAC AAG GAC GAC AAC CCG AAC
 E   R   N   E   C   F   L   Q   H   K   D   D   N   P   N>
___b___b___b___b___b__OPTIMIZED HSA ___b___b___b___b___b___>

410            420            430            440            450
CTC CCG CGC CTC GTG CGC CCG GAG GTG GAC GTG ATG TGC ACC GCC
 L   P   R   L   V   R   P   E   V   D   V   M   C   T   A>
___b___b___b___b___b__OPTIMIZED HSA ___b___b___b___b___b___>
```

FIG 5B

```
          460           470           480           490
TTC CAC GAC AAC GAG GAG ACC TTC CTC AAG AAG TAC CTC TAC GAG
 F   H   D   N   E   E   T   F   L   K   K   Y   L   Y   E>
___b___b___b___b___b__OPTIMIZED HSA  ___b___b___b___b___b___>

500           510           520           530           540
ATC GCC CGC CGC CAC CCG TAC TTC TAC GCC CCG GAG CTC CTC TTC
 I   A   R   R   H   P   Y   F   Y   A   P   E   L   L   F>
___b___b___b___b___b__OPTIMIZED HSA  ___b___b___b___b___b___>

550           560           570           580
TTC GCC AAG CGC TAC AAG GCC GCC TTC ACC GAG TGC TGC CAG GCC
 F   A   K   R   Y   K   A   A   F   T   E   C   C   Q   A>
___b___b___b___b___b__OPTIMIZED HSA  ___b___b___b___b___b___>

590           600           610           620           630
GCC GAC AAG GCC GCC TGC CTC CTC CCG AAG CTC GAC GAG CTC CGC
 A   D   K   A   A   C   L   L   P   K   L   D   E   L   R>
___b___b___b___b___b__OPTIMIZED HSA  ___b___b___b___b___b___>

640           650           660           670
GAC GAG GGC AAG GCC TCC AGC GCC AAG CAG CGC CTC AAG TGC GCC
 D   E   G   K   A   S   S   A   K   Q   R   L   K   C   A>
___b___b___b___b___b__OPTIMIZED HSA  ___b___b___b___b___b___>

680           690           700           710           720
AGC CTC CAG AAG TTC GGC GAG CGC GCC TTC AAG GCC TGG GCC GTG
 S   L   Q   K   F   G   E   R   A   F   K   A   W   A   V>
___b___b___b___b___b__OPTIMIZED HSA  ___b___b___b___b___b___>

730           740           750           760
GCC CGC CTC AGC CAG CGC TTC CCG AAG GCC GAG TTC GCC GAG GTG
 A   R   L   S   Q   R   F   P   K   A   E   F   A   E   V>
___b___b___b___b___b__OPTIMIZED HSA  ___b___b___b___b___b___>

770           780           790           800           810
TCC AAG CTC GTG ACC GAC CTC ACC AAG GTG CAC ACC GAG TGC TGC
 S   K   L   V   T   D   L   T   K   V   H   T   E   C   C>
___b___b___b___b___b__OPTIMIZED HSA  ___b___b___b___b___b___>

820           830           840           850
CAC GGC GAC CTC CTG GAG TGC GCC GAC GAC CGC GCC GAC CTC GCC
 H   G   D   L   L   E   C   A   D   D   R   A   D   L   A>
___b___b___b___b___b__OPTIMIZED HSA  ___b___b___b___b___b___>

860           870           880           890           900
AAG TAC ATC TGC GAG AAC CAG GAC AGC ATC TCC AGC AAG CTC AAG
 K   Y   I   C   E   N   Q   D   S   I   S   S   K   L   K>
___b___b___b___b___b__OPTIMIZED HSA  ___b___b___b___b___b___>

910           920           930           940
GAG TGC TGC GAG AAG CCG CTC CTG GAG AAG TCC CAC TGC ATC GCC
 E   C   C   E   K   P   L   L   E   K   S   H   C   I   A>
___b___b___b___b___b__OPTIMIZED HSA  ___b___b___b___b___b___>
```

FIG 5C

```
          950         960         970         980         990
         GAG GTG GAG AAC GAC GAG ATG CCG GCC GAC CTC CCG TCC CTC GCC
          E   V   E   N   D   E   M   P   A   D   L   P   S   L   A>
         __b___b___b___b___b__OPTIMIZED HSA___b___b___b___b___b__>

1000        1010        1020        1030
         GCC GAC TTC GTG GAG AGC AAG GAC GTG TGC AAG AAC TAC GCC GAG
          A   D   F   V   E   S   K   D   V   C   K   N   Y   A   E>
         __b___b___b___b___b__OPTIMIZED HSA___b___b___b___b___b__>

1040        1050        1060        1070        1080
         GCC AAG GAC GTC TTC CTC GGC ATG TTC CTC TAC GAG TAC GCC CGC
          A   K   D   V   F   L   G   M   F   L   Y   E   Y   A   R>
         __b___b___b___b___b__OPTIMIZED HSA___b___b___b___b___b__>

1090        1100        1110        1120
         CGC CAC CCG GAC TAC TCC GTG GTG CTC CTC CGC CTC GCC AAG
          R   H   P   D   Y   S   V   V   L   L   R   L   A   K>
         __b___b___b___b___b__OPTIMIZED HSA___b___b___b___b___b__>

1130        1140        1150        1160        1170
         ACC TAC GAG ACC ACC CTG GAG AAG TGC TGC GCC GCC GCC GAC CCG
          T   Y   E   T   T   L   E   K   C   C   A   A   A   D   P>
         __b___b___b___b___b__OPTIMIZED HSA___b___b___b___b___b__>

1180        1190        1200        1210
         CAC GAG TGC TAC GCC AAG GTG TTC GAC GAG TTC AAG CCG CTC GTG
          H   E   C   Y   A   K   V   F   D   E   F   K   P   L   V>
         __b___b___b___b___b__OPTIMIZED HSA___b___b___b___b___b__>

1220        1230        1240        1250        1260
         GAG GAG CCG CAG AAC CTC ATC AAG CAG AAC TGC GAG CTC TTC GAG
          E   E   P   Q   N   L   I   K   Q   N   C   E   L   F   E>
         __b___b___b___b___b__OPTIMIZED HSA___b___b___b___b___b__>

1270        1280        1290        1300
         CAG CTC GGC GAG TAC AAG TTC CAG AAC GCC CTC CTC GTG CGC TAC
          Q   L   G   E   Y   K   F   Q   N   A   L   L   V   R   Y>
         __b___b___b___b___b__OPTIMIZED HSA___b___b___b___b___b__>

1310        1320        1330        1340        1350
         ACC AAG AAG GTG CCG CAG GTG TCC ACC CCG ACC CTC GTG GAG GTG
          T   K   K   V   P   Q   V   S   T   P   T   L   V   E   V>
         __b___b___b___b___b__OPTIMIZED HSA___b___b___b___b___b__>

1360        1370        1380        1390
         TCC CGC AAC CTC GGC AAG GTG GGC AGC AAG TGC TGC AAG CAC CCG
          S   R   N   L   G   K   V   G   S   K   C   C   K   H   P>
         __b___b___b___b___b__OPTIMIZED HSA___b___b___b___b___b__>

1400        1410        1420        1430        1440
         GAG GCC AAG CGC ATG CCG TGC GCC GAG GAC TAC CTC TCC GTG GTG
          E   A   K   R   M   P   C   A   E   D   Y   L   S   V   V>
         __b___b___b___b___b__OPTIMIZED HSA___b___b___b___b___b__>
```

FIG 5D

```
         1450        1460        1470        1480
CTC AAC CAG CTC TGC GTG CTC CAC GAG AAG ACC CCG GTG AGC GAC
 L   N   Q   L   C   V   L   H   E   K   T   P   V   S   D>
___b___b___b___b___b__OPTIMIZED HSA ___b___b___b___b___b___>

1490        1500        1510        1520        1530
CGC GTG ACC AAG TGC TGC ACC GAG AGC CTC GTG AAC CGC CGC CCG
 R   V   T   K   C   C   T   E   S   L   V   N   R   R   P>
___b___b___b___b___b__OPTIMIZED HSA ___b___b___b___b___b___>

1540        1550        1560        1570
TGC TTC TCC GCC CTG GAG GTC GAC GAG ACC TAC GTC CCG AAG GAG
 C   F   S   A   L   E   V   D   E   T   Y   V   P   K   E>
___b___b___b___b___b__OPTIMIZED HSA ___b___b___b___b___b___>

1580        1590        1600        1610        1620
TTC AAC GCC GAG ACC TTC ACC TTC CAC GCC GAC ATC TGC ACC CTC
 F   N   A   E   T   F   T   F   H   A   D   I   C   T   L>
___b___b___b___b___b__OPTIMIZED HSA ___b___b___b___b___b___>

1630        1640        1650        1660
TCC GAG AAG GAG CGC CAG ATC AAG AAG CAG ACC GCC CTC GTC GAG
 S   E   K   E   R   Q   I   K   K   Q   T   A   L   V   E>
___b___b___b___b___b__OPTIMIZED HSA ___b___b___b___b___b___>

1670        1680        1690        1700        1710
CTC GTG AAG CAC AAG CCG AAG GCC ACC AAG GAG CAG CTC AAG GCC
 L   V   K   H   K   P   K   A   T   K   E   Q   L   K   A>
___b___b___b___b___b__OPTIMIZED HSA ___b___b___b___b___b___>

1720        1730        1740        1750
GTG ATG GAC GAC TTC GCC GCC TTC GTG GAG AAG TGC TGC AAG GCC
 V   M   D   D   F   A   A   F   V   E   K   C   C   K   A>
___b___b___b___b___b__OPTIMIZED HSA ___b___b___b___b___b___>

1760        1770        1780        1790        1800
GAC GAC AAG GAG ACC TGC TTC GCC GAG GAG GGC AAG AAG CTC GTG
 D   D   K   E   T   C   F   A   E   E   G   K   K   L   V>
___b___b___b___b___b__OPTIMIZED HSA ___b___b___b___b___b___>

1810        1820        1830
GCC GCC AGC CAG GCC GCC CTC GGC CTC TGA    (SEQ ID NO: 11)
 A   A   S   Q   A   A   L   G   L   *>    (SEQ ID NO: 12)
___b___b__OPTIMIZED HSA _b___b___b___>
```

CELL CULTURE MEDIA CONTAINING COMBINATIONS OF PROTEINS

CROSS-REFERENCE TO RELATED APPLICATIONS

This application is a continuation of U.S. Ser. No. 15/188,478, filed Jun. 21, 2016, and issued on Apr. 14, 2020, as U.S. Pat. No. 10,618,951, which is a continuation of U.S. Ser. No. 12/708,462, filed Feb. 18, 2010, now abandoned, which claims the benefit of US provisional patent application No. 61/154,204, filed Feb. 20, 2009, the entire contents of which are incorporated herein by reference.

SEQUENCE LISTING

The following application contains a sequence listing in computer readable format (CRF), submitted as a text file in ASCII format entitled "SequenceListing," created on Apr. 13, 2020, as 44 KB. The content of the CRF is hereby incorporated by reference.

FIELD OF THE INVENTION

The present invention relates to cell culture media containing combinations of proteins, as well as methods of making the cell culture media, and methods of using the cell culture media to improve growth characteristics of cultured cells.

BACKGROUND OF THE INVENTION

Cell culture techniques allow animal or plant cells that are removed from tissues to grow when supplied with the appropriate nutrients and conditions. The cells are capable of dividing and can continue to grow until limited by culture variables such as nutrient depletion or toxic buildup (Butler, M. & Jenkins, H., "Nutritional aspects of growth of animal cells in culture," J of Biotechnol. (1989) 12: 97-110). Cell culture techniques have a number of applications including investigation of the normal physiology or biochemistry of cells (Balaban, B. & Urman, B., "Embryo culture as a diagnostic tool," Reprod. Biomed. Online (2003) 7(6): 671-82), testing the effect of various chemical compounds or drugs on specific cell types (Farkas, D. & Tannenbaum, S. R., "In vitro methods to study chemically-induced hepatotoxicity: a literature review," Curr. Drug Metab. (2005) 6(2): 111-25), studying the sequential or parallel combination of various cell types to generate artificial tissues (Wang et al., "Cartilage tissue engineering with silk scaffolds and human articular chondrocytes," Biomaterials (2006)), and synthesizing valuable biologics from large scale cell cultures (Zeilinger et al., "Three-dimensional co-culture of primary human liver cells in bioreactors for in vitro drug studies: effects of the initial cell quality on the long-term maintenance of hepatocyte-specific functions," Altern. Lab Anim. (2002) 30(5): 525-38). Cell culture techniques have also been used for in vitro fertilization (Blake et al., "Protein supplementation of human IVF culture media," J Assist. Reprod. Genet. (2002) 19(3): 137-43; Bungum et al., "Recombinant human albumin as protein source in culture media used for IVF: a prospective randomized study," Reprod. Biomed. Online (2002) 4(3): 233-6), stem cell research (Conley et al., "Derivation, propagation and differentiation of human embryonic stem cells," Int. J Biochem. Cell Biol. (2004) 36(4): 555-67), vaccine production (Chuang et al., "Pharmaceutical strategies utilizing recombinant human albumin," Pharm. Res. (2002) 19(5): 569-77; GlaxoSmithKline, HAVRIX® (Hepatitis A Vaccine, Inactivated)—Prescribing Information (2005), available at us.gsk.com/products/assets/us_havrix.pdf; Innis et al., "Protection against hepatitis A by an inactivated vaccine," JAMA (1994) 271(17): 1328-34; Merck, PROQUAD®—Measles, Mumps, Rubella, and Varicella (Oka/Merck) Virus Vaccine Live—Prescribing Information (2005), available at www.merck.com/product/usa/pi_circulars/p/proquad/proquad_pi.pdf; Litwin, J., "The growth of Vero cells in suspension as cell-aggregates in serum-free media," Cytotechnology (1992) 10(2): 169-74), tissue engineering including artificial skin (Atala, A., "Future perspectives in reconstructive surgery using tissue engineering," Urol. Clin. North Am. (1999) 26(1): 157-65, ix-x; Sher, et al., "Targeting perlecan in human keratinocytes reveals novel roles for perlecan in epidermal formation," J Biol. Chem. (2006) 281(8): 5178-87) and organs (Neronov et al., "Integrity of endothelium in cryopreserved human cornea," Cryo Letters (2005) 26(2): 131-6; Han, et al., "Interleukin-1 alpha-induced proteolytic activation of metalloproteinase-9 by human skin," Surgery (2005) 138(5): 932-9) and gene and cell therapy (Chadd, H. E. & Chamow, S. M., "Therapeutic antibody expression technology," Curr. Opin. Biotechnol. (2001) 12(2): 188-94).

Biologics encompass a broad range of cell products, and include specific proteins or viruses that require animal cells for propagation. For example, therapeutic proteins such as monoclonal antibodies can be synthesized in large quantities by growing genetically engineered cells in large-scale cultures (Dewar et al., "Industrial implementation of in vitro production of monoclonal antibodies, Ilar J (2005) 46(3): 307-13). The number of such commercially valuable biologics has increased rapidly over the last decade and has led to the present widespread interest in mammalian cell culture technology (Mizrahi, A., "Biologicals produced from animal cells in culture—an overview," Biotechnol. Adv. (1988) 6(2): 207-20).

The major advantage of using cell culture for any of the above applications is the consistency and reproducibility of results that can be obtained from using a batch of clonal cells. The need for cell culture, especially at large scale, became apparent with the need for viral vaccines. Major epidemics of polio in the 1940s and 1950s promoted efforts to develop an effective vaccine. In 1949, it was shown that poliovirus could be grown in cultures of human cells, which led to considerable interest in the development of large quantities of the polio vaccine using cell culture (Ligon, B. L., "Thomas Huckle Weller M D: Nobel Laureate and research pioneer in poliomyelitis, Varicella-zoster virus, cytomegalovirus, rubella, and other infectious diseases," Semin. Pediatr. Infect. Dis. (2002) 13(1): 55-63). The polio vaccine, produced from de-activated virus, became one of the first commercial products of cultured animal cells (Furesz, J., "Developments in the production and quality control of poliovirus vaccines—Historical perspectives," Biologicals (2006)).

Due to the safety and ethical considerations associated with the use of animal-derived cell culture media components, efforts have been made to provide alternative sources for cell culture media and media components.

Published PCT Appl. No. WO 2007/002762, which was based on U.S. Provisional Appl. No. 60/694,236, filed Jun. 28, 2006, relates to recombinant production of components of cell culture media using plant cells, and cell culture media containing such recombinant proteins. The entire contents of this application are incorporated herein by reference.

SUMMARY OF THE INVENTION

Accordingly, it is an objective of the invention to provide cell culture media or media supplements containing combinations of protein components, which when used in cell culture, result in improved growth and/or productivity of cultured cells.

One embodiment of the invention is a cell culture media including a cell culture media base, and two or more proteins selected from the group consisting of growth factors, lactoferrin, transferrin, albumin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, and alpha-lactalbumin.

Yet another embodiment of the invention is a cell culture media including a cell culture media base, albumin, and at least one additional protein selected from the group consisting of growth factors, lactoferrin, transferrin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, and alpha-lactalbumin.

According to further embodiments, the growth factors that may be provided in the cell culture media are selected from the group consisting of epidermal growth factors, keratinocyte growth factors, insulin-like growth factors, intestinal trefoil factors, transforming growth factors, granulocyte colony-stimulating factors, nerve growth factors, and fibroblast growth factors.

Another embodiment of the invention is a cell culture media including a cell culture media base, lactoferrin, and at least one additional protein selected from the group consisting of epidermal growth factors, keratinocyte growth factors, insulin-like growth factors, intestinal trefoil factors, transforming growth factors, granulocyte colony-stimulating factors, nerve growth factors, fibroblast growth factors, transferrin, albumin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, and alpha-lactalbumin.

According to further embodiments, the proteins contained in the cell culture media are recombinant proteins, preferably recombinant human proteins. According to still further embodiments, one or more of the proteins in the cell culture media are plant-produced heterologous proteins, preferably two or more of the proteins in the cell culture media are plant-produced heterologous proteins, and more preferably all of the proteins in the cell culture media are plant-produced heterologous proteins.

According to further embodiments, a preferred combination of proteins that may be provided in the cell culture media includes lactoferrin and albumin.

Another embodiment of the invention provides methods for producing supplemented cell culture media, including providing a cell culture media base; providing two or more proteins selected from the group consisting of growth factors, lactoferrin, transferrin, albumin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, and alpha-lactalbumin; and combining the two or more proteins with the cell culture media base to form the supplemented cell culture media.

According to further embodiments, the proteins used in the methods for producing cell culture media are recombinant proteins, preferably recombinant human proteins. According to still further embodiments, one or more of the proteins used in the methods for producing cell culture media are plant-produced heterologous proteins, preferably two or more of the proteins used in the methods for producing cell culture media are plant-produced heterologous proteins, and more preferably all of the proteins used in the methods for producing cell culture media are plant-produced heterologous proteins.

According to further embodiments, the growth factors that may be provided in the methods of producing the cell culture media are selected from the group consisting of epidermal growth factors, keratinocyte growth factors, insulin-like growth factors, intestinal trefoil factors, transforming growth factors, granulocyte colony-stimulating factors, nerve growth factors, and fibroblast growth factors.

According to further embodiments, a preferred combination of proteins that may be used in the methods of producing the cell culture media includes lactoferrin and albumin.

Another embodiment of the invention provides a method for culturing cells, including providing a cell culture media base; supplementing the cell culture media base with two or more proteins selected from the group consisting of growth factors, lactoferrin, transferrin, albumin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, and alpha-lactalbumin to form a supplemented cell culture media; and introducing cells to be cultured into the supplemented cell culture media. The cells grown in the supplemented cell culture media exhibit improved growth characteristics as compared to cells grown in an unsupplemented cell culture media.

According to further embodiments, the proteins used in the methods for culturing cells are recombinant proteins, preferably recombinant human proteins. According to still further embodiments, one or more of the proteins used in the methods for culturing cells are plant-produced heterologous proteins, preferably two or more of the proteins used in the methods for culturing cells are plant-produced heterologous proteins, and more preferably all of the proteins used in the methods for culturing cells are plant-produced heterologous proteins.

According to further embodiments, the growth factors that may be used in the methods for culturing cells are selected from the group consisting of epidermal growth factors, keratinocyte growth factors, insulin-like growth factors, intestinal trefoil factors, transforming growth factors, granulocyte colony-stimulating factors, nerve growth factors, and fibroblast growth factors.

According to further embodiments, a preferred combination of proteins that may be used in the methods of culturing cells includes lactoferrin and albumin.

A further aspect of the invention includes methods for achieving an improved growth rate of cultured cells, and higher productivity of the cultured cells, by culturing the cultured cell in the cell culture media of the present invention In another embodiment, the invention includes a supplement comprising; a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a supplement comprising; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100,000, to about 1 to 1,000.

In one aspect of any of the claimed supplements, the recombinant albumin comprises at least about 0.01% wt/wt of a heat shock protein. In aspect of this embodiment, the heat shock protein is a rice heat shock protein. In another aspect, the heat shock protein is selected from the group consisting of Rice HSP70 genes, and rice endosperm lumenal binding protein. In another aspect, heat shock protein is selected from the group consisting of Rice (gb|ACJ54890.1|), EEC69073/Osl_37938, and AAB63469.

In another aspect of any of the claimed supplements, the recombinant albumin comprises at least about 0.01% wt/wt HSP70. In another aspect, the recombinant albumin comprises at least about 0.04% wt/wt HSP70. In another aspect, the recombinant albumin comprises at least about 0.06% wt/wt HSP70. In another aspect, the recombinant albumin comprises at least about 0.08% wt/wt HSP70. In another aspect, the recombinant albumin comprises at least about 0.1% wt/wt HSP70.

In another aspect of any of the claimed supplements, the transferrin related protein is lactoferrin. In another aspect of any of the claimed supplements, the transferrin related protein is transferrin. In one aspect, of any of the claimed supplements the lactoferrin is human. In one aspect, of any of the claimed supplements the transferrin is human. In one aspect, of any of the claimed supplements the lactoferrin is recombinant. In one aspect, of any of the claimed supplements the lactoferrin is derived from plasma. In one aspect, of any of the claimed supplements the transferrin is recombinant. In one aspect, of any of the claimed supplements the transferrin is derived from plasma. In one aspect, of any of the claimed supplements the IGF-1 is human. In one aspect, of any of the claimed supplements the IGF-1 is recombinant.

In another aspect of any of the claimed supplements, the ratio of transferrin to albumin about 1 to 50, to about 1 to 200. In another aspect of any of the claimed supplements, the ratio of the transferrin to the albumin about 1 to 75, to about 1 to 180. In another aspect of any of the claimed supplements, the ratio of the transferrin to the albumin about 1 to 80, to about 1 to 120. In another aspect of any of the claimed supplements, the ratio of the transferrin to the albumin about 1 to 50, to about 1 to 1000. In another aspect of any of the claimed supplements, the ratio of the transferrin to the albumin about 1 to 50, to about 1 to 2000. In another aspect of any of the claimed supplements, the ratio of the transferrin to the albumin about 1 to 50, to about 1 to 3000. In another aspect of any of the claimed supplements, the ratio of the transferrin to the albumin about 1 to 50, to about 1 to 4000. In another aspect of any of the claimed supplements, the ratio of the transferrin to the albumin about 1 to 50, to about 1 to 5000.

In another aspect of any of the claimed supplements, the ratio of lactoferrin to albumin is about 1 to 3, to about 1 to 0.33. In another aspect of any of the claimed supplements, the ratio of lactoferrin to albumin is about 1 to 0.5, to about 1 to 2. In another aspect of any of the claimed supplements, the ratio of lactoferrin to albumin is about 1 to 0.8, to about 1 to 1.2.

In another embodiment, the invention includes a method for enhancing cell growth of a cell in culture comprising the addition of a supplement to the cell culture medium, wherein the supplement comprises; a mixture of recombinant albumin and a transferrin related protein, wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for enhancing cell growth of a cell in culture comprising the addition of a supplement to the cell culture medium, wherein the supplement comprises; a mixture of recombinant albumin and an insulin related growth factor, wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for enhancing the productivity of a cell that has been adapted to serum free media comprising the addition of a supplement to the serum free media, wherein the supplement comprises; a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for enhancing the productivity of a cell that has been adapted to serum free media comprising the addition of a supplement to the serum free media, wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for reducing the accumulation of Lactate in a bioreactor comprising the addition of a supplement to cells in culture in the bioreactor; wherein the supplement comprises; a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for reducing the accumulation of Lactate in a bioreactor comprising the addition of a supplement to cells in culture in the bioreactor; wherein the supplement comprises; a mixture of recombinant albumin and an insulin related growth factor; wherein the recombinant albumin is i) produced in a plant, ii) has less than about 1 EU of endotoxin/ mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method or reducing the consumption of glucose and other sugars in a bioreactor comprising the addition of a supplement to cells in culture in the bioreactor; wherein the supplement comprises; a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method or reducing the consumption of glucose and other sugars in a bioreactor comprising the addition of a supplement to cells in culture in the bioreactor; wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method of reducing the time required to produce protein from start of culture to harvest in a bioreactor comprising the addition of a supplement to cells in culture in the bioreactor; wherein the supplement comprises; a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method of reducing the time required to produce protein from start of culture to harvest in a bioreactor comprising the addition of a supplement to cells in culture in the bioreactor wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the viability of cells in a bioreactor comprising the addition of a supplement to the bioreactor, wherein the supplement comprises; a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for improving the viability of cells in a bioreactor comprising the addition of a supplement to the bioreactor, wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the viability of cells grown under serum free conditions comprising the addition of a supplement to the serum free medium wherein the supplement comprises a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for improving the viability of cells grown under serum free conditions comprising the addition of a supplement to the serum free media, wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the viability of cells when plated at low density comprising the addition of a supplement to the cell culture medium wherein the supplement comprises a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for improving the viability of cells when plated at low density comprising the addition of a supplement to the cell culture medium, wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the viability of cells grown from single cell clones comprising the addition of a supplement to the cell culture medium wherein the supplement comprises a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for improving the viability of cells grown from single cell clones comprising the addition of a supplement to the cell culture medium, wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the viability of primary cells grown in culture comprising the addition of a supplement to the culture medium wherein the supplement comprises a mixture of recombinant albumin and a transferrin related protein; wherein the recombinant albumin is i) produced in a plant, ii) has less than about 1 EU of endotoxin,/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for improving the viability of primary cells grown in culture comprising the addition of a supplement to the cell culture medium wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the viability of cells after transfection comprising the addition of a supplement to the cell culture medium prior to, during, or immediately after transfection wherein the supplement comprises; a mixture of recombinant albumin and a transferrin related protein; wherein the recombinant albumin is i) produced in a plant, ii) has less than about 1 EU of endotoxin/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for improving the viability of cells after transfection comprising the addition of a supplement to the cell culture medium prior to, during, or immediately after transfection, wherein the supplement comprises; a mixture of recombinant albumin and an insulin related growth factor; wherein the recombinant albumin is i) produced in a plant, ii) has less than about 1 EU of endotoxin/mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the viability of cell after cryopreservation comprising the addition of a supplement to the cell culture medium prior to, during, or immediately after cryopreservation or thawing; wherein the supplement comprises; a mixture of recombinant albumin and a transferrin related protein; wherein the recombinant albumin is i) produced in a plant, ii) has less than about 1 EU of endotoxin,/mg of albumin; and iii) less than about 2% aggregated albumin; and wherein the supplement comprises a ratio (wt/wt) of transferrin related protein to albumin of about 1 to 5000, to about 1 to 0.5.

In another embodiment, the invention includes a method for improving the viability of cell after cryopreservation comprising the addition of a supplement to the cell culture medium prior to, during, or immediately after cryopreservation or thawing; wherein the supplement comprises; a mixture of recombinant albumin and an insulin related growth factor; wherein the recombinant albumin is i) produced in a plant, ii) has less than about 1 EU of endotoxin/ mg of albumin; and iii) less than about 2% aggregated albumin; and wherein the supplement comprises a ratio (wt/wt) of insulin related growth factor to albumin of about 1 to 100000, to about 1 to 1000.

In another embodiment, the invention includes a method for improving the yield of a recombinant product produced from cells in culture, comprising the addition of a supplement to the culture wherein the supplement comprises a mixture of recombinant albumin and a transferrin related protein; wherein the recombinant albumin is i) produced in a plant, ii) has less than about 1 EU of endotoxin,/mg of albumin; and iii) less than about 2% aggregated albumin; and wherein the supplement comprises a ratio (wt/wt) of transferrin related protein to albumin of about 1 to 5000, to about 1 to 0.5. In one aspect of this method, the viability of the cell culture is increased. In one aspect of this method the product is a protein or cell associated bacteria. In another aspect, the protein is an antibody. In one aspect, the protein is a recombinant protein, in another aspect, the protein is a monomer, in another aspect, the protein is a multimeric protein, in another aspect, and the antibody is full length. In another aspect, the antibody is a single chain antibody.

In another embodiment, the invention includes a method for improving the yield of a recombinant product produced from cells in culture, comprising the addition of a supplement to the culture wherein the supplement comprises; a mixture of recombinant albumin and an insulin related growth factor; wherein the recombinant albumin is i) produced in a plant, ii) has less than about 1 EU of endotoxin/ mg of albumin; and iii) less than about 2% aggregated albumin; and wherein the supplement comprises a ratio (wt/wt) of insulin related growth factor to albumin of about 1 to 100000, to about 1 to 5000. In one aspect of this method, the viability of the cell culture is increased. In one aspect of this method the product is a protein or cell associated bacteria. In another aspect, the protein is an antibody. In one aspect, the protein is a recombinant protein, in another aspect, the protein is a monomer, in another aspect, the protein is a multimeric protein, in another aspect, and the antibody is full length. In another aspect, the antibody is a single chain antibody.

In one aspect of any of these methods, the supplement further comprises insulin. In one aspect of any of these methods, the supplement further comprises IGF-1. In another aspect, the supplement further comprises selenium and ethanolamine.

In another aspect of any of the claimed methods, the cells are tissue culture cells. In another aspect, the cells are CHO cells. In another aspect the cells are hybridoma cells. In another aspect the cells are vero cells. In another aspect the cells are sorted by flow cytometry. In another aspect the cells are primary cells. In one aspect, the primary cells are embryonic stem cells. In another aspect the primary cells are B-cell derived. In another aspect the cells the primary cells are T-cell derived. In another aspect the cells are B-cells or B-cell derived. In another aspect the cells are T-cells or T-cell derived. In another aspect the cells. In another aspect the cells are isolated by a micro fluidic device. In another aspect the cells are isolated by single-cell subcloning.

In one aspect of any of the claimed methods, the recombinant albumin comprises at least about 0.01% wt/wt of a heat shock protein. In aspect of this embodiment, the heat shock protein is a rice heat shock protein. In another aspect, the heat shock protein is selected from the group consisting of Rice HSP70 genes, and rice endosperm lumenal binding protein. In another aspect, heat shock protein is selected from the group consisting of Rice (gb|ACJ54890.1|), EEC69073/Osl_37938, and AAB63469.

In another aspect of any of the claimed methods, the recombinant albumin comprises at least about 0.01% wt/wt HSP70. In another aspect, the recombinant albumin comprises at least about 0.04% wt/wt HSP70. In another aspect, the recombinant albumin comprises at least about 0.06% wt/wt HSP70. In another aspect, the recombinant albumin at least about 0.08% wt/wt HSP70. In another aspect, the recombinant albumin comprises at least about 0.1% wt/wt HSP70.

In another aspect of any of the claimed methods, the transferrin related protein is lactoferrin. In another aspect of any of the claimed methods the transferrin related protein is transferrin. In one aspect, of any of the claimed methods the lactoferrin is human. In one aspect, of any of the claimed methods the transferrin is human. In one aspect, of any of the claimed methods the lactoferrin is recombinant. In one aspect, of any of the claimed methods the transferrin is recombinant.

In another aspect of any of the claimed methods, the ratio of transferrin to albumin is about 1 to 50, to about 1 to 200. In another aspect of any of the claimed methods, the ratio of the transferrin to the albumin is about 1 to 75, to about 1 to 180. In another aspect of any of the claimed methods, the ratio of the transferrin to the albumin is about 1 to 80, to about 1 to 120. In another aspect of any of the claimed methods, the ratio of the transferrin to the albumin is about 1 to 120, to about 1 to 200. In another aspect of any of the claimed methods, the ratio of the transferrin to the albumin is about 1 to 200, to about 1 to 1000. In another aspect of any of the claimed methods, the ratio of the transferrin to the albumin is about 1 to 1000, to about 1 to 2000. In another aspect of any of the claimed methods, the ratio of the transferrin to the albumin is about 1 to 2000, to about 1 to 3000. In another aspect of any of the claimed methods, the ratio of the transferrin to the albumin is about 1 to 3000, to about 1 to 4000. In another aspect of any of the claimed methods, the ratio of the transferrin to the albumin is about 1 to 4000, to about 1 to 5000.

In another aspect of any of the claimed methods, the ratio of lactoferrin to albumin is about 1 to 3, to about 1 to 0.33. In another aspect of any of the claimed methods, the ratio of lactoferrin to albumin is about 1 to 0.5, to about 1 to 2. In another aspect of any of the claimed methods, the ratio of lactoferrin to albumin is about 1 to 0.8, to about 1 to 1.2.

In another aspect of any of the claimed methods comprising lactoferrin, the lactoferrin is added to a final concentration of between about 100 mg/L and 400 mg/L. In another aspect of any of the claimed methods comprising lactoferrin, the lactoferrin is added to a final concentration of between about 400 mg/L and 800 mg/L. In another aspect of any of the claimed methods comprising lactoferrin, the lactoferrin is added to a final concentration of between about 800 mg/L and 1000 mg/L. In another aspect of any of the claimed methods comprising lactoferrin, the lactoferrin is added to a final concentration of between about 1000 mg/L and 2000 mg/L.

In another aspect of any of the claimed methods comprising transferrin, the transferrin is added to a final concentration of between about 1 ug/L and 50 ug/L. In another aspect of any of the claimed methods comprising transferrin, the transferrin is added to a final concentration of between about 2 ug/L and 10 ug/L In another aspect of any of the claimed methods comprising transferrin, the transferrin is added to a final concentration of between about 3 ug/L and 8 ug/L. In another aspect of any of the claimed methods comprising transferrin, the transferrin is added to a final concentration of between about 4 ug/L and 6 ug/L.

In another aspect of any of the claimed methods the recombinant albumin is added to a final concentration of between about 100 mg/L and 2000 mg/L. In another aspect of any of the claimed methods the recombinant albumin is added to a final concentration of between about 200 mg/L and 1000 mg/L.

In another aspect of any of the claimed methods the improvement in cell viability is greater than 30% compared to the summed effect of recombinant albumin and transferrin related protein when added alone under the same culture conditions.

In another aspect of any of the claimed methods the improvement in cell viability is greater than 40% compared to the summed effect of recombinant albumin or transferrin related protein when added alone under the same culture conditions.

In another aspect of any of the claimed methods the improvement in cell viability is greater than 50% compared to the summed effect of recombinant albumin or transferrin related protein when added alone under the same culture conditions.

In another aspect of any of the claimed methods the improvement in cell viability is greater than 60% compared to the summed effect of recombinant albumin or transferrin related protein when added alone under the same culture conditions.

In another aspect of any of the claimed methods the improvement in cell viability is greater than 70% compared to the summed effect of recombinant albumin or transferrin related protein alone when measured under the same culture conditions.

In another aspect of any of the claimed methods the improvement in cell viability is greater than 80% compared to the summed effect of recombinant albumin or transferrin related protein when added alone under the same culture conditions.

In another aspect of any of the claimed methods the improvement in cell viability is greater than 90% compared to the summed effect of recombinant albumin or transferrin related protein when added alone under the same culture conditions.

In another aspect of any of the claimed methods the improvement in cell viability is greater than 100% compared to the summed effect of recombinant albumin or transferrin related protein when added alone under the same culture conditions.

In another aspect of any of the claimed methods the improvement in cell viability is greater than 150% compared to the summed effect of recombinant albumin or transferrin related protein when added alone under the same culture conditions.

In another aspect of any of the claimed methods the improvement in cell viability is greater than 200% compared to the summed effect of recombinant albumin or transferrin related protein when added alone under the same culture conditions.

Other novel features and advantages of the present invention will become apparent to those skilled in the art upon examination of the following or upon learning by practice of the invention.

BRIEF DESCRIPTION OF THE FIGURES

For a more complete understanding of the present invention, the needs satisfied thereby, and the objects, features, and advantages thereof, reference now is made to the following description taken in connection with the accompanying drawings.

Figure 1A:
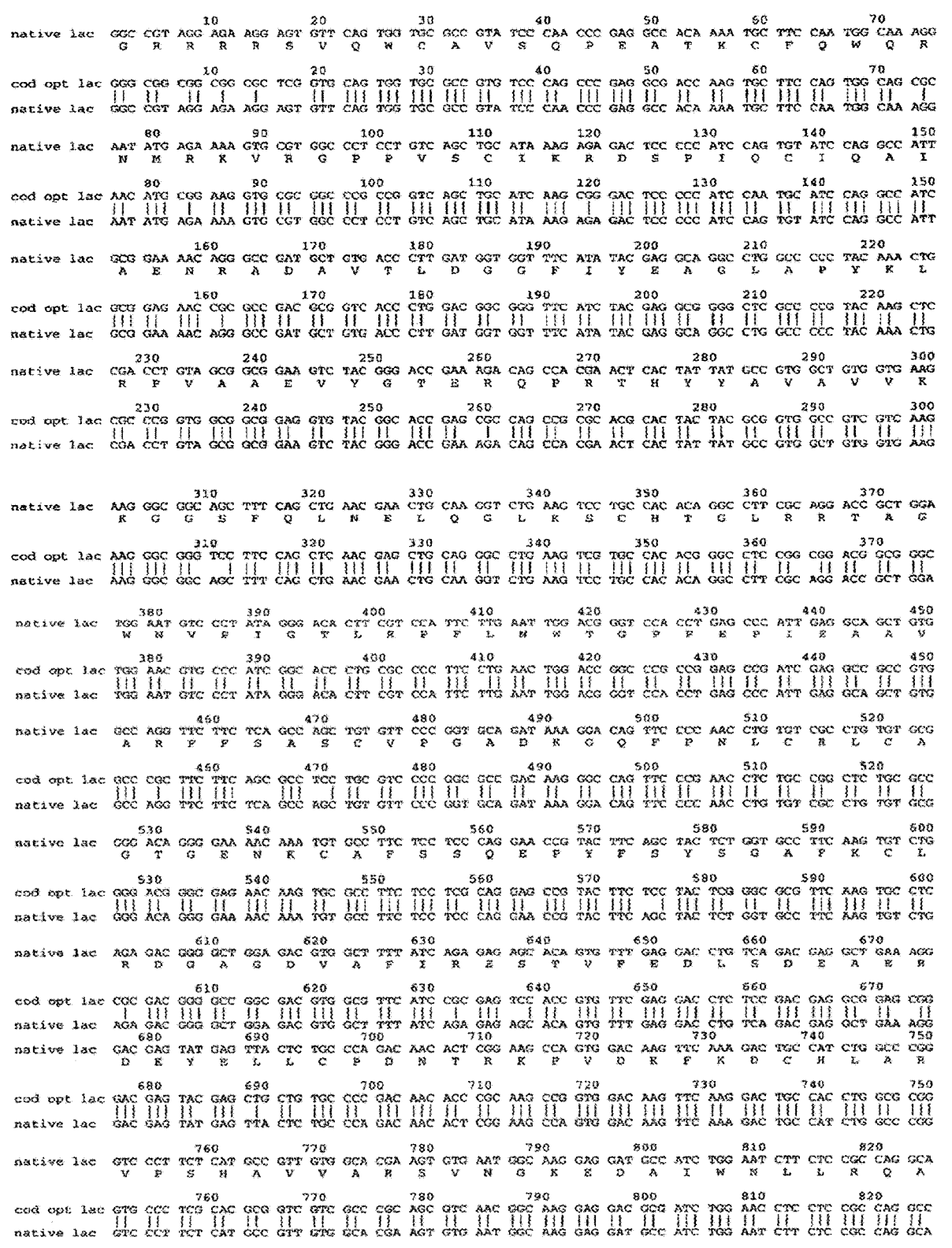
Figure 1B:
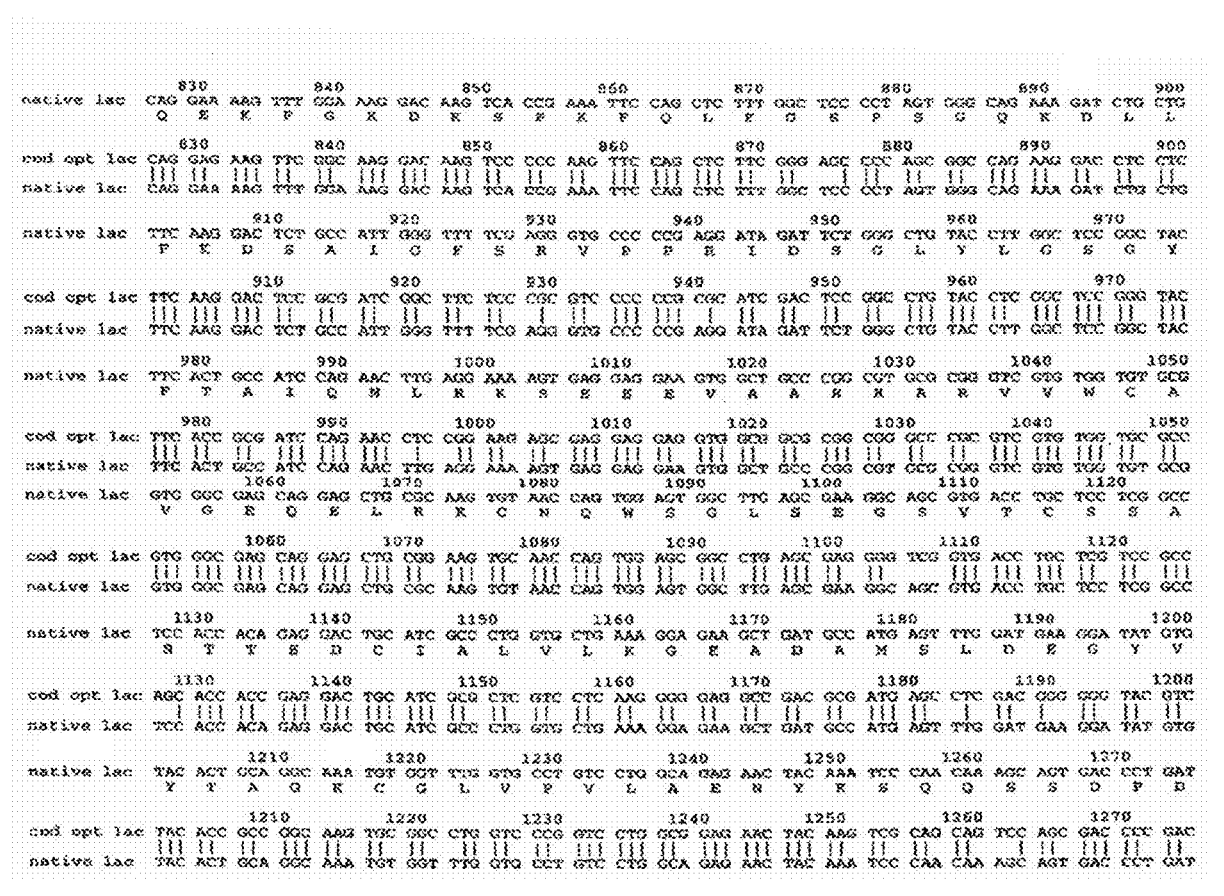
Figure 1C:
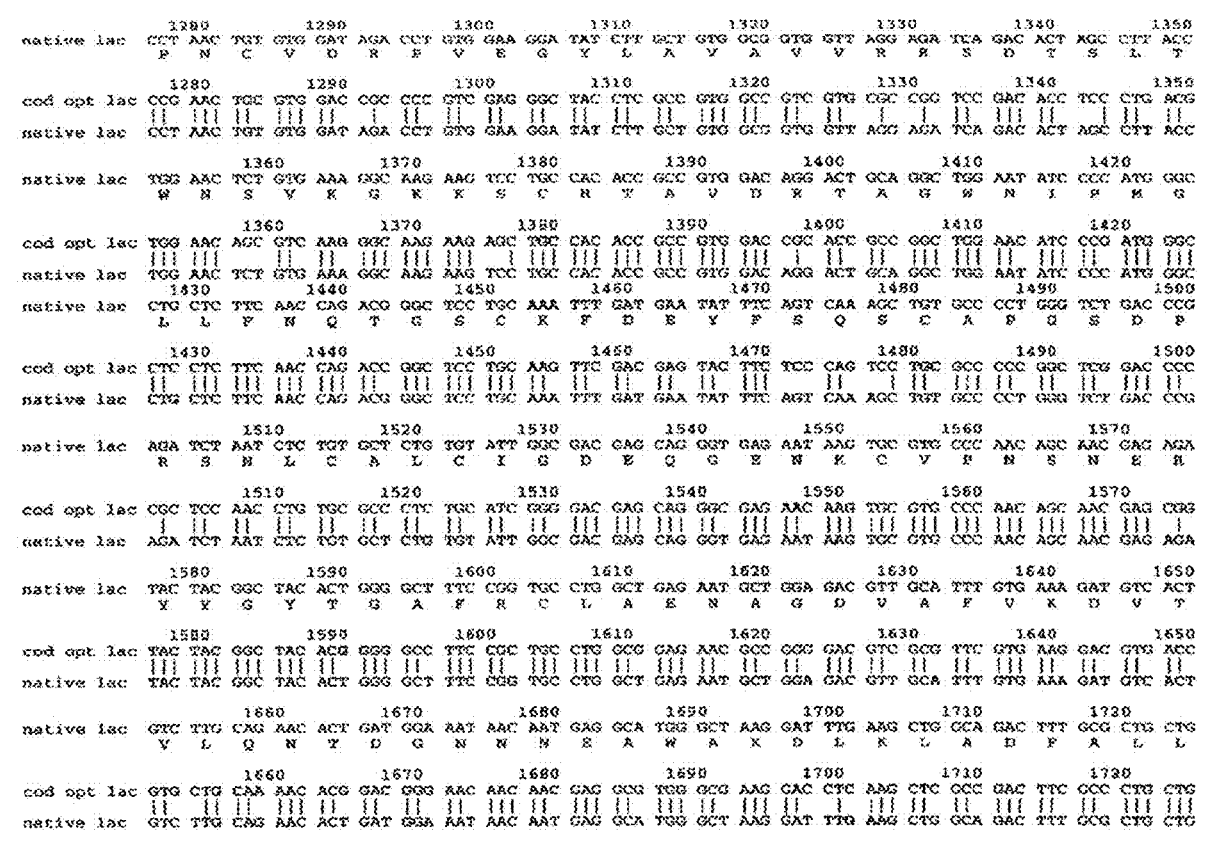

FIG. 1A is a comparison of the codon-optimized human lactoferrin sequence ("cod opt lac") with a native human lactoferrin sequence ("native lac"), aligned to show 693 codons, with 413 (59.6%) codon changes and 467 (22.5%) nucleotide changes.

FIG. 1B is a comparison of the codon-optimized human lactoferrin sequence ("cod opt lac") with a native human lactoferrin sequence ("native lac"), aligned to show 693 codons, with 413 (59.6%) codon changes and 467 (22.5%) nucleotide changes.

FIG. 1C is a comparison of the codon-optimized human lactoferrin 5 sequence ("cod opt lac") with a native human lactoferrin sequence ("native lac"), aligned to show 693 codons, with 413 (59.6%) codon changes and 467 (22.5%) nucleotide changes.

FIG. 1D is a comparison of the codon-optimized human lactoferrin sequence ("cod opt lac") with a native human lactoferrin sequence ("native lac"), aligned to show 693 codons, with 413 (59.6%) codon changes and 467 (22.5%) nucleotide changes.

FIG. 5A shows DNA and protein sequence of fusion between Gt1 signal peptide (Gt1 SP) and codon-optimized human albumin (OPTIMIZED HSA) sequence based on native protein sequence derived from P02768 (Swiss-Prot).

FIG. 5B shows DNA and protein sequence of fusion between Gt1 signal peptide (Gt1 SP) and codon-optimized human albumin (OPTIMIZED HSA) sequence based on native protein sequence derived from P02768 (Swiss-Prot).

FIG. 5C shows DNA and protein sequence of fusion between Gt1 signal peptide (Gt1 SP) and codon-optimized human albumin (OPTIMIZED HSA) sequence based on native protein sequence derived 5 from P02768 (Swiss-Prot).

FIG. 5D shows DNA and protein sequence of fusion between Gt1 signal peptide (Gt1 SP) and codon-optimized human albumin (OPTIMIZED HSA) sequence based on native protein sequence derived from P02768 (Swiss-Prot).

FIG. 8A shows the chromatogram for a serum derived (non-recombinant HSA). FIG. 8B shows the chromatogram for a rice recombinant HSA (Cellastim P0107) made using the "old process" B000 for purification. FIG. 8C shows the chromatogram for a rice recombinant HSA (Cellastim P0171) made using the "new process" B00000 for purification. FIG. 8D shows an overlay of the chromatograms for the serum derived albumin (1A; dotted line) and Cellastim HSA prepared using the new process ((1C; solid line). FIG. 8E shows an overlay of the chromatograms for HSA prepared using the old process B000 (Cellastim P0107) (1B; dotted line) and HSA prepared using the new process B00000 (Cellastim P0171) (10; solid line).

FIG. 9A shows a comparison of Cellastim P0171albumin and Cellprime albumin (Millipore/Novozymes). Lane 1 is the molecular weight marker. Lane 4 is the Cellastim albumin (10 µg) and Lane 7 is the Cellprime albumin (10 µg). FIG. 9B shows a comparison by SDS PAGE analysis of three Cellastim lots from the previous process (B000) (Lane 2, 3, and 4), and the new Cellastim Process (B0000C) (Lane 6, 7, and 8). The six samples were loaded at 20 µg per lane.

DETAILED DESCRIPTION OF THE PREFERRED EMBODIMENTS

Definitions

Figure 2:
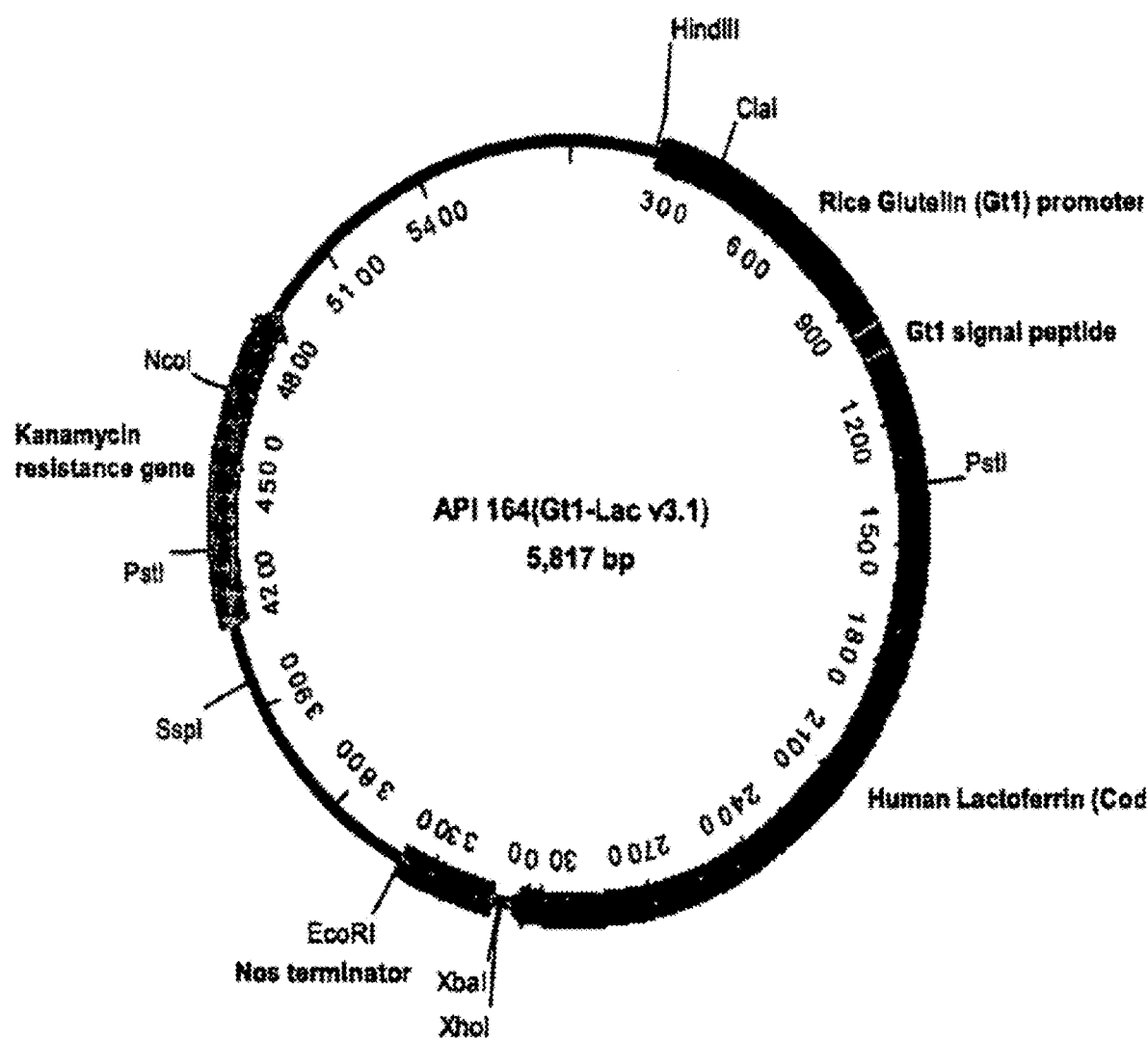
FIG. 2 is a plasmid map of the 5,817 bp plasmid, API164 (GT1-Lac), showing an expression cassette for human lactoferrin and containing a Gt1 promoter, a Gt1 signal peptide, codon optimized human lactoferrin, a Nos terminator and a kanamycin resistance selectable marker.

In order that the present disclosure may be more readily understood, certain terms are first defined. Additional definitions are set forth throughout the detailed description. Unless otherwise indicated, all terms used herein have the meanings given below, or are generally consistent with same meaning that the terms have to those skilled in the art of the present invention. Practitioners are particularly directed to Sambrook et al. (1989) *Molecular Cloning: A Laboratory Manual* (Second Edition), Cold Spring Harbor Press, Plainview, N.Y.; Ausubel F M et al. (1993); *Current Protocols in Molecular Biology*, John Wiley & Sons, New York, N.Y.; and Gelvin and Schilperoot, eds. (1997) *Plant Molecular Biology Manual*, Kluwer Academic Publishers, The Netherlands, for definitions and terms of the art.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

The term "antigen-binding fragment" refers to a polypeptide portion of an immunoglobulin or antibody that binds antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', F(ab')$_2$, Fabc, Fv, single chains, and single-chain antibodies.

The term "apoptosis" ("normal" or "programmed" cell death) refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine dependent tissue atrophy. Apoptosis may also be triggered in cells grown under tissue culture conditions in response to stress. Cells undergoing apoptosis show characteristic morphological and biochemical features, which can be readily measured and quantified. These features include chromatin aggregation, nuclear and cytoplasmic condensation, partition of cytoplasm and nucleus into membrane bound vesicles (apoptotic bodies) which contain ribosomes, morphologically intact mitochondria and nuclear material. In vivo, these apoptotic bodies are rapidly recognized and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis".

As used herein, the terms "cell," "cells," "cell line," "host cell," and "host cells," are used interchangeably and, encompass plant, and animal cells and include invertebrate, non-mammalian vertebrate and mammalian cells. All such designations include cell populations and progeny. Thus, the terms "transformants" and "transfectants" include the primary subject cell and cell lines derived therefrom without regard for the number of transfers. Exemplary non-mammalian vertebrate cells include, for example, avian cells, reptilian cells and amphibian cells. Exemplary invertebrate cells include, but are not limited to, insect cells such as, for example, caterpillar (*Spodoptera frugiperda*) cells, mosquito (*Aedes aegypti*) cells, fruitfly (*Drosophila melanogaster*) cells, Schneider cells, and *Bombyx mori* cells. See, e.g., Luckow et al., Bio/Technology 6:47-55 (1988). The cells may be differentiated, partially differentiated or undifferentiated, e.g. stem cells, including embryonic stem cells and pluripotent stem cells. Additionally tissue samples derived from organs or organ systems may be used according to the invention. Exemplary mammalian cells include, for example, cells derived from human, non-human primate, cat, dog, sheep, goat, cow, horse, pig, rabbit, rodents including mouse, hamster, rat and guinea pig and any derivatives and progenies thereof.

The terms "cell culture," or "tissue culture" refer to cells grown in suspension or grown adhered to a variety of surfaces or substrates in vessels such as roller bottles, tissue culture flasks, dishes, multi-well plates and the like. Large scale approaches, such as bioreactors, including adherent cells growing attached to microcarriers in stirred fermentors, are also encompassed by the term "cell culture." Moreover, it is possible not only to culture contact-dependent cells, but also to use suspension culture techniques in the methods of the claimed invention. Exemplary microcarriers include, for example, dextran, collagen, plastic, gelatin and cellulose and others as described in Butler, Spier & Griffiths, Animal cell Biotechnology 3:283-303 (1988). Porous carriers, such as, for example, Cytoline™ or Cytopore™ as well as dextran-based carriers, such as DEAE-dextran (Cytodex 1™ quaternary amine-coated dextran (Cytodex™) or gelatin-based carriers, such as gelatin-coated dextran (Cytodex 3™) may also be used. Cell culture procedures for both large and small-scale production of proteins are encompassed by the present invention. Procedures including, but not limited to, a fluidized bed bioreactor, hollow fiber bioreactor, roller bottle culture, or stirred tank bioreactor system may be used, with or without microcarriers, and operated alternatively in a batch, fed-batch, or perfusion mode.

The terms "cell culture medium," "cell culture media," and "culture medium" refer to the solutions used for growing, storing, handling and maintaining cells and cell lines. Such solutions generally include various factors necessary for cell attachment, growth, and maintenance of the cellular environment. For example, a typical solution may include a basal media formulation, various supplements depending on the cell type and, occasionally, antibiotics. In some embodiments, a solution may include at least one component from one or more of the following categories: 1) an energy source, usually in the form of a carbohydrate such as glucose; 2) all essential amino acids, and usually the basic set of twenty amino acids plus cystine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The solution may optionally be supplemented with one or more components from any of the following categories: 1) hormones and other growth factors as, for example, insulin, transferrin, and epidermal growth factor; 2) salts and buffers as, for example, calcium, magnesium, phosphate, Tris, HEPES, and sodium bicarbonate; 3) nucleosides and bases such as, for example, adenosine and thymidine, hypoxanthine; and 4) protein and tissue hydrolysates. In general, any suitable cell culture medium may be used. The medium may be comprised of serum, e.g. fetal bovine serum, calf serum or the like. Alternatively, the medium may be serum free, animal free, or protein free.

The term "cell culture media component" or "cell culture component" refers to any heterologous proteins used as a supplement for cell culture media.

The term "cell culture media ingredient" includes Cell culture media components, proteins, peptides, hormones, carbohydrates, amino acids, lipids, vitamins, antibiotics, organic and inorganic salts.

The term "cell culture media supplement" refers to a combination of one or multiple cell culture media components, with or without other ingredients, for addition to cell culture media.

The term "cell culture media base" or "basal media" refers to a cell culture media that may contain, for example, any or all of the following components: proteins, peptides, lipids, carbohydrates, amino acids, organic and/or inorganic salts, buffers (e.g., bicarbonate), vitamins, hormones, antibiotics, and pH indicators (e.g., phenol red). Examples of cell culture media bases that can be used in accordance with the present invention include: Dulbecco's Modified Eagle's Medium (DME), Ham's Nutrient Mixtures, MCDB Media, Minimum Essential Medium Eagle, RPMI Media, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, and William's Medium E. The cell culture media base may be supplemented using a cell culture media component or a cell culture media supplement.

The term "cell lineage" when referring to a stem cell culture refers to all of the stages of the development of a cell type, from the earliest precursor cell to a completely mature cell (i.e. a specialized cell).

The terms "cell viability" or "viability" refers to relative amounts of living and dead cells, present with a population of cells at any given time. Cell viability may be determined by measuring the relative numbers of living and dead cells in any given sample of the population. Cell viability may also be estimated by measuring the rate of cell proliferation of the entire population which represents the overall balance of the rates of cell growth and cell death. Rates of cell growth may also be directly measured, by counting the number of cells, and by using any number of commercially available cell proliferation assays which directly scores the rate of cell growth. "Conditioned medium" refers to a cell culture medium that is obtained from a culture of a feeder cell on which embryonic stem cells can be cultured and maintained in a pluripotent state. The feeder cell depletes the conditioned medium of some components, but also enriches the medium with cell-derived material, probably including small amounts of growth factors. The term "feeder cell factor" as used herein means the cell-derived material that is released into the conditioned medium by the feeder cell. The cell factor that is released into the cell culture medium is useful in enhancing the growth of embryonic stem cells, or in the maintenance of the embryonic stem cell in a pluripotent state. The feeder cell factor can be identified and purified using techniques that are known to one skilled in the art, and are described herein.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag).

Examples of amino acid groups defined in this manner include: a "charged/polar group," consisting of Glu, Asp, Asn, Gln, Lys, Arg and His; an "aromatic, or cyclic group," consisting of Pro, Phe, Tyr and Trp; and an "aliphatic group" consisting of Gly, Ala, Val, Leu, Ile, Met, Ser, Thr and Cys.

Within each group, subgroups can also be identified, for example, the group of charged/polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala.

Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free—OH can be maintained; and Gln for Asn such that a free—$NH_2$ can be maintained.

The term "cytotoxicity" refers to the cell killing property of a chemical compound (such as a chemical or protein contaminant, detergent, or toxin). In contrast to necrosis and apoptosis, the term cytotoxicity need not necessarily indicate a specific cellular death mechanism.

As used herein, the term "decrease" or the related terms "decreased," "reduce" or "reduced" refers to a statistically significant decrease. For the avoidance of doubt, the terms generally refer to at least a 10% decrease in a given parameter, and can encompass at least a 20% decrease, 30% decrease, 40% decrease, 50% decrease, 60% decrease, 70% decrease, 80% decrease, 90% decrease, 95% decrease, 97% decrease, 99% decrease or even a 100% decrease (i.e., the measured parameter is at zero).

As used herein, the terms "develop", "differentiate" and "mature", as used to describe a stem cell, refer to the progression of a cell from the stage of having the potential to differentiate into at least two different cellular lineages to becoming a specialized and terminally differentiated cell. Such terms can be used interchangeably for the purposes of the present application.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantified by Northern blot hybridization, ribonuclease RNA protection, in situ hybridization to cellular RNA or by PCR. Proteins encoded by a selected sequence can be quantified by various methods including, but not limited to, e.g., ELISA, Western blotting, radioimmunoassays, immunoprecipitation, assaying for the biological activity of the protein, or by immunostaining of the protein followed by FACS analysis.

"Expression control sequences" are DNA regulatory sequences, such as promoters, enhancers, polyadenylation signals, terminators, internal ribosome entry sites (IRES) and the like, that provide for the expression of a coding sequence in a host cell. Exemplary expression control sequences are described in Goeddel; Gene Expression Technology: Methods in Enzymology 185, Academic Press, San Diego, Calif. (1990).

The term "feeder cell" refers to a culture of cells that grows in vitro and secretes at least one factor into the culture medium, and that can be used to support the growth of another cell of interest in culture. As used herein, a "feeder cell layer" can be used interchangeably with the term "feeder cell." A feeder cell can comprise a monolayer, where the feeder cells cover the surface of the culture dish with a complete layer before growing on top of each other, or can comprise clusters of cells.

The term "growth phase" of the cell culture refers to the period of exponential cell growth (the log phase) where cells are dividing at a constant rate. During this phase, cells are cultured for a period of time, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives usually at about 30-40° C., generally about 37° C., in a humidified, controlled atmosphere, such that optimal growth is achieved for the particular cell line, for instance a mammalian cell.

The term "heterologous DNA" refers to DNA which has been introduced into a cell that is derived from another source, or which is from the same source but is located in a different (i.e. non native) context. The term "heterologous protein" or "recombinant protein" refers to a protein encoded in all or part by heterologous DNA, or a protein that is expressed from expression control sequences (such as a promoter, or enhancer) created in whole or part by the heterologous DNA which activates the expression of an endogenous gene.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., Cell, 50:667, 1987). Such proteins (and their encoding nucleic acids) have sequence homology, as reflected by their sequence similarity, whether in terms of percent identity or by the presence of specific residues or motifs and conserved positions.

The term "growth factor" refers to Amphiregulin, Angiopoietin, Betacellulin, (Bone Morphogenic protein-13, Bone Morphogenic protein-14, Bone Morphogenic protein-2, Human BMP-3, Bone Morphogenic protein-4, Human BMP-5, Bone Morphogenic protein-6, Bone Morphogenic protein-7, Human CD135 Ligand/Flt-3 Ligand, Human Granulocyte Colony Stimulating Factor (G-CSF), Human Granulocyte Macrophage Colony Stimulating Factor (GM-CSF), Human Macrophage Colony Stimulating Factor (M-CSF), Human Cripto-1, Human CTGF (Connective tissue growth factor), Human EGF (Epidermal Growth Factor), Human EG-VEGF (Endocrine-Gland-Derived Vascular Endothelial Growth Factor), Human Erythropoietin (EPO), Human FGF (Fibroblast Growth Factors 1-23), Human GDF-11, Human GDF-15, Human GDF-8, Human Growth Hormone Releasing Factor (GHRF, GRF, GHRH, Growth Hormone Releasing Hormone), Human Heparin Binding Epidermal Growth Factor (HB-EGF), Human Hepatocyte Growth Factor (HGF), Human Heregulin beta 1, Human insulin, Human IGF-1 (Insulin-like Growth Factor-1), Human IGF-2 (Insulin-like Growth Factor-2), Human IGFBP-1 (Insulin-like Growth Factor Binding Protein 1), Human IGFBP-3 (Insulin-like Growth Factor Binding Protein 3), intestinal trefoil factor (ITF), Human keratinocyte growth factors 1 & 2, Human Leukemia Inhibitory Factor (LIF), Human MSP, Human Myostatin, Human Myostatin, pro (propeptide), Human NRG1, Human NGF, Human Oncostatin M, Human Osteoblast Specific Factor 1 (OSF-1, Pleiotrophin), Human PD-ECGF (Platelet-derived endothelial cell growth factor), Human PDGF, Human PlGF, Human Placental Growth Factor 1 (PLGF1), Human Placental Growth Factor 2 (PLGF2), Human SCGF-a (Stem Cell Growth Factor-alpha), Human SCGF-b (Stem Cell Growth Factor-beta), Human Stem Cell Factor (SCF)/CD117 Ligand, Human Thrombopoietin (TPO, THPO), Human Transforming Growth Factor, Human TGF-alpha (Transforming Growth Factor-alpha, TGFa), Human TGF-beta 1 (Transforming Growth Factor-beta1, TGFb), Human TGF-beta 1.2 (Transforming Growth Factor-beta1, TGFb), Human TGF-beta 2 (Transforming Growth Factor-beta2, TGFb), Human TGF-beta 3 (Transforming Growth Factor-beta3, TGFb), Human VEGF (Vascular Endothelial Growth Factor), Human VEGF-121, Human VEGF-165, and Human VEGF-A.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm can also be used to determine identity.

The terms "immunoglobulin" or "antibody" (used interchangeably herein) refers to a protein typically having a basic four-polypeptide chain structure consisting of two heavy and two light chains, the chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, the chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by beta-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains). Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments.

As used herein, the term "increase" or the related terms "increased", "enhance" or "enhanced" refers to a statistically significant increase. For the avoidance of doubt, the terms generally refer to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control value.

The term "isolated," when used to describe the cell culture components, i.e. albumin, or transferrin related proteins disclosed herein, means protein that has been identified and separated and/or recovered from a component of its natural environment. Contaminant components of its natural environment are materials that would typically interfere with research, diagnostic or therapeutic uses for the protein, and may include enzymes, hormones, and other proteinaceous or non-proteinaceous solutes. In some embodiments, the protein will be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated protein will be prepared by at least one purification step.

The term "maturation-specific protein promoter" refers to a promoter exhibiting substantially up-regulated activity (greater than 25%) during seed maturation.

The term "mature plant" refers to a fully differentiated plant.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

Cells expressing "markers of pancreatic endocrine lineage" refer to cells with positive gene expression for the transcription factor PDX-1 and at least one of the following transcription factors: NGN-3, NRx2.2, NRx6.1, NeuroD, 151-1, HNF-3 beta, MAFA, Pax4, and Pax6. Cells expressing markers characteristic of the pancreatic cell lineage include pancreatic β cells.

Cells expressing "markers characteristic of endoderm lineage" as used herein refer to cells expressing at least one of the following markers: SOX-17, GATA-4, HNF-3 beta, GSC, Cer1, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

Cells expressing pluripotency markers derived by the methods of the present invention express at least one of the following pluripotency markers selected from the group consisting of: ABCG2, cripto, FoxD3, Connexin43, Connexin45, Oct4, SOX-2, Nanog, hTERT, UTF-1, ZFP42, SSEA-3, SSEA-4, Tral-60, and Tral-81.

Cells expressing "markers characteristic of mesoderm lineage" as used herein refers to a cell expressing at least one of the following markers: CD48, eomesodermin (EOMES), SOX-17, DKK4, HNF-3 beta, GSC, FGF17, GATA-6.

Cells expressing "markers characteristics of ectoderm lineage" as used herein refers to a cell expressing at least one of the following markers: BMP-4. Noggin, Chordin, Otx2, Fox J3, Nestin, p63/TP73L, beta-III Tubulin.

"Monocot seed components" refers to carbohydrate, protein, and lipid components extractable from monocot seeds, typically mature monocot seeds.

As used herein, the terms "native" or "wild-type" relative to a given cell, protein, polypeptide, nucleic acid, trait or phenotype, refers to the form in which that is typically found in nature.

The terms "operably linked" and "operatively linked," as used interchangeably herein, refer to the positioning of two or more nucleotide sequences or sequence elements in a manner which permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule may additionally include one or more nucleotide sequences chosen from: (a) a nucleotide sequence capable of increasing translation; (b) a nucleotide sequence capable of increasing secretion of the recombinant protein outside a cell; and (c) a nucleotide sequence capable of increasing the mRNA stability, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein; it is not necessarily contiguous with it. Operable linking of various nucleotide sequences is accomplished by recombinant methods well known in the art, e.g. using PCR methodology, by ligation at suitable restrictions sites or by annealing. Synthetic oligonucleotide linkers or adaptors can be used in accord with conventional practice if suitable restriction sites are not present.

A "plant cell" refers to any cell derived from a plant, including undifferentiated tissue (e.g., callus) as well as plant seeds, pollen, propagules, embryos, suspension cultures, meristematic regions, leaves, roots, shoots, gametophytes, sporophytes and microspores.

The terms "polynucleotide" and "nucleic acid molecule," used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The term "pluripotent stem cell" encompasses stem cells obtained from embryos, fetuses or adult tissues. In one preferred embodiment, the pluripotent stem cell is an embryonic stem cell. In another embodiment the pluripotent stem cell is a fetal stem cell, such as a primordial germ cell. In another embodiment the pluripotent stem cell is an adult stem cell.

As used herein, the term "pluripotent" refers to a cell capable of at least developing into one of ectodermal, endodermal and mesodermal cells. As used herein the term "pluripotent" includes cells that are totipotent and multipotent. As used herein, the term "totipotent cell" refers to a cell capable of developing into all lineages of cells. The term "multipotent" refers to a cell that is not terminally differentiated.

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter, the rice endosperm specific glutelin (Gt1) promoter, CaMV35S viral promoter. Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-RE$_x$™ system (Invitrogen Carlsbad, Calif.), LacSwitch® (Stratagene, (San Diego, Calif.) and the Cre-ERT tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

The term "protein of interest" refers to any protein which may be useful for research, diagnostic or therapeutic purposes. The protein of interest may comprise a mammalian protein or non-mammalian protein, and may optionally comprise a receptor or a ligand. Exemplary proteins of interest include, but are not limited to, molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; members of the TNF and TNF receptor (TNFR) family, like tumor necrosis factor-alpha and -beta, CD40 ligand, Apo-2 ligand/TRAIL, DR4, DR5, DcR1, DcR2, DcR3, OPG, Fas ligand; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TG-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; thrombopoietin (TPO); interleukins (ILs), e.g., IL-1 to IL-10; superoxide dismutase; T-cell receptors; surface membrane proteins; decay accelerating factor; viral antigen such as, for example, a portion of the AIDS envelope, gp120; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and variants and/or fragments of any of the above-listed polypeptides; as well as antibodies against various protein antigens like CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150.95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C; an Apo-2L receptor such as Apo-2 (DR5), DR4, DcR1, DcR2, DcR3; and variants and/or fragments of the above-identified antibodies etc. In one embodiment of the invention, a protein of interest will comprise a protein which itself is capable of inducing apoptosis in mammalian or non-mammalian cells in vitro or in vivo, such as Apo-2 ligand/TRAIL, Fas ligand, or TN F-alpha.

The term "production phase" of the cell culture refers to the period of time during which cell Growth has reached a plateau. During the production phase, logarithmic cell growth has ended and protein production is primary. During this period of time the medium is generally supplemented to support continued protein production and to achieve the desired protein product.

The term "produced in a plant" when used to describe the cell culture components disclosed herein, means that the protein has been obtained directly or indirectly from a plant cell. With respect to recombinant proteins, the term "produced in a plant" means that the recombinant protein has been expressed within a plant cell, and then purified from host cells proteins and lipids. Proteins that have been produced in a plant may be differentiated from proteins that have purified from other organisms by at least three criteria. 1) Proteins produced in a plant will typically comprise different patterns of post-translational modifications compared to proteins produced in different organisms, which may be readily identified by mass spectrum analysis. 2) Proteins produced in a plant will typically comprise a different set of bound co-factors, lipids and contaminating proteins compared to the same protein produced in a different expression system, or purified from a different source. 3) Proteins produced in a plant may exhibit a different biological activity compared to the same protein produced or purified from a different source. The difference in activity in the protein produced in a plant may arise from a difference in the conformation, folding, aggregation state, post-translational modifications, or bound factors or co-purified contaminating proteins of the protein produced in a plant compared to a protein produced or isolated from a different organism. Differences in the specific activity of a protein produced in a plant may be readily established by routine assays using defined concentrations and assay conditions, for example, using cell growth, and factor synergism assays, as disclosed in Examples 11 to 19. Specifically a protein produced in a plant may exhibit at least at least 10% greater cell growth activity either alone, or in combination with other factors, compared to the same concentration of a non plant produced protein. Preferably, a protein produced in a plant may exhibit at least at least 20% greater cell growth activity either alone, or in combination with other factors, compared to the same concentration of a non plant produced protein. More preferably, a protein produced in a plant may exhibit at least at least 30% greater cell growth activity either alone, or in combination with other factors, compared to the same concentration of a non plant produced protein. More preferably, a protein produced in a plant may exhibit at least at least 40% greater cell growth activity either alone, or in combination with other factors, compared to the same concentration of a non plant produced protein. Even more preferably, a protein produced in a plant may exhibit at least at least 50% greater cell growth activity either alone, or in combination with other factors, compared to the same concentration of a non plant produced protein.

The terms "isolated" or "purified" when used to describe the cell culture components disclosed herein, means protein that has been identified and separated and/or recovered from a component of its natural environment. Contaminant components of its natural environment are materials that would typically interfere with research, diagnostic or therapeutic uses for the protein, and may include enzymes, hormones, and other proteinaceous or non-proteinaceous solutes. In some embodiments, the protein will be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated protein will be prepared by at least one purification step.

The term "recombinant protein" or "recombinant polypeptide" refers to an exogenous, i.e., heterologous or foreign polypeptide, to the cells producing the polypeptide.

The term "stress" in the context of apoptosis or cell culture refers to non-optimal conditions for tissue culture including any combination of the following; the presence of toxins, nutrient or growth factor depletion or withdrawal, hypoxia, thermal stress (temperature is too high or too low compared to the preferred range), loss of cell-cell contacts, viral infection, osmotic stress (osmolality is too high or too low compared to the preferred range), oxidative stress, cell density (cell density is too high or too low compared to the preferred range), and pH stress (pH is too high or too low compared to the preferred range).

The term "transformation" refers to the transfer of one or more nucleic acid molecules into a host cell or organism. Methods of introducing nucleic acid molecules into host cells include, for instance, calcium phosphate transfection, DEAE-dextran mediated transfection, microinjection, cationic lipid-mediated transfection, electroporation, scrape loading, ballistic introduction or infection with viruses or other infectious agents. "Transformed", "transduced", "transgenic", and "recombinant" refer to a host cell or organism into which a recombinant or heterologous nucleic acid molecule (e.g., one or more DNA constructs or RNA, or siRNA counterparts) has been introduced. The nucleic acid molecule can be stably expressed (i.e. maintained in a functional form in the cell for longer than about three months) or non-stably maintained in a functional form in the cell for less than three months i.e. is transiently expressed. For example, "transformed," "transformant," and "transgenic" cells have been through the transformation process and contain foreign nucleic acid. The term "untransformed" refers to cells that have not been through the transformation process.

The term "transition phase" of the cell culture refers to the period of time during which culture conditions for the production phase are engaged. During the transition phase environmental factors such as pH, ion concentration, and temperature may shift from growth conditions to production conditions.

The term "seed product" includes, but is not limited to, seed fractions such as de-hulled whole seed, flour (seed that has been de-hulled by milling and ground into a powder) a seed extract, preferably a protein extract (where the protein fraction of the flour has been separated from the carbohydrate fraction), malt (including malt extract or malt syrup) and/or a purified protein fraction derived from the transgenic grain.

"Seed maturation" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

The term "sequence similarity" refers to the degree of identity or correspondence between nucleic acid or amino acid sequences that may or may not share a common evolutionary origin (see Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, for example, the GCG (Genetics Computer Group, Version 7, Madison, Ws.) pileup program, or using any of the programs and algorithms described above. The program may use the local homology algorithm of Smith and Waterman with the default values: Gap creation penalty=$-(1+1/k)$, k being the gap extension number, Average match=1, Average mismatch=$-0.333$.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The practice of the present invention will employ, unless otherwise indicated, conventional techniques of chemistry, molecular biology, miocrobiology, recombinant DNA and immunology, which are within the capabilities of a person of ordinary skill in the art. Such techniques are explained in the literature. Practitioners are particularly directed to Sambrook et al. (1989) *Molecular Cloning: A Laboratory Manual* (Second Edition), Cold Spring Harbor Press, Plainview, N.Y.; Ausubel F M et al. (1993); *Current Protocols in Molecular Biology*, John Wiley & Sons, New York, N.Y.; and Gelvin and Schilperoot, eds. (1997) *Plant Molecular Biology Manual*, Kluwer Academic Publishers, The Netherlands; DNA Isolation and Sequencing: Essential Techniques, John Wley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3,4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

The publications discussed above are provided solely for their disclosure before the filing date of the present application. Nothing herein is to be construed as an admission that the invention is not entitled to antedate such disclosure by virtue of prior invention.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

I. Methods of Using the Supplements of the Invention

Frequently, cell culture media is supplemented with serum at concentration of 5 to 10%. Serum is a complex mixture containing undefined essential matter for cell growth. Commonly used serum is fetal calf serum (FCS) and fetal bovine serum (FBS). Due to its complex nature, lack of consistency, and the potential risk for pathogen contamination, cell culture industries and regulatory agencies are seeking alternatives to adding serum to cell culture media.

Cell culture components and cell culture supplements added to basal media serve distinct functions in promoting cell growth. These protein components are typically animal-derived. With the increase in the concern of potential pathogen contamination from animal sourced material, cell culture industries are trying to develop animal-component-free media. While some successes have been made with the use of plant-based hydrolysates and recombinant proteins produced using microbial systems, plant-based hydrolysates are an undefined mixture of components and recombinant protein from microbial sources are too expensive to use in routine cell culture. An alternative source of non-animal-derived components would be beneficial for industries that depend on cell culture techniques.

Accordingly in one embodiment the instant invention provides a method for culturing cells, including providing a cell culture media supplemented with two or more proteins selected from the group consisting of lactoferrin, transferrin, albumin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, alpha-lactalbumin, and derivatives, fractions, and biologically-active fragments thereof; and introducing cells to be cultured into the cell culture media. The cells grown in the cell culture media exhibit improved growth characteristics as compared to cells grown in an unfortified cell culture media.

Accordingly in one embodiment the instant invention provides a method for culturing cells, including providing a cell culture media supplemented with two or more proteins selected from the group consisting of lactoferrin, transferrin, albumin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, alpha-lactalbumin, and derivatives, fractions, and biologically-active fragments thereof; and introducing cells to be cultured into the cell culture media. The cells grown in the cell culture media exhibit improved growth characteristics as compared to cells grown in an unfortified cell culture media.

According to further embodiments, the combination of proteins that is used in the methods of culturing cells and supplements of the invention provides a synergistic effect on the growth and/or productivity of the cells present in the cell culture media. According to still further embodiments, the supplements comprising one combination of proteins that may be used in the methods of culturing cells includes lactoferrin and albumin.

In another aspect, the supplements comprises a combination of transferrin related proteins and albumin which provide a synergistic effect on cell growth and productivity.

A further aspect of the invention includes methods for achieving an improved growth rate of cultured cells, and higher productivity of the cultured cells, adding a supplement of the present invention to the cell culture medium.

The claimed supplements are useful in a wide range of applications for tissue and cell culture and recombinant protein production where they provide for significant improvements in preventing apoptosis and improving cell viability during tissue culture, and in particular in response to stress.

Apoptosis involves a series of biochemical events leading to a characteristic cell morphology and death. These changes include, changes to the cell membrane such as loss of membrane asymmetry and attachment, cellular blebbing cell shrinkage, nuclear fragmentation, chromatin condensation, and chromosomal DNA fragmentation.

The process of apoptosis is controlled by a diverse range of cell signals, which may originate either extracellularly (extrinsic inducers) or intracellularly (intrinsic inducers). Extracellular signals may include toxins, hormones, growth factors, nitric oxide, cytokines, which may be present to different degrees in tissue culture media. These signals may positively (i.e., trigger) or negatively (i.e., repress, inhibit, or dampen) affect apoptosis, and thus influence overall cell viability. A number of intracellular components, including ATP content, calcium level, and a number of apoptotic and anti-apoptotic genes also help regulate apoptosis. A cell may initiate intracellular apoptotic signaling in response to a stress, which may bring about cell suicide. Stress inducing agents encountered during tissue culture include for example toxins, associated with tissue culture components such as endotoxins, and heavy metals that leach from plastic ware, transfection reagents (e.g. Lipofectamine and similar lipid based transfection reagents), viral transformation, nutrient and growth factor deprivation, associated with serum free culture, or cell differentiation protocols hypoxia and oxidative stress associated with high density culture in a bioreactor and increased intracellular calcium concentration, for example, by damage to the membrane caused by detergents and electroporation.

Before the actual process of cell death occurs, the apoptotic signals must overcome regulatory proteins which act as gatekeepers overseeing the activation of the apoptosis pathway. In vivo, this step allows the process to be stopped, should the cell no longer need to die. Several proteins are involved at this step, though two main mechanisms of regulation have been identified and include those associated with mitochondria functionality, and those directly involved in transducing the signal via adaptor proteins to the apoptotic mechanisms.

Cells grown under cell culture conditions may experience cellular stresses associated with routine tissue culture procedures, as described above which may trigger apoptotic signals and increase the susceptibility of the cells to apoptosis. For example, nutrient deprivation associated with serum free culture, oxidative stress associated with high density growth in a bioreactor, the use of cytotoxic compounds associated with DNA transfection reagents, and thermal stresses associated with cryopreservation, may predispose the cell to enter apoptosis. By enhancing the ability of a cell to survive such signals it is possible to improve cell viability during these procedures, by preventing the cells commitment to cell death, thereby improving the success and utility of these approaches.

Recently a number of genes in eukaryotic cells have been identified which inhibit the onset or reduce the effects of apoptosis. Some of these genes inhibit caspase dependent apoptotic pathways in the cell, and in fact transfecting cells with anti-apoptotic genes may be useful in prolonging the life and productivity of transfected cells grown under biologically demanding conditions. (U.S. Pat. Nos. 6,586,206; 7,531,327; US Patent Application US 2009/0170165; US2009/0181426).

Additionally the addition of exogenous heat shock proteins has in some cases been shown to improve the survival of cells in culture under a variety of conditions. (Novoselova et al., J. Neurochem. 94 597-606 (2005); Tidwell et al., Cell Stress & Chap 9 (1) 88-90 (2004); Guzhova et al., Cell Stress & Chap. 3 (1) 67-77 (1998); Hounenou et al., Cell Stress & Chap 1 (3) 161-166 (1996); Johnson et al., In vitro Cell. Dev. Biol., 29A 807-812 (1993).

The present invention is based in part on the demonstration that plant derived recombinant cell culture component proteins surprisingly enhanced the cell growth and viability when added in specific mixtures to mammalian cells grown in culture. Surprisingly some combinations of proteins provide for a synergistic effect on cell growth and productivity which provides unexpected benefits compared to the use of the individual proteins. Specifically, such supplements comprising plant derived recombinant albumin and transferrin related proteins result in improved culture viability, extended cell survival, improved rates of cell growth and improved yields of recombinant proteins produced from tissue culture bioreactors. Because the supplements show unexpectedly improved activity and stability they offer significant improvements compared to the use of standard recombinant or purified proteins.

The supplements disclosed in the present application are useful, for example, for improving cell viability and in accelerating the rate of cell growth of cells grown in culture. In one aspect, the supplements of the invention are useful for improving or enhancing the yield of the recombinant proteins from the cell cultures. Further improvements provided by the invention are described in detail below.

In one embodiment, the present invention includes a method for enhancing cell growth of a cell in culture comprising the addition of a supplement to the cell culture medium.

In one embodiment, the present invention includes a method for enhancing the productivity of a cell that has been adapted to serum free media comprising the addition of a supplement to the serum free media.

In one embodiment, the present invention includes a method for reducing the accumulation of lactate in a bioreactor comprising the addition of a supplement to cells in culture in the bioreactor.

In one embodiment, the present invention includes a method or reducing the consumption of glucose and other sugars in a bioreactor comprising the addition of a supplement to cells in culture in the bioreactor.

In one embodiment, the present invention includes a method of reducing time required to produce protein from start of culture to harvest in a bioreactor comprising the addition of a supplement to cells in culture in the bioreactor.

In one embodiment, the present invention includes a method for improving the viability of cells in a bioreactor comprising the addition of a supplement to the bioreactor.

In one embodiment, the present invention includes a method for improving the viability of cells grown under serum free conditions comprising the addition of a supplement to the serum free medium.

In one embodiment, the present invention includes a method for improving the viability of cells when plated at low density comprising the addition of a supplement to the cell culture medium.

In one embodiment, the present invention includes a method for improving the viability of cells grown from single cell clones comprising the addition of a supplement to the cell culture medium.

In one embodiment, the present invention includes a method for improving the viability of primary cells grown in culture comprising the addition of a supplement to the culture medium.

In one embodiment, the present invention includes a method for improving the viability of cells after transfection comprising the addition of a supplement to the cell culture medium prior to, during, or immediately after transfection.

In one embodiment, the present invention includes a method for improving the viability of cell after cryopreservation comprising the addition of a supplement to the cell culture medium prior to, during, or immediately after cryopreservation or thawing.

In one embodiment, the present invention includes a method for improving the rate of cell growth or viability of stem cells grown in culture comprising the addition of a supplement of the present invention to the cell culture media.

In one embodiment, the present invention includes a method for improving the yield of a recombinant product produced from cells in culture comprising the addition of a supplement of the present invention to the cell culture media during one or more of the growth phase, transition phase, or production phase of the culture.

In one embodiment, the present invention includes a method for improving the purification of a recombinant product produced from cells in culture, comprising the addition of a supplement to the culture media during one or more of the growth phase, transition phase, or production phase of the culture.

In one embodiment, the present invention includes a method for reducing the proteolysis of a recombinant product produced from cells in culture, comprising the addition of a supplement to the culture media during one or more of the growth phase, transition phase, or production phase of the culture.

In one embodiment, the present invention includes a method for improving the bioactivity of a recombinant product produced from cells in culture, comprising the addition of a supplement to the culture media during one or more of the growth phase, transition phase, or production phase of the culture.

In one embodiment, the present invention includes a method for improving the stability of a recombinant product produced from cells in culture, comprising the addition of a supplement to the culture media during one or more of the growth phase, transition phase, or production phase of the culture.

In one embodiment, the present invention includes a method for improving the assembly of a recombinant product produced from cells in culture, comprising the addition of a supplement to the culture media during one or more of the growth phase, transition phase, or production phase of the culture.

In one embodiment, the present invention includes a method for creating a more human pattern of glycosylation of a recombinant product produced from cells in culture, comprising the addition of a supplement to the culture media during one or more of the growth phase, transition phase, or production phase of the culture.

In one embodiment, the present invention includes a method for creating a recombinant product produced from cells in culture with less immunogenicity, comprising the addition of a supplement comprising recombinant albumin to the culture media during one or more of the growth phase, transition phase, or production phase of the culture.

In any of these methods, the supplements of the invention, by increasing host cell viability in culture (and during fermentation), provide for a simple and cost effective method to increase the yield, and or purity, bioactivity, stability and assembly of functional recombinant protein. Additionally, the supplements of the invention, by decreasing or inhibiting apoptosis in the cell culture, can decrease the number or presence of adverse proteases in the culture media and protect the expressed protein of interest against proteolytic degradation, thereby increasing the quality of the protein of interest produced, as evidenced by increased amounts of active protein, and increased yields of intact protein. Additionally Applicants have found that the supplements of the invention may protect the cells against potential adverse effects of agents like detergents, heavy metals and endotoxin contaminates present in the culture components, or protect the cells from toxic reagents introduced to the cells during transfection or cryopreservation.

In any of the claimed methods, the supplements of the invention can be added directly, or admixed, to the culture media at any convenient time, for example when changing the media, passaging the cells, or when plating out the cells at low density. Optionally, the supplement is added to the culture media at the beginning (at the time of initiating, day 0) of the cell culturing process. In one aspect the supplements of the invention may be added before an anticipated stressful event, for example before cryopreservation, transfection or serum withdrawal, etc.

In another aspect, the supplement is added to the culture media during the culturing of the cells prior to the point when induction of typically apoptosis occurs. For example, during a large scale cell culture, induction of apoptosis can be observed on about day 3 or day 4 of the culture, and therefore, the supplement will preferably be added prior to day 3 or day 4. Optionally, a desired quantity of the supplement is added throughout, or for the duration of, the cell culture, for instance, on a daily basis for the entire fermentation. As an example, for a 5 day culture, the supplement could be added at day 0, and every 24 hours thereafter until the culture is terminated.

Accordingly in one embodiment, the invention provides a method of improving the yield and quality of a recombinant protein produced in a bioreactor by adding a supplement of the invention to the bioreactor. In one embodiment, the bioreactor comprises bacterial cells. In another aspect the bioreactor comprises yeast cells. In another aspect the bioreactor comprises plant cells. In another aspect the bioreactor comprises mammalian cells.

In another embodiment, the invention provides a method of improving the yield and quality of a recombinant protein produced in bacterial cells, by adding the supplement of the invention to the cell culture. In another embodiment, the invention provides a method of improving the yield and quality of a recombinant protein produced in yeast cells by adding the supplement of the invention to the cell culture. In another embodiment, the invention provides a method of improving the yield and quality of a recombinant protein produced in a plant cells by adding the supplement of the invention to the cell culture. In another embodiment, the invention provides a method of improving the yield and quality of a recombinant protein produced in insect cells by adding the supplement of the invention to the cell culture. In another embodiment, the invention provides a method of improving the yield and quality of a recombinant protein produced in mammalian cells by adding the supplement of the invention to the cell culture.

In another embodiment, the invention provides a method to increase the yield of the production phase of a cell culture system and thereby increase the productivity of a bioreactor by adding the supplement of the invention to the cell culture system prior to, or during the production phase of the cell culture system.

In one aspect of this method the yield of the production phase is increased by about 10%. In one aspect of this method the yield of the production phase is increased by about 20%. In one aspect of this method the yield of the production phase is increased by about 30%. In one aspect of this method the yield of the production phase is increased by about 40%. In one aspect of this method the yield of the production phase is increased by about 50%. In one aspect of this method the yield of the production phase is increased by about 60%. In one aspect of this method the yield of the production phase is increased by about 70%. In one aspect of this method the yield of the production phase is increased by about 80%. In one aspect of this method the yield of the production phase is increased by about 90%. In one aspect of this method the yield of the production phase is increased by about 100%. In one aspect of this method the yield of the production phase is increased by about 200%. In one aspect of this method the yield of the production phase is increased by about 500%.

In one aspect of any of these methods, the yield is increased compared to a control cell culture system to which the supplement was not added. In one aspect of any of these methods, the yield is increased compared to a control cell culture system to which is added a supplement lacking either a transferrin related protein, or recombinant serum albumin. In one aspect, the yield is increased compared to the summed effect of the recombinant albumin and the transferrin related protein when added alone when measured under the same culture conditions.

In another embodiment, the invention provides a method to produce a protein of interest at a temperature that is elevated compared to normal growth conditions for the production of that protein, comprising the addition of a supplement of the invention to cells expressing the protein of interest.

In another embodiment, the invention provides a method to decrease the amount of aggregates formed in a cell culture expression system by aggregate prone proteins of interest comprising the addition of a supplement of the invention to the cell culture expression system, whereby the aggregation state of the protein is reduced.

In another embodiment, the invention provides a method to increase the activity of a protein of interest protein expressed by a cell by preventing the denaturation and aggregation of the recombinant protein comprising the addition of a supplement of the invention to the cell, whereby the specific activity of the protein of interest is increased.

In another embodiment, the invention provides a method to improve the expression of proteins in a cell culture expression system that are aggregation prone, cause precipitation to occur, or are toxic themselves to the cells comprising the addition of a supplement of the invention to the cell culture expression system, whereby the expression of the protein of interest is increased.

The amount of supplement to add in any of these methods will depend on various factors, for instance, the type of host cell, the cell density, protein of interest and culture conditions, etc. Determining the desired concentration of supplement to be added to the culture media is within the skill in the art and can be ascertained empirically by routine optimization and without undue experimentation.

The skilled artisan will readily appreciate that different cell types will have different magnitudes of responses to the supplement of the invention, and this will be determined, to some degree, by the amount or type of the proteins in the supplement. Additionally different densities of cells will require appropriate adjustment in the total amount of supplement as well as the concentration of the individual proteins added to the culture to account for the increased cell number. Additionally cells grown in suspension culture or via adherent culture will have different membrane surface areas available for protein entry and will typically exhibit different rates and degrees of response. Therefore, one should choose a concentration which provides for a sufficient inhibition of apoptosis, or increase in viability, or net cell growth. Typically the supplements of the invention will be added to a final concentration of about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, or about 50% wt/wt, or wt/volume.

There will typically be an upper range of concentration of the supplement beyond which further increases in cell survival do not occur. As described in the Examples below, Applicants have found that the supplements of the invention can inhibit apoptosis when added to cell cultures at a concentration of about 200 mg/L to about 2 g/L, or more preferably about 200 mg/L to about 1000 mg/L, or more preferable about 250 to about 500 mg/L.

II. Supplements

The cell culture media, methods for producing supplemented cell culture media, and methods of culturing cells using fortified cell culture media in accordance with the present invention may include components derived from animal, plant, bacterial, yeast, and insect sources. According to one aspect of the invention, the components are derived from plant sources, and preferably from monocot plants. The components may be combined with inorganic salts such as NaCl, KCl, NaH$_2$PO$_4$, NaHCO$_3$, CaCl$_2$, and MgCl$_2$ and other ingredients such as amino acids, vitamins, growth factors, sugars, and antibiotics to form a variety of different cell culture media.

According to further embodiments, the proteins contained in the cell culture media are recombinant proteins, preferably recombinant human proteins. According to still further embodiments, one or more of the proteins in the cell culture media are plant-produced heterologous proteins, preferably two or more of the proteins in the cell culture media are plant-produced heterologous proteins, and more preferably all of the proteins in the cell culture media are plant-produced heterologous proteins.

According to another aspect, one of the proteins is albumin, and at least one additional protein is selected from the group consisting of growth factors, lactoferrin, transferrin, insulin, growth hormone, fibronectin attachment factor, lamin attachment factor, collagenase, platelet derived growth factor, brain-derived neurotrophic factor, glial-derived neurotrophic factor, thymic factors, haptocorin, lactahedrin, lactoperoxidase, alpha-fetoprotein, immunoglobin, alpha-lactalbumin, and derivatives, fractions, and biologically-active fragments thereof.

According to further embodiments, the combination of proteins that is used in the methods of producing the supplemented cell culture media provides a synergistic effect on the growth and/or productivity of the cells present in the cell culture media. According to still further embodiments, one combination of proteins that may be used in the methods of producing the cell culture media includes a combination of albumin with at least one other protein selected from the group consisting of lactoferrin, transferrin, melanotransferrin, and ovotransferin.

In one aspect the supplements of the invention comprise plant derived recombinant human serum albumin.

The term "albumin", refers to all naturally-occurring and synthetic forms of albumin. Preferably, the term "albumin" refers to recombinant albumin. In one aspect the albumin is from a vertebrate.

In one aspect the albumin is from a mammal. In a further embodiment the albumin is human. In another aspect, the recombinant albumin is produced from a plant cell. In one particularly preferred embodiment the recombinant albumin is produced from transgenic rice (*Oryza sativa*). Representative species and Gene bank accession numbers for various species of albumin are listed below in Table D1.

TABLE D1

| Exemplary Albumin genes | |
|---|---|
| Species | Gene Bank Accession number |
| Human | NP_000468.1 |
| *Pan troglodytes* | XP_517233.2 |
| *Canis lupus familiaris* | XP_855557.1 |
| *Bos taurus* | NP_851335.1 |
| *Mus musculus* | NP_033784.1 |
| *Rattus norvegicus* | NP_599153.1 |
| *Gallus gallus* | NP_990592.1 |

It will be understood that for the recombinant production of albumin in different species it will typically be necessary to codon optimize the nucleic acid sequence of the gene for the host organism in question. Such codon optimization can be completed by standard analysis of the preferred codon usage for the host organism in question, and the synthesis of an optimized nucleic acid via standard DNA synthesis. A number of companies provide such services on a fee for services basis and include for example, DNA2.0, (CA, USA) and Operon Technologies. (CA, USA).

The albumin may be in its native form, i.e., as different allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the albumin, are also specifically included in any of the methods of the invention including for example, pyroglutamyl, iso-aspartyl, proteolytic, phosphorylated, glycosylated, reduced, oxidatized, isomerized, and deaminated variants of the albumin.

Fragments of native or synthetic albumin sequences may also have the desirable functional properties of the peptide from which they derived and may be used in any of the methods of the invention. The term "fragment" as used herein thus includes fragments of albumin provided that the fragment retains the biological or therapeutically beneficial activity of the whole molecule.

For example, albumin contains at least 2 high affinity multi-metal binding sites for a number of physiologically important metals ions including copper, zinc, cadmium and nickel. (Carter et al., Advances in Protein Chemistry 45 153-203 (1994); Bai et al., J. Inorg Biochem 70 (1) 33-39 (1998), Blindauer et al., J. Biol. Chem. 284 (34) 23116-24 (2009); U.S. Pat. No. 6,787,636). Since trace amounts of these metals are typically present in the recombinant production of albumin, a significant amount of these metal ions can be become chelated to the protein. The binding of these ions, and in particular the binding of cadmium and nickel to recombinant albumin is associated with cellular toxicity of the protein when added to cells as a tissue culture component.

Accordingly, in one aspect, the albumin of the present invention can comprise a fragment of albumin that includes the deletion of one or amino acids involved in the multimetal binding sites of albumin. In one aspect the albumin fragment is created by the deletion of one or more amino acids at the N-terminus of the mature protein. In another aspect the albumin can comprise one or more deletions or mutations of any of the amino acids involved in the N-terminal metal binding site of albumin. In one aspect, the amino acids to be deleted or mutated are independently selected from the first 10 amino acids of the mature protein.

The term "derivative" as used herein thus refers to albumin sequences or fragments thereof, which have modifications as compared to the native sequence. Such modifications may be one or more amino acid deletions, additions, insertions and/or substitutions. These may be contiguous or non-contiguous. Representative variants may include those having 1 to 20, or more preferably 1 to 15, 1 to 10, or 1 to 5 amino acid substitutions, insertions, and/or deletions as compared to any of genes listed in Tables D1. The substituted amino acid may be any amino acid, particularly one of the well-known 20 conventional amino acids (Ala (A); Cys (C); Asp (D); Glu (E); Phe (F); Gly (G); His (H); Ile (I); Lys (K); Leu (L); Met (M); Asn (N); Pro (P); Gin (Q); Arg (R); Ser (S); Thr (T); Val (V); Trp (W); and Tyr (Y)). Any such variant or derivative of albumin may be used in any of the methods of the invention.

Accordingly, the albumin of the invention can comprise amino acid deletions, insertions or mutations in any of the functional binding domains of albumin. In one aspect the albumin may comprise a mutation in a binding domain of albumin. In one aspect the mutated binding domain is a domain involved in the binding of aspirin, warfarin, diazepam, digitoxin, dlofibrate, ibuprofen or AZT, as outlined is U.S. Pat. No. 5,780,593, or a multimetal binding site as outlined in Blindauer et al., J. Biol. Chem. 284 (34) 23116-24 (2009).

Thus, the albumin which may be used in any of the methods of the invention may have amino acid sequences which are substantially homologous, or substantially similar to the native albumin amino acid sequences, for example, to any of the native albumin gene sequences listed in Table D1. Alternatively, the albumin may have an amino acid sequence having at least 30% preferably at least 40, 50, 60, 70, 75, 80, 85, 90, 95, 98, or 99% identity with albumin listed in Table D1. In a preferred embodiment, the albumin for use in any of the methods of the present invention is at least 80% identical to the mature secreted human serum albumin (SEQ. ID. No. 1) as shown below (Swiss-Prot P02768):

```
MKWVTFISLL FLFSSAYSRG VFRRDAHKSE VAHRFKDLGE

ENFKALVLIA FAQYLQQCPF EDHVKLVNEV TEFAKTCVAD

ESAENCDKSL HTLFGDKLCT VATLRETYGE MADCCAKQEP

ERNECFLQHK DDNPNLPRLV RPEVDVMCTA FHDNEETFLK

KYLYEIARRH PYFYAPELLF FAKRYKAAFT ECCQAADKAA

CLLPKLDELR DEGKASSAKQ RLKCASLQKF GERAFKAWAV

ARLSQRFPKA EFAEVSKLVT DLTKVHTECC HGDLLECADD

RADLAKYICE NQDSISSKLK ECCEKPLLEK SHCIAEVEND

EMPADLPSLA ADFVESKDVC KNYAEAKDVF LGMFLYEYAR

RHPDYSVVLL LRLAKTYETT LEKCCAAADP HECYAKVFDE

FKPLVEEPQN LIKQNCELFE QLGEYKFQNA LLVRYTKKVP

QVSTPTLVEV SRNLGKVGSK CCKHPEAKRM PCAEDYLSVV

LNQLCVLHEK TPVSDRVTKC CTESLVNRRP CFSALEVDET

YVPKEFNAET FTFHADICTL SEKERQIKKQ TALVELVKHK

PKATKEQLKA VMDDFAAFVE KCCKADDKET CFAEEGKKLV

AASQAALGL
```

Fusion proteins of albumin to other proteins are also included, and these fusion proteins may enhance, activity, targeting, stability or potency.

Chemical modifications of the native albumin structure which retain or stabilize albumin activity or biological half-life may also be used with any of the methods described herein. Such chemical modification strategies include without limitation pegylation, glycosylation, and acylation (see Clark et al.: J. Biol. Chem. 271(36): 21969-21977, 1996; Roberts et al.: Adv. Drug. Deliv. Rev. 54(4): 459-476, (2002); Felix et al.: Int. J. Pept. Protein. Res. 46(3-4): 253-264, (1995); Garber Diabetes Obes. Metab. 7 (6) 666-74 (2005)) C- and N-terminal protecting groups and peptomimetic units may also be included.

Isomers of the native L-amino acids, e.g., D-amino acids may be incorporated in any of the above forms of albumin, and used in any of the methods of the invention. All such variants, derivatives, fusion proteins, or fragments of albumin are included, may be used in any of the methods claims or disclosed herein, and are subsumed under the term "albumin".

In one aspect of the supplements of the invention the albumin is recombinant human serum albumin that has been produced in a plant. In another aspect, the albumin comprises less than about 2% aggregated albumin. In another aspect the albumin comprises less than about 1% aggregated albumin.

In one embodiment, the supplements of the invention comprise preparations of the co-purified recombinant albumin and rice hsps that are also essentially free of detergents and endotoxins which would otherwise mask or inhibit the positive impact of the hsp. In one aspect the supplements of the invention have less than about 1 EU of endotoxin, and the albumin is at least about 95% pure. In another aspect the supplements of the invention comprise a composition comprising recombinant albumin bound to a heat shock protein. In another aspect the supplements of the invention comprise recombinant albumin and a rice hsp70 homolog. In one aspect the rice hsp70 homolog is selected from HSP70, Bip and rice stromal protein.

The terms "heat shock protein", "HSP" or "hsp", as used herein includes all naturally-occurring and synthetic forms of the heat shock protein super family that retain anti-apoptotic activity. Such heat shock proteins include the small heat shock proteins/HSPB family, Hsp40/DnaJ family, HSP70/HSPA family, HSP90/HSPC family, HSP110/HSPH family and chapererone family, as well as peptide fragments and protein complexes of two or more heat shock proteins or nucleotide exchange factors (for example, complexes of HSP70 & HSP40) derived therefrom. The heat shock proteins may be in their native form, i.e., as different variants as they appear in nature in different species which may be viewed as functionally equivalent variants, or they may be functionally equivalent natural derivatives thereof, which may differ in their amino acid sequence, for example, by truncation (e.g., from the N- or C-terminus or both) or other amino acid deletions, additions, insertions, substitutions, or post-translational modifications. Naturally-occurring chemical derivatives, including post-translational modifications and degradation products of the HSPs, are also specifically included in any of the methods of the invention including for example, pyroglutamyl, iso-aspartyl, proteolytic, phosphorylated, glycosylated, oxidatized, isomerized, and deaminated variants of the HSP.

The term "transferrin related protein" refers to transferrin family proteins including transferrin, lactoferrin, melano-transferrin, and ovotransferin. The crystal structures of transferrin family members across all species that have been solved to date show a high degree of structural similarity, which is not surprising since transferrin, lactoferrin and ovotransferrin share 60-80% sequence identity. (Wally and Buchanan, Biometals (2007) 20 249-262). All transferrin related proteins contain two domains of around 340 residues, which are thought to have evolved from an ancient duplication event. For serum transferrin, ovotransferrin and lactoferrin each of the duplicated lobes binds one atom of Fe (III) and one carbonate anion. With a few notable exceptions each iron atom is coordinated to four conserved amino acid residues: an aspartic acid, two tyrosines, and a histidine, while anion binding is associated with an arginine and a threonine in close proximity. (Anderson et al., (1989) J. Mol. Biol. 209 711-734).

Human transferrin and lactoferrin share over 61% sequence identity and have similar three dimensional structures. Transferrins transport iron in the blood by picking up free ferric iron and delivering it to cells in a receptor-mediated endocytotic process in which the TF-receptor complex is internalized, iron is released in the endosome, and the complex is recycled to the cell surface where the TF is released. In contrast, no iron transport role for lactoferrin or ovotransferrin is known. By comparison, these proteins are thought to function to prevent invading bacteria from acquiring iron, by sequestering all available iron. Human transferrin releases iron at a higher pH than does human lactoferrin which likely relates to the need for human transferrin to release iron after endocytosis into the endosome, and the need for lactoferrin to hold onto iron in low pH environments such as the stomach (Baker & Backer (2004) Biometals 17 209-216).

The term "transferrin" refers to all naturally-occurring and synthetic forms of transferrin. In one aspect, the term "transferrin" refers to recombinant transferrin. In one aspect, the term "transferrin" refers to plasma derived transferrin. In one aspect the transferrin is from a vertebrate. In one aspect the transferrin is from a mammal. In a further embodiment the transferrin is human. In another aspect the recombinant transferrin is produced from a plant cell. In one particularly preferred embodiment the recombinant transferrin is produced from transgenic rice (*Oryza sativa*). Representative species and Gene bank accession numbers for various species of transferrin are listed below in Table D2.

TABLE D2

Exemplary Transferrin genes

| Species | Gene Bank Accession number |
| --- | --- |
| Homo sapiens | NP_001054.1 |
| Canis lupus familiaris | XP_864550.1 |
| Bos taurus | NP_803450.2 |
| Mus musculus | NP_598738.1 |
| Rattus norvegicus | NP_001013128.1 |
| Gallus gallus | NP_990635.1 |
| Danio rerio | NP_001015057.1 |

The transferrin may be in its native form, i.e., as different apo forms, or allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the transferrin are also specifically included in any of the methods of the invention including for example, pyroglutamyl, iso-aspartyl, proteolytic, phosphorylated, glycosylated, reduced, oxidatized, isomerized, and deaminated variants of the transferrin.

The transferrin which may be used in any of the methods of the invention may have amino acid sequences which are substantially homologous, or substantially similar to the native transferrin amino acid sequences, for example, to any of the native transferrin gene sequences listed in Table D2. Alternatively, the transferrin may have an amino acid sequence having at least 30% preferably at least 40, 50, 60, 70, 75, 80, 85, 90, 95, 98, or 99% identity with transferrin listed in Table D2. In a preferred embodiment, the transferrin for use in any of the methods of the present invention is at least 80% identical to the mature human transferrin.

The term "Lactoferrin" refers to all naturally-occurring and synthetic forms of Lactoferrin. In one aspect, the term "Lactoferrin" refers to recombinant Lactoferrin. In one aspect, the term "Lactoferrin" refers to milk derived Lactoferrin. In one aspect the Lactoferrin is from a vertebrate.

In one aspect the Lactoferrin is from a mammal. In a further embodiment the Lactoferrin is human. In another aspect the recombinant Lactoferrin is produced from a plant cell. In one particularly preferred embodiment the recombinant Lactoferrin is produced from transgenic rice (*Oryza sativa*). Representative species and Gene bank accession numbers for various species of Lactoferrin are listed below in Table D3.

TABLE D3

Exemplary Lactoferrin genes

| Species | Gene Bank Accession number |
| --- | --- |
| *Homo sapiens* | AAA59511.1 |
| *Sus scrofa* | AAA31059.1 |
| *Camelus dromedarius* | CAB53387.1 |
| *Bos taurus* | AAA30610.1 |
| *Equus caballus* | CAA09407.1 |

The Lactoferrin may be in its native form, i.e., as different apo forms, or allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of Lactoferrin are also specifically included in any of the methods of the invention including for example, pyroglutamyl, iso-aspartyl, proteolytic, phosphorylated, glycosylated, reduced, oxidatized, isomerized, and deaminated variants of Lactoferrin. Lactoferrin which may be used in any of the methods of the invention may have amino acid sequences which are substantially homologous, or substantially similar to the native Lactoferrin amino acid sequences, for example, to any of the native Lactoferrin gene sequences listed in Table D3. Alternatively, the Lactoferrin may have an amino acid sequence having at least 30% preferably at least 40, 50, 60, 70, 75, 80, 85, 90, 95, 98, or 99% identity with Lactoferrin listed in Table D3. In a preferred embodiment, the Lactoferrin for use in any of the methods of the present invention is at least 80% identical to the mature human Lactoferrin.

The term "melanotransferrin" refers to all naturally-occurring and synthetic forms of melanotransferrin. In one aspect, the term "melanotransferrin" refers to recombinant melanotransferrin. In one aspect, the term "melanotransferrin" refers to melanotransferrin purified from a cell or tissue. In one aspect the melanotransferrin is from a vertebrate. In one aspect the melanotransferrin is from a mammal. In a further embodiment the melanotransferrin is human. In another aspect the recombinant melanotransferrin is produced from a plant cell. In one particularly preferred embodiment the recombinant melanotransferrin is produced from transgenic rice (*Oryza sativa*). Representative species and Gene bank accession numbers for various species of melanotransferrin are listed below in Table D4.

TABLE D4

Exemplary melanotransferrin genes

| Species | Gene Bank Accession number |
| --- | --- |
| *Homo sapiens* | AAA59992.1 |
| *Oryctolagus cuniculus* | NP_001075461.1 |
| *Mus musculus* | NP_038928.1 |
| *Canis lupus familiaris* | XP_545158.2 |
| *Gallus gallus* | CAA63003.1 |

The term "ovotransferrin" refers to all naturally-occurring and synthetic forms of ovotransferin. In one aspect, the term "ovotransferrin" refers to recombinant ovotransferrin. In one aspect the ovotransferin is from a vertebrate. In one aspect the ovotransferin is from an avian. In another aspect the recombinant ovotransferrin is produced from a plant cell. In one particularly preferred embodiment the recombinant ovotransferrin is produced from transgenic rice (*Oryza sativa*). Representative species and Gene bank accession numbers for various species of ovotransferrin include CAA26040.1.

The term "insulin related growth factor" or "IGF-1" refers to all naturally-occurring and synthetic forms of insulin related growth factor, including IGF-1, IGF-1A, IGF-1B, IGF-2A, and IGF-2B. In one aspect, the term "insulin related growth factor" refers to recombinant insulin related growth factor. In one aspect, the term "insulin related growth factor" refers to insulin related growth factor purified from a cell or tissue. In one aspect the insulin related growth factor is from a vertebrate. In one aspect the insulin related growth factor is from a mammal. In a further embodiment the insulin related growth factor is human. In another aspect the recombinant insulin related growth factor is produced from a plant cell. In one particularly preferred embodiment the recombinant insulin related growth factor is produced from transgenic rice (*Oryza sativa*). Representative species and Gene bank accession numbers for various species of insulin related growth factor are listed below in Table D5.

TABLE D5

Exemplary insulin related growth factor genes

| Species | Gene Bank Accession number |
| --- | --- |
| *Homo sapiens* | P01343 |
| | P05019 |
| | CAA01954.1 |
| | CAA40093.1 |
| | CAA40092.1 |
| *Bos taurus* | NP_001071296 |
| *Mus musculus* | NP_001104746.1 |
| | NP_034642.2 |
| | NP_908941.1 |
| | NP_001104745.1 |
| | NP_001104744.1 |
| *Xenopus laevis* (African clawed frog) | Q90WW4 |
| *Danio rerio* (zebrafish) | NP_571900 |

The insulin related growth factor may be in its native form, i.e., as different apo forms, or allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of insulin related growth factor, are also specifically included in any of the methods of the invention including for example, pyroglutamyl, iso-aspartyl, proteolytic, phosphorylated, glycosylated, reduced, oxidatized, isomerized, and deaminated variants of insulin related growth factor. Insulin related growth factor which may be used in any of the methods of the invention may have amino acid sequences which are substantially homologous, or substantially similar to the native insulin related growth factor amino acid sequences, for example, to any of the native insulin related growth factor gene sequences listed in Table D5. Alternatively, the insulin related growth factor may have an amino acid sequence having at least 30% preferably at least 40, 50, 60, 70, 75, 80, 85, 90, 95, 98, or 99% identity with insulin related growth factor listed in Table D5. In a preferred embodiment, the insulin related growth factor for use in any of the methods of the present invention is at least 80% identical to the mature human insulin related growth factor.

In one aspect the supplements comprise a mixture of lactoferrin and recombinant albumin mixed in a ratio of lactoferrin to albumin of about 1 to 5, about 1 to 10, about 1 to 15, about 1 to 20 or about 1 to 25. In one aspect of any of these supplements, the concentration of lactoferrin in the culture is about 0.1 to about 0.5 g/L, In one aspect the supplement exhibits at least a 30% increase in productivity compared to the additive effect of each cell culture component alone when added to the culture at the same concentration and measured under the same culture conditions as the combination of tissue culture components.

In one aspect the supplements comprise a mixture of lactoferrin and recombinant albumin mixed in a ratio of lactoferrin to albumin of about 1 to 1 about 1 to 2, about 1 to 3, about 1 to 4 or about 1 to 5. In one aspect of any of these supplements, the concentration of lactoferrin in the culture is about 0.5 to 0.8 g/L. In one aspect the supplement exhibits at least a 30% increase in productivity compared to the additive effect of each cell culture component alone when added to the culture at the same concentration and measured under the same culture conditions as the combination of tissue culture components.

In one aspect the supplements comprise a mixture of lactoferrin and recombinant albumin mixed in a ratio of lactoferrin to albumin of about 1 to 0.5 about 1 to 0.75, about 1 to 1.0 about 1 to 1.25, about 1 to 1.5, about 1 to 1.75 or about 1 to 2.0. In one aspect of any of these supplements, the concentration of lactoferrin in the culture is about 0.8 to 1.5 g/L. In one aspect the supplement exhibits at least a 30% increase in productivity compared to the additive effect of each cell culture component alone when added to the culture at the same concentration and measured under the same culture conditions as the combination of tissue culture components.

In one aspect the supplements comprise a mixture of lactoferrin and recombinant albumin mixed in a ratio of lactoferrin to albumin of about 1 to 0.25 about 1 to 0.33, about 1 to 0.66 about 1 to 1.00, about 1 to 1.33, about 1 to 1.66 or about 1 to 2.0. In one aspect of any of these supplements, the concentration of lactoferrin in the culture is about 1.0 to about 1.5 g/L. In one aspect the supplement exhibits at least a 30% increase in productivity compared to the additive effect of each cell culture component alone when added to the culture at the same concentration and measured under the same culture conditions as the combination of tissue culture components.

In one aspect the supplements comprise a mixture of lactoferrin and recombinant albumin mixed in a ratio of lactoferrin to albumin of about 1 to 0.8, about 1 to 1 or about 1 to 1.2. In one aspect of any of these supplements, the concentration of lactoferrin in the culture is about 0.1 to about 1.5 g/L. In one aspect the supplement exhibits at least a 50% increase in productivity compared to the additive effect of each cell culture component alone when added to the culture at the same concentration and measured under the same culture conditions as the combination of tissue culture components.

In one aspect the supplements comprise a mixture of transferrin and recombinant albumin mixed in a ratio of transferrin to albumin of about 1 to 20, about 1 to 100, or about 1 to 200. In one aspect of any of these supplements, the concentration of transferrin in the culture is about 1 to about 10 ug/L. In one aspect the supplement exhibits at least a 50% increase in productivity compared to the additive effect of each cell culture component alone when added to the culture at the same concentration and measured under the same culture conditions as the combination of tissue culture components.

In one aspect the supplements comprise a mixture of transferrin and recombinant albumin mixed in a ratio of transferrin to albumin of about 1 to 500, about 1 to 1000, or about 1 to 2000. In one aspect of any of these supplements, the concentration of transferrin in the culture is about 1 to about 10 ug/L. In one aspect the supplement exhibits at least a 50% increase in productivity compared to the additive effect of each cell culture component alone when added to the culture at the same concentration and measured under the same culture conditions as the combination of tissue culture components.

In one aspect the supplements comprise a mixture of transferrin and recombinant albumin mixed in a ratio of transferrin to albumin of about 1 to 3000, about 1 to 4000, or about 1 to 5000. In one aspect of any of these supplements, the concentration of transferrin in the culture is about 1 to about 10 ug/L. In one aspect the supplement exhibits at least a 50% increase in productivity compared to the additive effect of each cell culture component alone when added to the culture at the same concentration and measured under the same culture conditions as the combination of tissue culture components.

In one aspect the supplements comprise a mixture of transferrin and albumin mixed in a ratio of transferrin to albumin of about 1 to 80, about 1 to 100 or about 1 to 120. In one aspect of any of these supplements, the concentration of transferrin in the culture is about 3 to about 8 u g/L. In one aspect the supplement exhibits at least an 80% increase in productivity compared to the additive effect of each cell culture component alone when added to the culture at the same concentration and measured under the same culture conditions as the combination of tissue culture components.

In one aspect the supplements comprise a mixture of IGF-1 and recombinant albumin mixed in a ratio of IGF-1 to albumin of about 1 to 100000, about 1 to 10000, or about 1 to 1000. In one aspect of any of these supplements, the concentration of IGF-1 in the culture is about 1 to about 10 ug/L. In one aspect the supplement exhibits at least a 50% increase in productivity compared to the additive effect of each cell culture component alone when added to the culture at the same concentration and measured under the same culture conditions as the combination of tissue culture components.

In another aspect of the invention, the supplements contain one or more additional factors selected from the group consisting of a growth factor, sodium selenate and ethanolamine.

In another aspect of the invention, the growth factors are independently selected from insulin, Epidermal Growth Factor (EGF), Fibroblast Growth Factors 1-23 (FGF), Insulin-like Growth Factor-1(IGF), keratinocyte growth factors 1 & 2(KGF), and Leukemia Inhibitory Factor (LIF). In one aspect the growth factor is insulin. In another aspect the growth factor is transferrin.

In one aspect, the supplements of the invention may be prepared by mixing the isolated cell culture components in aqueous solution.

Liquids of known concentration can also be combined containing one component part A (albumin or another cell culture component), to a liquid containing part B (such as a transferrin related protein or IGF-1) to obtain a ratio that contains the desired ratios of the components Powdered, lyophilized, or otherwise dried powder (albumin) can be added directly to an aqueous solution containing the cell culture component (such as transferrin related protein) in order to obtain a ratio based on dry weight of albumin at any desired range with respect to the other cell culture components. Powdered, lyophilized, or otherwise dried albumin can also be blended with the cell culture component powder on a mass to mass basis to obtain a ratio that is completely based on gravimetrics. The resulting powder can be dissolved at concentrations ranging from very low (picomolar) to very high concentrations (millimolar) in suitable buffers that are common to the art to reconstitute the cell culture components.

In one aspect, supplements of the present invention will accordingly comprise recombinant albumin and one or more transferrin related proteins and/or IGF-1. Such supplements will commonly be prepared as sterile liquid or powder form. The total amount of transferrin related protein in the composition may vary from 50% to about 0.0001% of weight of the cell culture component. In other aspects the amount of transferrin related protein in the composition may vary from about 0.01% to about 0.02%, or about 0.01% to about 0.09%, or about 0.02% to about 0.04%, or about 0.02% to about 0.06%, or about 0.02% to about 0.08%. In another aspect the amount of transferrin related protein in the composition is greater than about 0.01%, or more preferably greater than about 0.05%, or more preferably greater than about 0.1% wt/wt, or more preferably greater than about 0.2% wt/wt transferrin related protein with respect to albumin.

In one aspect of any of the claimed supplements, the recombinant albumin is essentially free of endotoxin and detergents. In another aspect the albumin has less than about 1 EU/mg of endotoxin. In yet another aspect, the albumin contains less than about 10 ppm detergent. In another aspect of any of the claimed supplements, the albumin has a purity of greater than 95%.

In another of any of the claimed supplements, the supplement comprises recombinant albumin which is bound to a rice heat shock protein, wherein the complex has less than about 1 EU of endotoxin and is at least 95% pure with respect to the albumin. In one aspect the recombinant albumin is produced in rice.

In another aspect of any of these methods the supplement contains recombinant albumin as the cell culture component, and the albumin is essentially free of aggregated albumin. In another aspect of any of these supplements the recombinant albumin has less than about 2% aggregated albumin.

In one aspect, supplements of the present invention will accordingly comprise recombinant albumin with one or more bound hsps. Such supplements will commonly be prepared as sterile liquid or powder form. The total amount of hsp in the albumin composition may vary from 5% to about 0.001% of weight of albumin. In other aspects the amount of hsp in the albumin composition may vary from about 0.01% to about 0.02%, or about 0.01% to about 0.09%, or about 0.02% to about 0.04%, or about 0.02% to about 0.06%, or about 0.02% to about 0.08%. In another aspect the amount of hsp in the albumin composition is greater than about 0.02%, or more preferably greater than about 0.03%, or more preferably greater than about 0.04% wt/wt, or more preferably greater than about 0.05% wt/wt hsp with respect to albumin.

III. Production of Cell Culture Media Components

Albumin and transferrin related proteins, as well as other cell culture media components for use in the supplements of the present invention can be prepared in any suitable manner, for instance by isolation from naturally occurring sources, from genetically engineered host cells comprising expression systems (see below), or by chemical synthesis, using, for instance, automated peptide synthesizers, or any combination of such methods. The means for preparing such polypeptides are well understood in the art.

For recombinant production, host cells can be genetically engineered to incorporate nucleic acids encoding the cell culture media component. Typically the nucleic acid will be codon optimized for high level expression in the expression system of choice, and incorporated into an expression vector to enable the expression of the protein of interest in the host cell. Vectors can exist as circular, double stranded DNA, and range in size form a few kilobases (kb) to hundreds of kb. Preferred cloning vectors have been modified from naturally occurring plasmids to facilitate the cloning and recombinant manipulation of polynucleotide sequences. Many such vectors are well known in the art and commercially available; see for example, by Sambrook (In. "Molecular Cloning: A Laboratory Manual," second edition, edited by Sambrook, Fritsch, & Maniatis, Cold Spring Harbor Laboratory, (1989)), Maniatis, In: Cell Biology: A Comprehensive Treatise, Vol. 3, Gene Sequence Expression, Academic Press, NY, pp. 563-608 (1980).

General and specific techniques for producing proteins from plant cells may be obtained from the following patents and applications, each of which is incorporated herein in its entirety by reference: U.S. Pat Pub. No. 2003/0172403 AI ("Plant Transcription Factors and Enhanced Gene Expression"); U.S. Pat. No. 6,991,824 ("Expression of Human Milk Proteins in Transgenic Plants"); U.S. Pat. Pub. No. 2003/0221223 ("Human Blood Proteins Expressed in Monocot Seeds"); U.S. Pat. Pub. No. 2004-0078851 ("Production of Human Growth Factors in Monocot Seeds"); U.S. Pat. Pub. No. 2004/0063617 ("Method of Making an Anti-infective Composition for Treating Oral Infections"); and international application no. PCT/US2004/041083 ("High-level Expression of Fusion Polypeptides in Plant Seeds Utilizing Seed-Storage Proteins as Fusion Carriers"). Other general and specific techniques for producing proteins from plant cells may be obtained, for example, from the following references, each of which is incorporated herein in its entirety by reference: U.S. Pat. Nos. 5,693,507, 5,932,479, 6,642,053, and 6,680,426 (each titled "Genetic Engineering of Plant Chloroplasts"); U.S. Pat. Pub. No. 2005/0066384 ("Site-Targeted Transformation Using Amplification Vectors"); U.S. Pat. Pub. No. 2005/0221323 ("Amplification Vectors Based on Trans-Splicing"); U.S. Pat. Pub. No. 2006/0026718 ("Method of Controlling Cellular Processes in Plants"); and U.S. Pat. Pub. No. 2006/0075524 (Method of Controlling A Cellular Process in a Multi-Cellular Organism"); Marillonnet et at., Systemic *Agrobacterium tumefaciens*-mediated transfection of viral replicons for efficient transient expression in plants, Nature Biotech. (2005) 23(6): 718-723.

Expression vectors include plasmids, episomes, cosmids retroviruses or phages; the expression vector can be used to express a DNA sequence encoding the cell culture media component, and in one aspect comprises an assembly of expression control sequences. The choice of promoter and other regulatory elements can vary according to the intended host cell, and many such elements are available commercially, and can be readily assembled from isolated components such as the Gateway system from Invitrogen, (CA, USA). Expression systems for cell culture media components can be stable or transient expression systems.

Representative commercially available viral expression vectors include, but are not limited to, the adenovirus-based systems, such as the Per.C6 system available from Crucell, Inc., lentiviral-based systems such as pLP1 from Invitrogen, and retroviral vectors such as tobacco mosaic virus based vectors (Lindbo et al., BMC Biotechnol. (2007) 7 52-58).

An episomal expression vector is able to replicate in the host cell, and persists as an extrachromosomal episome within the host cell in the presence of appropriate selective pressure. (See for example, Conese et al., Gene Therapy 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP), specific examples include the vectors pREP4, pCEP4, pREP7 from Invitrogen. The host range of EBV based vectors can be increased to virtually any eukaryotic cell type through the co-expression of EBNA1 binding protein 2 (EPB2) (Kapoor et al., EMBO. J. 20: 222-230 (2001)), vectors pcDNA3.1 from Invitrogen, and pBK-CMV from Stratagene represent non-limiting examples of an episomal vector that uses T-antigen and the SV40 origin of replication in lieu of EBNA1 and oriP.

An integrating expression vector can randomly integrate into the host cell's DNA, or can include a recombination site to enable the specific recombination between the expression vector and the host cells chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (e.g., pcDNA™5/FRT), or the cre-lox system, such as can be found in the pExchange-6 Core Vectors from Stratagene. Examples of vectors that integrate into host cell chromosomes in a random fashion include, for example, pcDNA3.1 (when introduced in the absence of T-antigen) from Invitrogen, pCI or pFN10A (ACT) Flexi® from Promega.

Alternatively, the expression vector can be used to introduce and integrate a strong promoter or enhancer sequences into a locus in the cell so as to modulate the expression of an endogenous gene of interest (Capecchi M R. Nat Rev Genet. (2005); 6 (6):507-12; Schindehutte et al., Stem Cells (2005); 23 (1):10-5). This approach can also be used to insert an inducible promoter, such as the Tet-On promoter (U.S. Pat. Nos. 5,464,758 and 5,814,618), in to the genomic DNA of the cell so as to provide inducible expression of an endogenous gene of interest. The activating construct can also include targeting sequence(s) to enable homologous or non-homologous recombination of the activating sequence into a desired locus specific for the gene of interest (see for example, Garcia-Otin & Guillou, Front Biosci. (2006) 11:1108-36). Alternatively, an inducible recombinase system, such as the Cre-ER system, can be used to activate a transgene in the presence of 4-hydroxytamoxifen (Indra et al. Nuc. Acid. Res. (1999) 27 (22): 4324-4327; Nuc. Acid. Res. (2000) 28(23): e99; and U.S. Pat. No. 7,112,715).

Suitable cells for producing the cell culture media components include prokaryotic cells, yeasts, insect cells, plant expression systems and mammalian expression systems. Within these general guidelines, useful microbial hosts include, but are not limited to, bacteria from the genera *Bacillus, Escherichia* (such as *E. coli*), *Pseudomonas, Streptomyces, Salmonella, Erwinia, Bacillus subtilis, Bacillus brevis*, the various strains of *Escherichia coli* (e.g., HB101, (ATCC NO. 33694) DH5a, DH10 and MC1061 (ATCC NO. 53338)).

Many strains of yeast are known to those skilled in the art and are also available as host cells for the expression of cell culture media components including those from the genera *Hansenula, Kluyveromyces, Pichia,* Rhino-sporidium, *Saccharomyces,* and *Schizosaccharomyces,* and other fungi. Preferred yeast cells include, for example, *Saccharomyces cerivisae* and *Pichia pastoris*.

Additionally, where desired, insect cell systems can be utilized to produce the cell culture media components for use in the supplements and methods of the present invention. Such systems are described, for example, by Kitts et al., Biotechniques, 14:810-817 (1993); Lucklow, Curr. Opin. Biotechnol., 4:564-572 (1993); and Lucklow et al. (J. Virol., 67:4566-4579 (1993). Preferred insect cells include Sf-9 and HI5 (Invitrogen, Carlsbad, Calif.).

Many suitable plant expression systems can be used for the expression of cell culture media components examples includes for example, any monocot or dicot plant. Suitable monocot plants include without limitation, rice, barley, wheat, rye, corn, millet, triticale, or sorghum, preferably rice. Other suitable plants include *Arabidopsis*, Alfalfa, tobacco, peanut and soybean.

In general, expression vectors for use in plants include the following operably linked elements that constitute a chimeric gene: a promoter derived from a gene encoding a plant protein, operatively linked to a gene encoding a cell culture media component. The promoter region is chosen to be regulated in a manner allowing for induction under seed-maturation conditions. Promoters for use in the invention are typically derived from cereals such as rice, barley, wheat, oat, rye, corn, millet, triticale or sorghum.

In one aspect, the chimeric gene includes a promoter which exhibits increased expression during seed maturation. Examples of such promoters include the maturation-specific promoter region associated with one of the following maturation-specific monocot plant storage proteins: rice glutelins, oryzins, and prolamines, barley hordeins, wheat gliadins and glutelins, maize zeins and glutelins, oat glutelins, and sorghum kafirins, millet pennisetins, and rye secalins.

In one aspect, the chimeric gene includes i) a promoter from the gene of a maturation-specific monocot plant storage protein, ii) a first DNA sequence, operably linked to the promoter, encoding a monocot plant seed-specific signal sequence (such as an N-terminal leader sequence or a C-terminal trailer sequence) capable of targeting a polypeptide linked thereto to an endosperm cell, preferably an endosperm-cell organelle, such as a protein storage body, and iii) a second DNA sequence, linked in translation frame with the first DNA sequence, encoding a cell culture media component. The signal sequence is preferably cleaved from the cell culture media component in the plant cell.

The chimeric gene, in turn, is typically placed in a suitable plant-transformation vector having (i) companion sequences upstream and/or downstream of the chimeric gene which are of plasmid or viral origin and provide necessary characteristics to the vector to permit the vector to move DNA from bacteria to the desired plant host; (ii) a selectable marker sequence; and (iii) a transcriptional termination region generally at the opposite end of the vector from the transcription initiation regulatory region. Numerous types of appropriate expression vectors, and suitable regulatory sequences are known in the art for a variety of plant host cells.

At least one selective purification tag and/or at least one specific protease cleavage site may be provided for eventual release of the cell culture media component from the monocot seed storage protein carrier. For example, a strategic methionine or tryptophan residue providing a chemical cleavage site may be engineered in frame between the domains for release of the cell culture media component from the endogenous plant protein. Other selective protease cleavage sites include, but are not limited to enterokinase (ek), Factor Xa, thrombin, V8 protease, GENENASE™ (a variant of subtilisin BPN'), α-lytic protease or tobacco etch virus protease. Alternatively, cleavage of the fusion protein could be performed via chemical cleaving agents such as cyanogen bromide or N-chlorosuccinimide.

A number of suitable mammalian host cells are also known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines.

Cell-free transcription and translation systems can also be employed to produce such proteins using the DNA constructs (or RNAs derived from the DNA constructs) of the present invention.

Production of recombinant proteins of the present invention may be prepared by processes well known in the art from genetically engineered host cells comprising expression systems. Accordingly, in a further aspect, the present invention relates to expression systems comprising a polynucleotide or polynucleotides encoding the cell culture media component and to host cells which are genetically engineered with such expression systems and to the production of such proteins by recombinant techniques. In one embodiment the host cell endogenously expresses a heat shock protein of interest.

In cases where purification of the expressed proteins of the supplement of the invention are necessary, proteins of the present invention can be recovered from either the cellular environment, before lysing the cells, or after cell lysis. The proteins can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. High performance liquid chromatography is also employed for purification.

A search of patents, published patent applications, and related publications will provide those skilled in the art reading this disclosure with significant possible methods for preparing and purifying albumin. For example, U.S. Pat. Nos. 4,075,197; 4,086,222; 4,093,612; 4,097,473; 4,136,094; 4,228,154; 5,250,662; 5,656,729; 5,677,424; 5,710,253; 5,728,553; 5,994,507; 6,001,974; 6,638,740; 6,617,133 and 7,423,124 disclose various processes for purifying albumin. In one aspect, the albumin for use in the present invention is purified using any of these art recognized processes listed above, and then mixed in aqueous solution with a heat shock protein. Methods for the purification of heat shock proteins, including anion exchange chromatography and ATP agarose affinity chromatography are well known in the art. (Welch & Feramisco, J. Biol. Chem. 257 (24)14949-14959; (1982); Welch & Feramisco, Mol. Cell. Biol. 5 (6) 1229-1237 (1985). Well known techniques for refolding proteins may be employed to regenerate active conformation when the polypeptide is denatured during intracellular synthesis, isolation and/or purification.

In one preferred aspect recombinant albumin is purified using procedures that enable the direct co-purification of both recombinant albumin and a heat shock protein, or hsp protein complex, for example as described below and in the Examples section. In one aspect the recombinant albumin is produced in rice, and the heat shock protein is an endogenous rice heat shock protein.

In one aspect, of this method, expression vectors are used to increase the expression of the recombinant albumin in the host cell, while the expression of the host cells endogenous heat shock proteins is accomplished by activating the expression of the host cells hsp genes. In another aspect expression vectors are used to increase the expression of the heat shock protein. In another aspect expression vectors are used to increase the expression of the heat shock protein and albumin. In another aspect the nucleic acid sequence encoding a heat shock protein and albumin are located in the same expression vector.

Due to the similar electronegativity of albumin and hsp70, anion exchange chromatography is the preferred method to prepare albumin enriched in Hsps. For example, both albumin and Hsp70 bind to anion exchange columns with resins consisting of either quaternary amine or diethylaminoethyl mounted on a bead that is suitable for the ion exchange of polypeptides (large molecular exclusion limit and of suitable size) at high pH (7.5 and above). Examples of such resins are General Electric (GE) Q Sepharose and GE DEAE Sepharose. Due to their similar electronegativity, utilizing low pH conditions (below pH 6.5) allows for the co-purification of the two molecules on cation exchangers as well. Examples of such cation exchangers are GE Carboxymethyl Sepharose and Sulfonic acid Sepharose based resins. Because the albumin and Hsp70 have similar isoelectric points, mixed mode resins may also be employed for the co-purification of albumin and Hsp70. Since both Hsp70 and Albumin are well known to bind to fatty acids and other hydrophobic molecules, it is also possible to co-purify albumin and Hsp70 on a hydrophobic based resin such as octyl sepharose (GE). Due the similar size of Hsp70 proteins and Albumin (65-75 kDa), co-purification of the two proteins and enrichment of Hsp70 by tangential flow ultrafiltration utilizing both higher and lower molecular exclusions than 65-75 kDa may also be employed to co-purify and thus enrich Albumin with hsps.

Also due to their similar molecular weights, any method that separates polypeptides based on size should effectively co-purify albumin and hsp70 such as molecular sieves and gel filtration or size exclusion chromatography. In addition, due to the similar nature of Hsp70 and Albumin in terms of hydrophobicity and electronegativity or surface charge may be co-purified by precipitation under a number of conditions. Some of those conditions are precipitation by ammonium sulfate, precipitation by denaturants such as urea, or precipitation based on isoelectric point and solubility.

The methods are also applicable to enrich albumin with hsps from other sources. For example albumin derived from native and transgenic animal feedstock serum, as well as albumin produced from recombinant organisms and tissue culture systems based on prokaryotic and eukaryotic cells, including, vertebrate cells such as mammalian cells, and non vertebrate cells, such as insects, as well as plant, and fungi such as yeast, and the like.

A search of patents, published patent applications, and related publications will also provide those skilled in the art reading this disclosure with significant possible methods for preparing and purifying transferrin related proteins. For example, U.S. Pat. Nos. 7,368,141; 7,354,902; 5,708,149; 5,596,082; 5,169,936; 4,791,193; and 4,667,018 disclose various processes for purifying transferrin related proteins.

IV Exemplary Cells

Without wishing to be bound by theory, it is contemplated that any cell which is susceptible to apoptosis may be used in the methods of the invention, including primary cells, immortalized cells, differentiated cells, undifferentiated cells or cells, such as stem cells, with varying degrees of specialization. In a particular embodiment, cells used in the methods of the invention are transfected with a nucleic acid molecule comprising a nucleotide sequence encoding a protein of interest, e.g., a therapeutic protein or an antibody.

In a particular embodiment, the cells used in the methods of the invention are eukaryotic cells, e.g., mammalian cells. Examples of mammalian cells include, but are not limited to, for example, human B-cells, and T cells, and derivatives thereof, such as hybridomas, and cell expressing markers of B or T cells, monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/-DHFR (CHO, Urlaub and Chasin, Proc. Natl. Acad. Sci. USA, 77:4216 (1980)); CHO-K1 cell (ATCC CCL-61), human PER.C6 cells (Crucell, NV); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; NSO mouse myeloma cells (ECACC; SIGMA), and a human hepatoma line (Hep G2). Additional examples of useful cell lines include, but are not limited to, HT1080 cells (ATCC CCL 121), MCF-7 breast cancer cells (ATCC BTH 22), K-562 leukemia cells (ATCC CCL 243), KB carcinoma cells (ATCC CCL 17), 2780AD ovarian carcinoma cells (see Van der Blick, A. M. et al., Cancer Res. 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. These and other cells and cell lines are available commercially, for example from the American Type Culture Collection (Virginia, USA). Many other cell lines are known in the art and will be familiar to the ordinarily skilled artisan; such cell lines therefore can be used equally well in the methods of the present invention. In a particular embodiment, cells used in the methods of the invention are CHO cells or NSO cells. Hybridomas and antibody-producing cells may also be used in the methods of the invention.

In another embodiment, cells used in any of the methods of the invention are stem cells. Stem cells are undifferentiated cells defined by their ability at the single cell level to both self-renew and differentiate to produce progeny cells, including self renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Types of human embryonic stem cells that may be used in any of the methods of the invention include established lines of human embryonic cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.). In one embodiment, Human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Additionally, hybridoma cells can also be used in the methods of the invention. The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line which produces antibodies such as, for example, quadromas. See, e.g., Milstein et al., Nature, 537:3053 (1983). The hybrid cell lines can be of any species, including human, rabbit and mouse.

In some embodiments, a cell line used in the methods of the invention is an antibody-producing cell line. Antibody-producing cell lines may be selected and cultured using techniques well known to the skilled artisan. See, e.g., Current Protocols in Immunology, Coligan et al., Eds., Green Publishing Associates and Wiley-Interscience, John Wiley and Sons, New York (1991) which is herein incorporated by reference in its entirety, including supplements. In general, any cell suitable for recombinant protein expression in cell culture can be used in the methods of the invention.

In some embodiments, the cells used in the methods of the present invention may include a heterologous nucleic acid molecule which encodes a desired recombinant protein, e.g., a therapeutic protein or antibody which is desired to be produced using the methods of the invention. In a particular embodiment, the methods of the present invention are useful for producing high titers of a desired recombinant protein, e.g., a therapeutic protein or antibody, in the presence of reduced levels of one or more contaminants.

V. Cell Culture Media

Any suitable culture medium or feed medium suitable for cell growth and protein production may be used in the methods of the invention. Suitable culture or feed mediums are chosen for their compatibility with the host cells and process of interest. Suitable culture or feed mediums are well known in the art and include, but are not limited to, commercial media such as Ham's F10 (SIGMA), Minimal Essential Medium (SIGMA), RPMI-1640 (SIGMA), and Dulbecco's Modified Eagle's Medium SIGMA) are suitable for culturing the animal cells. In addition, any of the media described in Ham and Wallace, (1979) Meth. Enz., 58:44; Barnes and Sato, (1980) Anal. Biochem., 102:255; U.S. Pat. Nos. 4,767,704; 4,657,866; 4,927,762; 5,122,469 or 4,560,655; International Publication Nos. WO 90/03430; and WO 87/00195 may be used.

Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. The necessary growth factors for a particular cell are readily determined empirically without undue experimentation, as described for example in Mammalian Cell Culture (Mather, J. P. ed., Plenum Press, N.Y. (1984), and Barnes and Sato, Cell, 22:649 (1980).

Other methods, vectors, and host cells suitable for adaptation to the synthesis of the protein of interest in recombinant vertebrate cell culture are described in Gething et al., Nature, 293:620-625 (1981); Mantei et al., Nature, 281:40-46 (1979); EP 117,060; and EP 117,058. In general, principles, protocols, and practical techniques for maximizing the productivity of mammalian cell cultures can be found in Mammalian Cell Biotechnology: A Practical Approach, M. Butler, ed. (IRL Press, 1991).

VI. Exemplary Cell Culture Expression Products

In one aspect of any of the claimed methods, the supplements of the invention are used to improve the viability and growth of a cell which is used to express and produce a protein of interest. The cell may express the protein of interest endogenously or may be an engineered cell line that has been modified genetically to express the protein of interest at levels above background for that cell.

Cells may be genetically modified to express a protein by transformation with a nucleic acid encoding the protein of interest, or by transformation of an activating sequence that promotes the expression of an endogenous gene. In one aspect the protein of interest may be expressed from an expression vector, in which a coding sequence for the protein of interest is operably linked to an expression control sequences, to enable either constitutive or inducible expression, as is known in the art.

The protein of interest may be any protein, or fragment thereof, which is of commercial, therapeutic or diagnostic value including without limitation cytokines, chemokines, hormones, antibodies, anti-oxidant molecules, engineered immunoglobulin-like molecules, a single chain antibodies, a humanized antibodies, fusion proteins, enzymes, immune co-stimulatory molecules, immunomodulatory molecules, transdominant negative mutants of a target protein, toxins, conditional toxins, antigens, a tumor suppresser proteins, growth factors, membrane proteins, vasoactive proteins and peptides, anti-viral proteins and ribozymes, and derivatives thereof (such as with an associated reporter group). The protein of interest may also comprise pro-drug activating enzymes.

In some embodiments, the protein of interest comprises a glycoprotein, or any other protein which has one or more post-translational modifications. For example, any protein which is suitable for production in a eukaryotic host may be expressed using the methods and compositions described here.

The methods of the invention can be used to produce any desired recombinant protein or fragment thereof. In some embodiments, a recombinant protein produced using the methods described herein is a therapeutic protein. In other embodiments, the recombinant protein is an antibody or functional fragment thereof. Antibodies which may be produced using the methods of the invention include, for example, polyclonal, monoclonal, monospecific, polyspecific, fully human, humanized, single-chain, chimeric, hybrid, CDR grafted. It may comprise a full length IgG1 antibody or an antigen-binding fragments thereof, such as, for example, Fab, F(ab')$_2$, Fv, and scfv. Antibodies within the scope of the present invention include, but are not limited to: anti-HER2 antibodies including Trastuzumab (HERCEPTIN™) (Carter et al., Proc. Natl. Acad. Sci. USA, 89:4285-4289 (1992), U.S. Pat. No. 5,725,856); anti-CD20 antibodies such as chimeric anti-CD20 "C2B8" as in U.S. Pat. No. 5,736,137 (RITUXAN™), a chimeric or humanized variant of the 2H7 antibody as in U.S. Pat. No. 5,721,108, B1, or Tositumomab (BEXXAR™.); anti-IL-8 (St John et al., Chest, 103:932 (1993), and International Publication No. WO 95/23865); anti-VEGF antibodies including humanized and/or affinity matured anti-VEGF antibodies such as the humanized anti-VEGF antibody huA4.6.1 AVASTIN™ (Kim et al., Growth Factors, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., Transplant Intl. 4:3-7 (1991), and Hourmant et al., Transplantation 58:377-380 (1994)); anti-IgE (Presta et al., J. Immunol. 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-alpha, antibodies including cA2 (REMICADE™), CDP571 and MAK-195 (See, U.S. Pat. No. 5,672,347 issued Sep. 30, 1997, Lorenz et al. J. Immunol. 156(4):1646-1653 (1996), and Dhainaut et al. Crit. Care Med. 23(9):1461-1469 (1995)); anti-Tissue Factor (TF) (European Patent No. 0 420 937 B1 granted Nov. 9, 1994); anti-human alpha 4 beta 7 integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT™) and (ZENAPAX™) (See U.S. Pat. No. 5,693,762 issued Dec. 2, 1997); anti-CD4 antibodies such as the cM-7412 antibody (Choy et al. Arthritis Rheum 39(1): 52-56 (1996)); anti-CD52 antibodies such as CAMPATH- 1H (Riechmann et al. Nature 332:323-337 (1988)); anti-Fc receptor antibodies such as the M22 antibody directed against Fc gamma RI as in Graziano et al. J. Immunol. 155(10):4996-5002 (1995); anti-carcinoembryonic antigen (CEA) antibodies such as hMN-14 (Sharkey et al. Cancer Res. 55(23Suppl): 5935s-5945s (1995); antibodies directed against breast epithelial cells including huBrE-3, hu-Mc 3 and CHL6 (Ceriani et al. Cancer Res. 55(23): 5852s-5856s (1995); and Richman et al. Cancer Res. 55(23 Supp): 5916s-5920s (1995)); antibodies that bind to colon carcinoma cells such as C242 (Litton et al. Eur J. Immunol. 26(1):1-9 (1996)); anti-CD38 antibodies, e.g. AT 13/5 (Ellis et al. J. Immunol. 155(2):925-937 (1995)); anti-CD33 antibodies such as Hu M195 (Jurcic et al. Cancer Res 55(23 Suppl):5908s-5910s (1995) and CMA-676 or CDP771; anti-CD22 antibodies such as LL2 or LymphoCide (Juweid et al. Cancer Res 55(23 Suppl):5899s-5907s (1995)); anti-EpCAM antibodies such as 17-1A (PANOREX™); anti-GpIIb/IIIa antibodies such as abciximab or c7E3 Fab (REOPRO™ anti-RSV antibodies such as MEDI-493 (SYNAGIS™); anti-CMV antibodies such as PROTOVIR™; anti-HIV antibodies such as PRO542; anti-hepatitis antibodies such as the anti-Hep B antibody OSTAVIR™; anti-CA 125 antibody OvaRex; anti-idiotypic GD3 epitope antibody BEC2; anti-.alpha.v.beta.3 antibody VITAXIN™; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

The recombinant protein may be a cellular protein such as a receptor (e.g., membrane bound or cytosolic) or a structural protein (e.g. a cytoskeleton protein). The recombinant protein may be cellular factor secreted by the cell or used internally in one or more signal transduction pathways. Non limiting examples include, but are not limited to, CD2, CD3, CD4, CD8, CD11a, CD14, CD18, CD20, CD22, CD23, CD25, CD33, CD40, CD44, CD52, CD80 (B7.1), CD86 (B7.2), CD147, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF, EGF receptor, VEGF receptor, hepatocyte growth factor, osteoprotegerin ligand, interferon gamma, B lymphocyte stimulator C5 complement TAG-72, integrin alpha 4 beta 7, the integrin VLA-4, B2 integrins, TRAIL receptors 1, 2, 3, and 4, RANK, RANK ligand, TNF, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2, and CTLA4 (which is a cytotoxic T lymphocyte-associated antigen).

The recombinant protein may also be derived from an infectious agent such as a virus, a bacteria, or fungus. The protein may be derived from a bacterial membrane or cell wall, or may be derived from the bacterial cytosol. The protein may be a bacterial or yeast enzyme, transcription factor, or structural protein. The bacterial or yeast protein may be membrane bound, cytsolic, or secreted. Examples of infectious agents include, but are not limited to, *Streptococcus mutans*, and *Staphlycoccus aureus*, and *Candida albicans*.

The methods of the invention can also be used to produce recombinant fusion proteins comprising all or part of any of the above-mentioned proteins. For example, recombinant fusion proteins comprising one of the above-mentioned proteins plus a multimerization domain, such as a leucine zipper, a coiled coil, an Fc portion of an antibody, or a substantially similar protein, can be produced using the methods of the invention. See e.g. International Application No. WO 94/10308; Lovejoy et al. (1993), Science 259:1288-1293; Harbury et al. (1993), Science 262: 1401-05; Harbury et al. (1994), Nature 371:80-83; Hang.kansson et al. (1999), Structure 7:255-64.

Also encompassed by this invention are pharmaceutical compositions including one or more recombinant proteins produced by the methods described herein. In some embodiments, pharmaceutical compositions further include a pharmaceutically acceptable carrier. The term "pharmaceutically-acceptable carrier" as used herein means one or more compatible solid or liquid filler, diluents or encapsulating substances which are suitable for administration into a subject.

VII Stem Cells

In one embodiment, human embryonic stem cells are cultured in a culture system that is essentially free of feeder cells, but nonetheless supports proliferation of human embryonic stem cells without undergoing substantial differentiation, comprising a supplement of the invention. The growth of human embryonic stem cells in feeder-free culture without differentiation is supported using a medium conditioned by culturing previously with another cell type and further comprising a supplement of the present invention. Alternatively, the growth of human embryonic stem cells in feeder-free culture without differentiation is supported using a chemically defined medium comprising a supplement of the present invention. Examples of feeder-free, serum free culture systems in which embryonic stem cells are maintained in unconditioned serum replacement (SR) medium supplemented with different growth factors capable of triggering embryonic stem cell self-renewal include those disclosed in US patent applications, US20050148070, US20050244962, US20050233446, U.S. Pat. No. 6,800,480, and PCT publications WO2005065354 and WO2005086845.

In an alternate embodiment, human embryonic stem cells are initially cultured with a layer of feeder cells that support the human embryonic stem cells and further comprising a supplement of the present invention. The human embryonic are then transferred to a culture system that is essentially free of feeder cells, but nonetheless supports proliferation of human embryonic stem cells without undergoing substantial differentiation and which further comprises a supplement of the present invention. In any of these approaches, the use of the supplements of the invention results in significantly enhanced rates of cell growth and improved cell viability.

Examples of conditioned media suitable for use with the supplements of the present invention are disclosed in US20020072117, U.S. Pat. No. 6,642,048, WO2005014799, and Xu et al (Stem Cells 22: 972-980, 2004). An example of a chemically defined medium suitable for use with the supplements of the present invention may be found in US20070010011.

Examples of feeder cells include feeder cells selected from the group consisting of a fibroblast cell, a MRC-5 cell, an embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, a muscle cell and an aortic endothelial cell. In a preferred embodiment, the MRC-5 cell, has ATCC Catalog Number 55-X; the transformed and has ATCC Accession Number CRL-2309; the human osteosarcoma cell has ATCC Accession Number HTB-96; and the mesenchymal cell is a human fetal palatal mesenchymal cell with ATCC Accession Number CRL-1486. In other preferred embodiments the human fibroblast cell is a skin keloid fibroblast, KEL FIB and has ATCC Accession Number CRL-1762, or is a fetal skin fibroblast cell; and the bone marrow stromal cell, HS-5, has ATCC Accession Number CRL-11882.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

In one embodiment, the human embryonic stem cells are plated onto a suitable culture substrate that is treated prior to treatment according to the methods of the present invention, with a composition comprising a supplement of the present invention. In one embodiment, the treatment is an extracellular matrix component, such as, for example, those derived from basement membrane or that may form part of adhesion molecule receptor-ligand couplings. In one embodiment, the suitable culture substrate is MATRIGEL (Becton Dickenson). MATRIGEL is a soluble preparation from Engelbreth-Holm-Swarm tumor cells that gels at room temperature to form a reconstituted basement membrane.

Other extracellular matrix components and component mixtures are suitable as an alternative and can be used with the supplements of the present invention. This may include laminin, fibronectin, proteoglycan, entactin, heparan sulfate, and the like, alone or in various combinations with a supplement of the present invention.

In another embodiment, the invention encompasses an embryonic stem cell culture, comprising a human pluripotent stem cell and a feeder-free, serum free culture system comprising a supplement of the invention. In one embodiment the invention encompasses a human pluripotent stem cell culture, comprising a human pluripotent stem cell and a feeder-free, serum free culture system comprising a supplement of the invention.

In another embodiment the invention encompasses an embryonic stem cell culture, comprising a human embryonic stem cell and a human feeder cell culture comprising a supplement of the invention. In another embodiment the invention encompasses a human pluripotent stem cell culture, comprising a human pluripotent stem cell and a human feeder cell culture comprising a supplement of the invention.

In another embodiment, the present invention provides a method for deriving a population of cells comprising cells expressing pluripotency markers, comprising the steps of:
Culturing human embryonic stem cells,
Differentiating the human embryonic stem cells into cells expressing pluripotency markers, wherein the differentiation is conducted in the presence of a supplement of the present invention.

In another embodiment, the present invention provides a method for deriving a population of cells comprising cells expressing markers, characteristic of ectodermal, endodermal or mesodermal cells, comprising the steps of: culturing pluripotency stem cells; and differentiating the pluripotency stem cells into cells expressing markers characteristic of ectodermal, endodermal or mesodermal cells, wherein the differentiation is conducted in the presence of a supplement of the present invention.

In any of these methods, the stem cells can be differentiated into cells expressing markers characteristic of an endodermal, ectodermal or mesodermal lineage by any method in the art. For example, cells expressing pluripotency markers may be differentiated into cells expressing markers characteristic of the definitive endoderm lineage according to the methods disclosed in D'Amour et al, Nature Biotechnology 23, 1534-1541 (2005), by Shinozaki et al, Development 131, 1651-1662 (2004), McLean et al., Stem Cells 25, 29-38 (2007), D'Amour et al., Nature Biotechnology 24, 1392-1401 (2006).

Cells expressing markers characteristic of the endoderm lineage may be further differentiated into cells expressing markers characteristic of the pancreatic endocrine lineage by any method in the art. For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006), wherein the differentiation is conducted in the presence of a supplement of the present invention.

In one aspect of any of these methods of differentiation, the human embryonic stem cells are cultured and differentiated on a tissue culture substrate coated with an extracellular matrix. The extracellular matrix may be a solubilized basement membrane preparation extracted from mouse sarcoma cells (which is sold by BD Biosciences under the trade name MATRIGEL). Alternatively, the extracellular matrix may be growth factor-reduced MATRIGEL. Alternatively, the extracellular matrix may be fibronectin. In an alternate embodiment, the human embryonic stem cells are cultured and differentiated on tissue culture substrate coated with human serum. In one aspect, the tissue culture substrate is coated with extracellular matrix and a supplement of the present invention.

The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M. A., et al., J. Cell. Biol. 101:1511 (1985).

In one aspect of the methods of stem cell differentiation, the culture medium should contain sufficiently low concentrations of certain factors to allow the differentiation of human embryonic stem cells to cells of endoderm, ectoderm or mesoderm lineage, such as, for example insulin and IGF (as disclosed in WO2006020919). This may be achieved by lowering the serum concentration, or alternatively, by using chemically defined media that lacks insulin and IGF. Examples of chemically defined media are disclosed in Wiles et al (Exp Cell Res. 1999 Feb. 25; 247(1): 241-8). In a preferred embodiment, of any of these methods, the culture media comprises a supplement of the present invention.

The culture medium may also contain at least one other additional factor that may enhance the formation of cells expressing markers characteristic of endoderm, mesoderm or ectoderm lineage from human embryonic stem cells. The at least one additional factor may be, for example, nicotinamide, members of TGF-β family, including TGF-β1, 2, and 3, serum albumin, members of the fibroblast growth factor family, platelet-derived growth factor-AA, and —BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine 1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof. In a preferred embodiment, of any of these methods, the culture media containing at least one additional factor listed above, further comprises a supplement of the present invention.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241). In a preferred embodiment, of any of these methods, the conditioned media further comprises a supplement of the present invention.

In another embodiment, the invention encompasses a method of using the cell or tissue of any of the aforementioned stem cells for the experimental, therapeutic and prophylactic treatment of a disease or condition in a human or animal. Preferably, the disease is selected from the group consisting of Parkinson's, Alzheimer's, Multiple Sclerosis, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer, solid tumors, and AIDS. In a preferred embodiment, the disease is Parkinson's or Alzheimer's. In a more preferred embodiment, the disease is Parkinson's.

VIII. Large Scale Production of Recombinant Proteins

In one embodiment, the supplements of the present invention can be used to produce a protein of interest by growing host cells in the presence of the supplement. In one embodiment, the cell culture is performed in a stirred tank bioreactor system and a fed batch culture procedure is employed. In another embodiment a wave disposable bioreactor is employed. In the bioreactor system, the size of the bioreactors are sufficiently large to produce the desired amount of protein of interest, such as 1,000 Liter or 12,000 Liter sizes, but are not limited to such sizes as much smaller (i.e., 2 Liter, 400 Liter) or larger (i.e., 25,000 Liter, 50,000 Liter) bioreactor vessels may be appropriate. In the preferred fed batch culture, the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process but at the termination of the culture process (in perfusion culturing, the cells are restrained in the culture by, e.g., filtration, encapsulation, anchoring to microcarriers etc. and the culture medium is continuously or intermittently introduced and removed from the culturing vessel).

Further, the cultured cells may be propagated according to any scheme or routine that may be suitable for the particular host cell and the particular production plan contemplated. Therefore, the present invention contemplates a single step or multiple step culture procedure. In a single step culture, the host cells are inoculated into a culture environment and the method steps of the instant invention are employed during a single production phase of the cell culture. Alternatively, a multi-stage culture is envisioned. In the multi-stage culture, cells may be cultivated in a number of steps or phases. For instance, cells may be grown in a first step or growth phase culture wherein cells, possibly removed from storage, are inoculated into a medium comprising a supplement of the present invention suitable for promoting growth and high viability. The cells may be maintained in the growth phase for a suitable period of time by the addition of fresh medium to the host cell culture.

According to a preferred aspect of the invention, fed batch or continuous cell culture conditions are devised to enhance growth of the mammalian cells in the growth phase of the cell culture. In the growth phase, cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 38° C. and preferably about 37° C. and a suitable $dO_2$ is between 5-90% of air saturation.

At a particular stage the cells may be used to inoculate a production phase or step of the cell culture. Alternatively, as described above, the production phase or step may be continuous with the inoculation or growth phase or step.

According to the present invention, the cell culture environment during the production phase of the cell culture is controlled. According to the steps of the presently disclosed methods, the addition of the supplements of the invention can be coordinated such that the desired content and quality of the protein of interest is achieved and maintained in the resulting cell culture fluid. In a preferred aspect, the production phase of the cell culture is preceded by a transition phase of the cell culture in which the addition of the supplements of the invention initiates the production phase of the cell culture.

In any of the above-described methods, it is contemplated that it may be desirable to include a desired amount of agent like butyrate or Trichostatin A in the cell culture medium in combination with a supplement of the invention. Various forms of butyrate and its salts are known in the art, such as butyric acid and sodium butyrate, and are publicly available from sources such as Sigma Chemical Co. Butyrate has been reported in the literature to enhance the productivity and protein expression of cell cultures [Arts et al., Biochem J., 310:171-176 (1995); Gorman et al., Nucleic Acids Res., 11:7631-7648 (1983); Krugh, Mol. Cell. Biochem. 42:65-82 (1982); Lamotte et al., Cytotechnology, 29:55-64 (1999); Chotigeat et al., Cytotechnology, 15:217-221 (1994)]. Trichostatin A (TSA) is an inhibitor of histone deacetylase and may act similarly to butyrate in enhancing the productivity and protein expression in cell cultures [Medina et al., Cancer Research, 57:3697-3707 (1997)]. Although butyrate has some positive effects on protein expression, it is also appreciated in the art that at certain concentrations, butyrate can induce apoptosis in the cultured cells and thereby decrease viability of the culture as well as viable cell density [Hague et al., Int. J. Cancer, 55:498-505 (1993); Calabresse et al., Biochim. Biophys. Res. Comm., 195:31-38 (1993); Fillipovich et al., Biochim. Biophys. Res. Comm., 198:257-265 (1994); Medina et al., Cancer Research, 57:3697-3707 (1997)]. In the methods of the present invention, a desired amount of butyrate or TSA may be added to the cell culture at the onset of the production phase and more preferably, may be added to the cell culture after a temperature shift has been implemented. Butyrate or TSA can be added in a desired amount determined empirically by those skilled in the art, but preferably, butyrate is added to the cell culture at a concentration of about 1 to about 25 mM, and more preferably, at a concentration of about 1 to about 6 mM.

Expression of the protein of interest may be measured in a sample directly, for example, by ELISA, conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe. Various labels may be employed, most commonly radioisotopes, and particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorophors or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared in any mammal. Many are commercially available.

The supplements claimed herein can also be used to increase transfection efficiency and viability of cells during transfection. Conditions and reagents used in various transfection techniques, such as Lipofectamine are relatively toxic to the cells, while electroporation can severely stress a cell. The use of higher concentrations of transfection reagents, and more extensive electroporation conditions is preferred to achieve higher transfection efficiencies. Thus the addition of the supplements of the invention prior, with, and after transfection can result in higher transfection efficiencies, and higher yields of recombinant proteins.

The supplements of the invention can be used to express proteins of interest which induce apoptosis, such as Apo-2 ligand/TRAIL or Fas ligand. The presence of the supplements of the invention may block such apoptotic activity and allow for improved expression of the protein of interest.

In addition, the methods can be used to increase the viability of cells undergoing freezing/storage/thawing procedures. During these procedures generally cells can lose viability. The presence of apoptosis inhibitors added to the cell culture media can provide for increased cell viability and aid in reducing or eliminating the variability in cell viabilities between aliquots or vials of cells.

IX. Kits

Also encompassed by the present invention are kits for promoting the viability of cells. In one embodiment, a kit according to the present invention comprises: (a) one or more reagents or devices for transfection and (b) a supplement of the present invention. In some embodiments, kits featured herein include instructions and/or promotional materials including details regarding using the transfection device, transfection agent and supplement.

In another embodiment a kit according to the present invention comprises: (a) one or more reagents or devices for freezing or thawing cells and (b) a supplement of the present invention.

In some embodiments, kits featured herein include instructions and/or promotional materials including details regarding protocols for freezing or thawing cell lines and the use of the reagents. In another embodiment a kit according to the present invention comprises: (a) one or more tissue culture products for culturing cells and (b) a supplement of the present invention. In some embodiments, kits featured herein include instructions and/or promotional materials including details regarding protocols for dilution cloning techniques and the use of the reagents in such approaches.

All publications, patents and patent applications are herein expressly incorporated by reference in their entirety to the same extent as if each individual publication, patent or patent application was specifically and indicated individually to be incorporated by reference in its entirety. The following examples illustrate but are not intended in any way to limit the scope of the invention.

EXAMPLES

Example 1: Expression of Recombinant Human Lactoferrin

A. An Expression Vector For Human Lactoferrin Expression In Transgenic Rice Complete nucleotide sequence of human mammary gland lactoferrin was codon optimized and synthesized by Operon Technologies (CA, USA). Human milk lactoferrin gene (Genbank accession number: HSU07642) was re-synthesized with codons most frequently used in translation of rice seed proteins in order to obtain optimal level of expression (FIG. 1A-1D). Although numbers of codons changed accounted for 22.46% of the entire sequence, amino acid composition remains identical to native human lactoferrin. The plasmid containing the codon-optimized gene was called Lac-ger. Lac-ger was digested with SmaI/XhoI and the fragment containing the lactoferrin gene was cloned into pAPI141 that was partially digested with NaeI and completely digested with XhoI. For expression of hLF in rice seeds, the codon-optimized gene was operably linked to the rice endosperm-specific glutelin (Gt1) promoter and NOS terminator. The resulting plasmid was designated pAPI164 (FIG. 2).

B. Production System

Rice variety Taipei 309 (*Oryza sativa, Japonica*) was selected as the production system for recombinant human lactoferrin and transgenic rice events were generated by the particle bombardment of embryogenic rice calli with the plasmid pAPI164 and a companion marker plasmid containing the hygromycin phosphotransferase gene as a selectable marker. Fully developed, fertile rice plants were obtained by this procedure.

C. High Level Protein Expression of Recombinant Human Lactoferrin in Rice Grain

Figure 3:
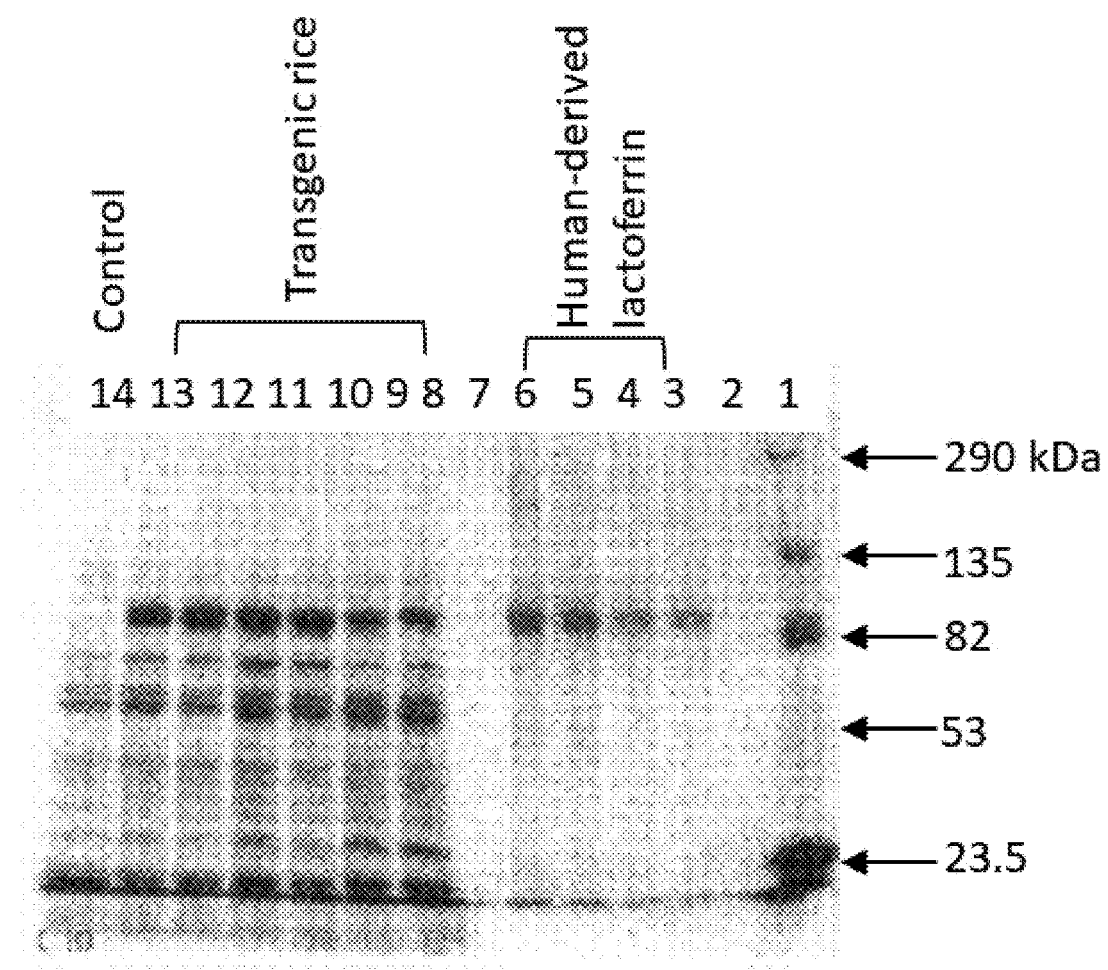
FIG. 3 shows the results of a SDS-PAGE analysis for the expression of recombinant human lactoferrin. Total proteins from rice seed extracts were suspended in Laemli sample buffer, run on a gradient gel and stained with Coomassie blue. Lane 1 is the molecular weight marker. Lanes 3 to 6 are purified human derived lactoferrin (Sigma Chemical, USA). Lanes 8 to 13 are single seed extracts from homozygous independent transgenic rice lines and lane 14 is a seed extract from non-transformed rice variety Taipei 309.
Figure 4:
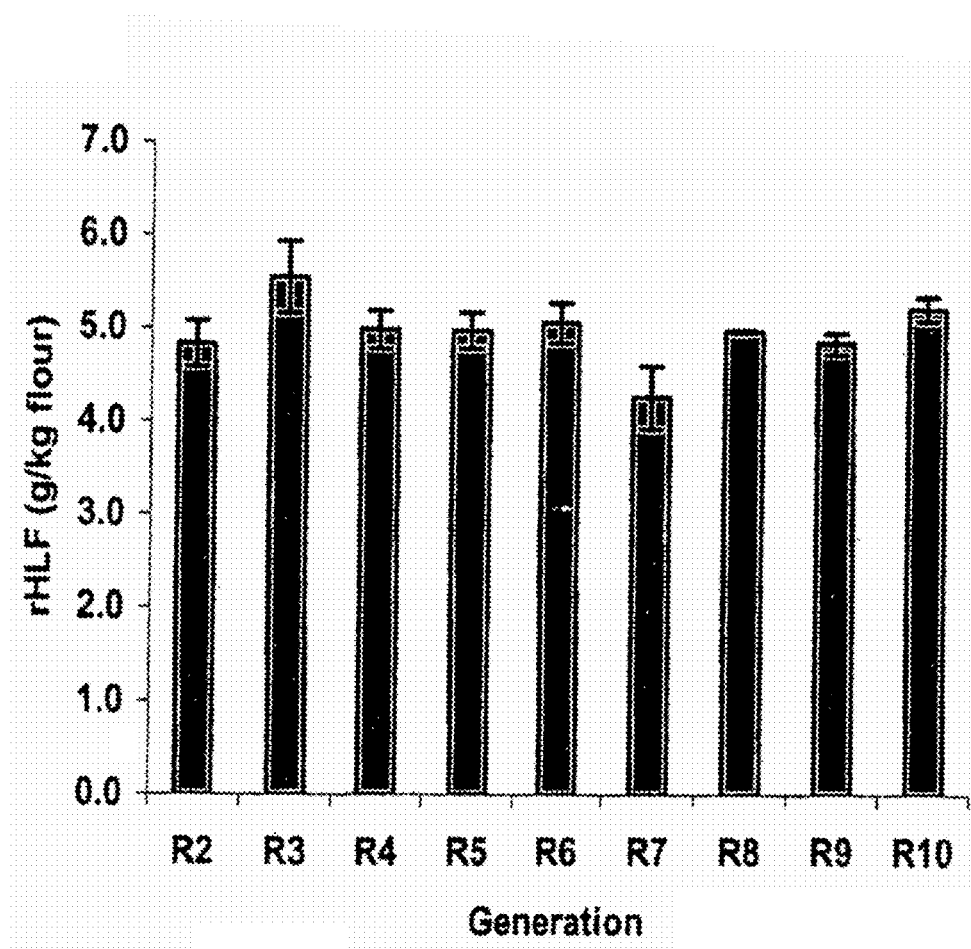
FIG. 4 is a stable expression of recombinant human lactoferrin in transgenic rice grains from $R_2$ through $R_{10}$ generations. Total soluble proteins from 1 g of brown rice flour was extracted with 40 ml of extraction buffer and clarified by centrifugation. The extract was analyzed via ELISA. Extraction was repeated three times and standard deviation is shown as an error bar.

Expression of recombinant human lactoferrin was under the control of the seed maturation-specific promoter Gt1. The high level expression of recombinant human lactoferrin is evident in FIG. 3 as independent transgenic rice events were screened. Total soluble proteins from mature rice seed extracts were run on Laemli gels and stained with Coomassie blue to visualize the proteins. An ~80 kD recombinant lactoferrin protein was obtained in all transgenic lines as indicated by the stained gel. Expression levels of recombinant human lactoferrin corresponded to 0.5% of seed weight. The stable expression of recombinant human lactoferrin was monitored for 10 generations. The expression level is maintained at approximately 0.5% of seed weight of brown rice (FIG. 4).

Example 2: Expression & Purification of Recombinant Human Transferrin

Purification of Recombinant Human from Rice Grain.

The rice grain is dehusked and milled to an average of 100 mesh flour using standard food industry procedures. Hulls and the solid material remaining after the extraction described below are destroyed. Recombinant human transferrin is extracted from the flour with extraction buffer (20 mM Tris-Base, pH 7.5), with stirring, for 40 minutes at room temperature. Filter aid (Cellpure 300) is added at 20 g/L to the extraction mixture before filtration through a filter press with 10 kDa regenerated cellulose.

The filter press filtrate was diafiltered and concentrated with a 30 KDa molecular weight cutoff cellulose membrane into 10 mM Tris-Base pH. 8.5 to prepare for DEAE chromatography. The DEAE column was washed with (20 mM Tris-Base, 40 mM Sodium Chloride, pH 7.5) prior to loading the concentrate onto the column. After loading, the column was washed with 3 volumes of 10 mM Tris-Base, 0.5% (v/v) Triton X-114, pH 8.5 buffer followed by 7 volumes of 10 mM Tris-Base, pH 8.5 buffer. Transferrin was then eluded with 20 mM Tris-Base, 40 mM Sodium Chloride, pH 7.5.

Transferrin that was recovered from the DEAE column was diafiltered and concentrated with a 10 KDa molecular weight cut off cellulose membrane into 10 mM sodium phosphate, 25 mM sodium chloride, pH 7.0 buffer. After diafiltration, recombinant transferrin was filtered though a 0.2 u filter prior to drying.

Example 3: Expression of Recombinant Human Albumin in Rice Grain

Protein sequences of human albumin (HSA) from various data bases were compared. The consensus sequence represented by accession number P02768 (Swiss-Prot) was used as a base for gene codon-optimization for suitable expression of human albumin in rice grain (FIG. 5A-FIG. 5D). Gene synthesis was carried out by Blue Heron (Seattle, Wash.) and the synthetic fragment was inserted into pUC based vector to create pUC-HSA. After confirmation of correct DNA and protein sequences, pUC-HSA was digested with Mlyl and Xhol. The fragment containing codon-optimized HSA gene was inserted into pAPI405, which had been precut with Nael and Xhol. Plasmid API405 was a derivative of pAPI141 which included Gt1 promoter, Gt1 signal sequence and a nos terminator.

Figure 6:
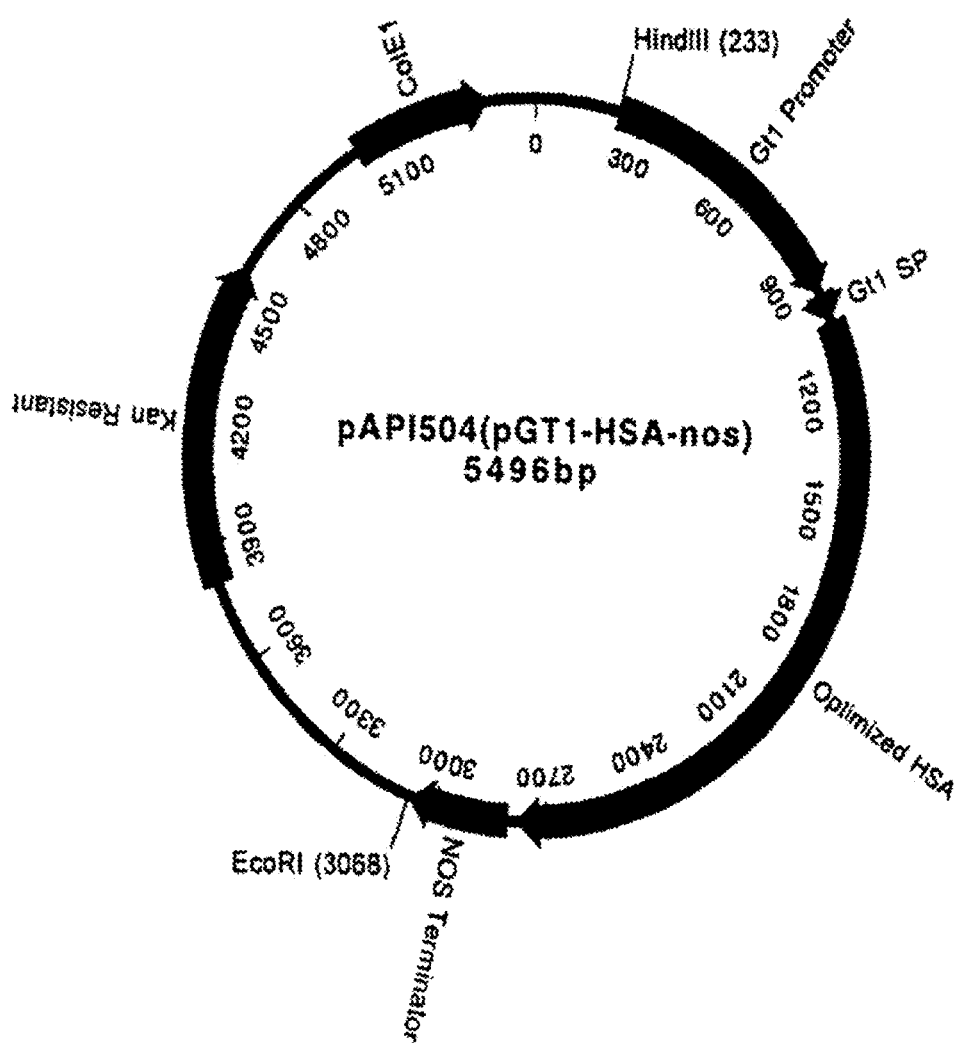
FIG. 6 is a plasmid map of the 5,496 bp plasmid, API504 (GT1-HSA), showing an expression cassette for human albumin and containing a Gt1 promoter, a Gt1 signal peptide, codon optimized human albumin, a Nos terminator and a kanamycin resistance selectable marker.
Figure 7:
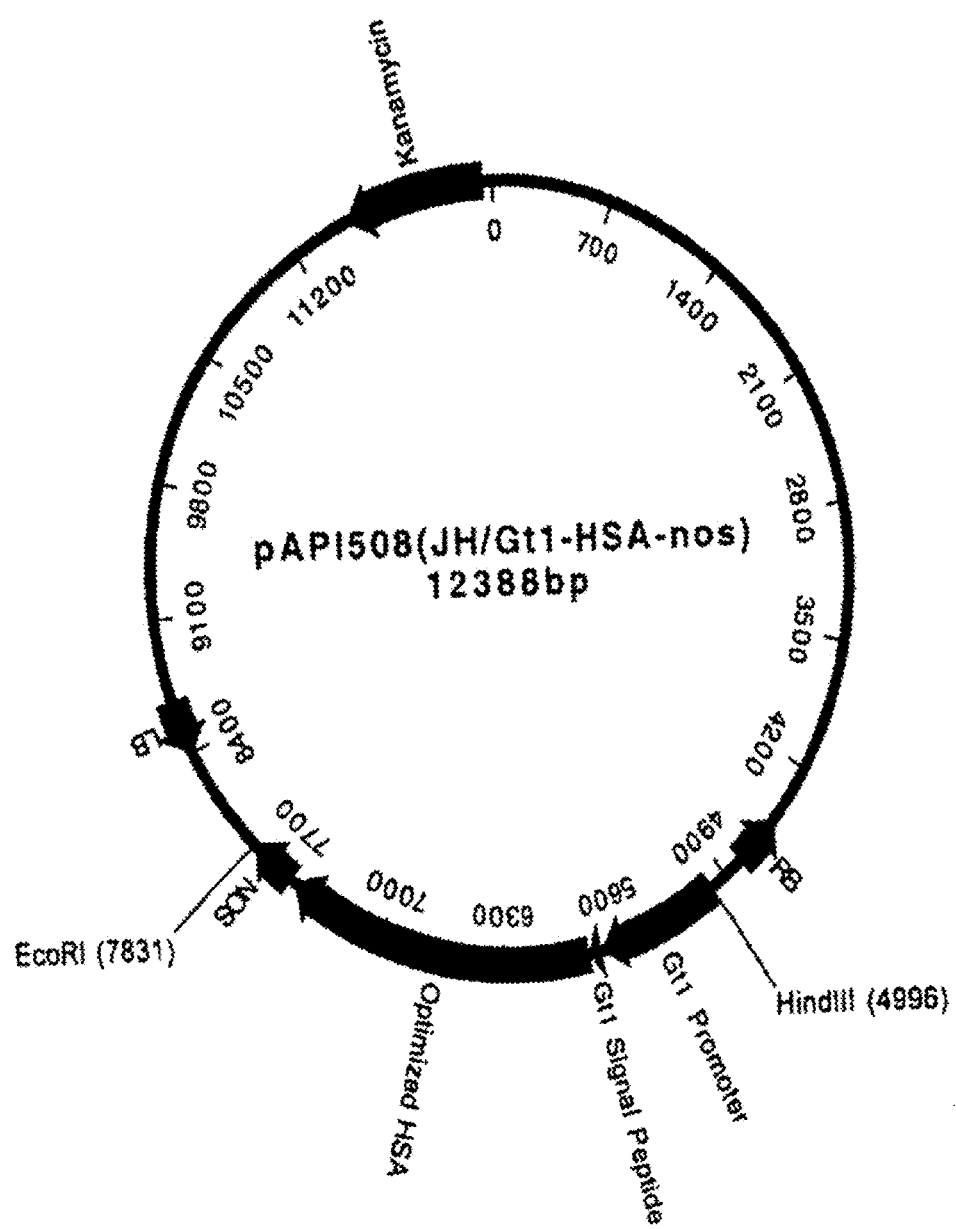
FIG. 7 is a plasmid map of the 12,388 bp plasmid, API508 (JH/GT1-HSA), showing an expression cassette for human serum albumin (HSA) and containing a Gt1 promoter, a Gt1 signal peptide, codon optimized human albumin, a Nos terminator and a kanamycin resistance selectable marker.

Insertion of Mlyl/Xhol fragment into pAPI405 resulted in pAPI504 (FIG. 6). Plasmid API504 was then cleaved with HindIII and EcoRI. The HindIII/EcoRI fragment containing the entire expression cassette, Gt1 promoter, Gt1 signal sequence, codon-optimized HSA gene and nos terminator, was cloned into pJH2600 predigested with the same enzyme resulting in pAPI508 (FIG. 7). Plasmid JH2600 was a shuttle vector between *E. coli* and *Agrobacterium*. After DNA sequence verification, pAPI508 was moved into *Agrobacterium* AGL-1 for rice transformation. Plasmid API504 was also used via bombardment-based transformation following the procedure described previously. Upon transformation, transgenic plants were generated and were sent to greenhouse where transgenic R0 plants grew to maturity and set R1 seeds.

To monitor the expression of HSA in rice seeds, 10 R1 seeds from each R0 plant were extracted using 10 mL of extraction buffer (50 mM Tris-HCl pH 8.0. 150 mM NaCl). The supernatant was collected and the expression level from rice extracts was monitored by an ELISA (Bethyl Laboratories, Montgomery, Tex.). The results showed that the HSA expression level in rice transgenic seeds ranges from 0.01 to 0.85% of brown flour weight (0.1 to 8.5 grams/kg flour). The results of the eight events with highest expression levels are shown in the following table (Table E1).

TABLE E1

Recombinant HSA expression level in top eight events

| Line Number | Express Level (g/kg flour) |
|---|---|
| 508-30 | 5.5 |
| 508-17 | 8.0 |
| 508-71 | 8.7 |
| 508-73 | 4.0 |
| 508-77 | 8.5 |
| 508-83 | 8.5 |
| 508-101 | 3.0 |
| 508-113 | 4.0 |

Example 4: Purification of Recombinant Human Lactoferrin as Cell Culture Media Component To prepare cell culture media supplemented with recombinant human lactoferrin, recombinant human lactoferrin was purified from rice flour. Transgenic rice line (164-12) expressing high levels of recombinant human LF was selected. This line, now named as LF164, was planted two generations per year, alternating field planting in summer and greenhouse planting in winter. For protein purification, paddy rice expressing rhLF was de-hulled (Rice Mill, PS-160, Rimac, FL), and then ground to flour (average particle size of 100 mesh) using a hammer mill (8WA, Schutte-Buffalo, N.Y.).

Protein extraction from transgenic flour was performed by mixing two kg of rice flour and 20 L of extraction buffer (0.02 M sodium phosphate pH 6.5 and 0.3 M sodium chloride) in a 50 L tank for 1 h. At the end of the mixing period, the suspension was allowed to settle overnight or centrifuged at 3750 rpm. In both cases, the supernatant was filtered through a plate and frame filter press (Ertel Alsop, 8S, NY) using M-05 and M-70 cellulose/perlite-based filters (Ertel Alsop, NY), respectively.

The filtrate containing rhLF and other rice flour soluble proteins was loaded onto an ion exchange column for further purification. An INDEX 200/500 process column (Amersham Pharmacia Biotech, NJ) packed with SP-Sepharose fast flow (Amersham Pharmacia Biotech, NJ) was used. The column was run at a linear flow rate of 150-200 cm/h. Packing, cleaning and testing of the resin bed was executed per manufacturer's instruction (HETP Test). The filtrate was loaded on to the resin at a linear velocity of 175 cm/h and washed with 0.02 M sodium phosphate buffer (pH 6.5) containing 0.3 M NaCl until the $A_{280}$ returned to baseline. Recombinant hLF was eluted using 20 mM sodium phosphate buffer (pH 6.5) containing 0.8 M NaCl. The washing and elution were performed at 200 cm/h and 150 cm/h, respectively.

A Centramate module (Pall Biopharmaceutical, MA) with 1 ft² 50 kDa polyethersulfone (Pall Biopharmaceutical, MA) membrane was used for concentration and desalting (ultrafiltration) of eluted hLF. The filtration was performed at a cross flow rate of approximately 1.5 L/min and an average transmembrane pressure of 10 psig. The eluted rhLF was concentrated and desalted to a final volume of 0.25 L and then lyophilized dry. Usually, about 3 grams of purified recombinant human lactoferrin was recovered from one kilogram of transgenic rice flour.

The recombinant human lactoferrin purified from rice flour is approximately 50% saturated with iron (partial-lactoferrin). The 50% saturated recombinant human lactoferrin was then made >90% iron saturated by iron up taking treatment, resulting in holo-lactoferrin and was made <10% iron saturated by acid treatment to remove bound iron resulting in apo-lactoferrin. The purified lactoferrins (holo-, partial- and apo-) were used as cell culture media components.

Example 5: Purification and Characterization of Recombinant Serum Human Albumin (rHSA)

Overview of B000 Production Process.

To purify rHSA from rice grain, rice grain expressing recombinant human serum, as described above, was dehusked, ground to flour and mixed for 30 min. with rHSA extraction buffer (Sodium Acetate, pH 4.9). After clarification by filtration, the filtrate was loaded onto an anion-exchange column (Q-Sepharose; GE Healthcare) at a rate of approximately 150 cm/hr. Once loaded, the resin was then washed with equilibration buffer to remove any unbound protein. The eluted rHSA is approximately 90% pure as analyzed by SDS-PAGE. Blue-Sepharose (GE Healthcare) can then be used to increase the purity from 90% to approximately 98% based on scanning analysis of SDS-PAGE gels. The rHSA is then concentrated and desalted via ultrafiltration prior to freeze drying.

Purified recombinant HSA was subjected to a range of biochemical and biophysical characterizations for comparison to pHSA (Plasma-derived HSA) (Table E2). These tests indicate that rHSA expressed in rice is equivalent to pHSA.

TABLE E2

Properties of recombinant albumin (rHSA) as compared to plasma derived albumin (pHSA)

| Property | pHSA | rHSA |
| --- | --- | --- |
| N-terminal sequence | DAHKSE | DAHKSE |
| Glycosylation | None | None |

TABLE E2-continued

Properties of recombinant albumin (rHSA) as compared to plasma derived albumin (pHSA)

| Property | pHSA | rHSA |
| --- | --- | --- |
| SDS-PAGE/Western | ~66 kDa | ~66 kDa |
| Molecular mass (MALDI) | 66.9-68.1 kDa | 66.8-67.9 kDa |
| Isoelectric focusing point | pI 5.3 | pI 5.3 |
| Ligand binding | Yes | Yes |
| Thermal stability | Midpoint 65° C. | Midpoint 65° C. |
| Esterase activity | Yes | Yes |
| Protease sensitivity | Same as each other | Same as each other |

B0000C Production Process: For Ventria grown rice, the rice was harvested by combine or by hand. During this process the mature seeds were separated from the vegetative plant matter by the combine separator or by manual labor. The harvested rice was dried to approximately 12% moisture at which point it is suitable for storage in a clean grain bin, storage tote, supersack, or other container that will protect the grain from birds, rodents, lizards, insects and other pests. When the rice grain is needed for flour, it is first dehusked or dehulled. This process is done under vacuum such that debris and the outer part of the seed are swept away from the endosperm and germ or bran layer. The dehusked grain is then either washed and dried, or washed and processed directly as in wet homogenization, or processed further in the dry, dehusked state. The dry, dehusked material may be debranned by a rice polishing or debranning machine which are common to white rice producers.

Debranned, dehusked rice may be washed at this point and wet-milled or dried for dry milling or processed directly by grinding into flour. Milling with the least amount of shear and heat is preferred as such with a roller mill or pin mill. A hammermill is also suitable. The flour should be ground such that the protein can be extracted to 90% in less than 5 minutes in water with hard agitation. Normally that requires a size of particle that is smaller than 400 micrometers or 4 mm. However, larger particles can be extracted if given longer time. Alternatively, the grain can be washed and wet milled with a liquid homogenizer set up such that 90% of the extractable protein is solubilized.

The flour slurry is typically mixed at a ratio of at least 3 parts water to 1 part flour and up to 20 parts water to 1 part flour. The water typically contains suitable buffers such as Tris/HCl, Citrate, Phosphate, HEPES, or the like, such that the pH is maintained around pH 7 and a small amount of salt such as 100 mM NaCl. After the slurry is homogenized in the case of wet milling, or mixed thoroughly for dry flour, the bulk solids are removed from the slurry by way of solid liquid separation. This is carried out by decanting, centrifugation, or filtration; for example using plate and frame with pads, pressure filter, belt filter, vacuum flask, hydroclone, or vacuum belt filter. After filtration, the compressed cake should be washed with extraction buffer to recover protein from the cake. The addition of diatomateous earth or other filter media is useful in promoting the clarity of the filtrate but is not necessary given the right equipment. Alternatively, a flocculating agent may be used to aid in clarification. The clarified filtrate should be checked for its albumin content and verified that the recovery is consistent with the determined expression level in the rice seed.

In order to remove starches, precipitable proteins, viruses, and other contaminants, 5 M acetic acid is added to the clarified filtrate until the pH reaches 5.0 and the solution turns white. The white solution is agitated for at least 20 minutes to encourage precipitation of insoluble materials.

The precipitated solution is then filtered through a depth filter, such as a canister filter, cartridge filter or other filtration device to reach an optical clarity that is suitable for ultrafiltration, or less that 10 NTU (nephelometry turbidity units). It can also be clarified with a filter press, pressure filter, or alternatively by using a ceramic filter or other material that utilizes cross-flow. In addition, this material is suitable for direct application to an expanded bed chromatography column.

In a preferred method, the clarified filtrate is clarified via filtration through a 0.2 micron filter, and neutralized to pH 7.0 with 1M NaOH. This material is then suitable for ultrafiltration by hollow fiber, flat sheet, or spiral wound cross flow filtration. The material can be passed through a membrane of 100 kilodalton (kDa) size or larger to remove viruses, unwanted larger contaminants, and aggregates. The material that passes through the membrane can be concentrated by a 10 or 30 kDa crossflow membrane and then the same membrane can be used to prepare the solution for chromatography. The concentrated material can then diafiltered with column equilibration buffer until the conductivity and the pH are equalized.

The preferred buffer for anion exchange chromatography on GE DEAE sepharose or GE Q sepharose is 10 or 20 mM Tris/HCl buffer pH balanced to pH 8.0. In contrast, the preferred buffer for cation exchange, for example via the use of for negatively charged resins or negatively charged resins mixed with a hydrophobic linker (mixed mode absorbents), or alternatively blue Cibicron such Blue Sepharose (GE) is acetate or citrate buffer pH balanced to 4.8 to 5.0.

For either system the albumin and other similarly charged proteins will be retained by the matrix and washing is conducted to remove loosely bound material by washing with at least 5 column volumes of loading buffer, which may also include detergents as deemed necessary to help remove hydrophobic impurities. The material can be eluted by charging the column with the same or modified buffers with the pH increased 2-4 units for cation exchange or decreased 2-4 units for anion exchange. The resulting change in pH will allow for the exchange of ions and the protein will be eluted in a sharp band. To increase the purity of the elution fraction, the elution peak can be scrutinized such that the first portion (10%) or last (10%) or both portions can be excluded from the main elution peak. In the preferred method, a solution containing phosphate at 100 mM and pH adjusted to pH 4.0 including 10 mM NaCl is used to elute the protein from GE Q sepharose (Fast Flow). In this instance, pH and conductivity are used to elute the material allowing the discrimination between non-binding contaminants (flow through and wash) and tighter binding contaminants (those that are retained on the column in 100 mM Phosphate, 10 mM NaCl, and pH adjusted to 4.0).

After elution, if the pH of the eluted material has a pH of less than 6.0, then it is neutralized with 1M NaOH. The resulting solution is then diafiltered against the same buffer for the next chromatography step, which in a preferred method involves flowing the elutent through a column of the same matrix (i.e. Q sepharose) except in the non-binding mode with 100 mM Phosphate, 10 mM NaCl, and pH 7.0.

The second column step uses the same principles as the first but in reverse mode such that the contaminants that were co-eluted on the binding column have an opportunity to be retained on the matrix at a neutral pH. The flow through material from the first capture column can also be treated with a variety of alternative types of chromatography approaches, for example, cation exchange, hydrophobic, mixed mode, or gel filtration chromatography.

In a preferred method, the flow through material from the Q sepharose non-binding column is concentrated on a 10 kDa or 30 kDa crossflow membrane until the concentration is between 15 and 25% albumin. The buffer is then changed by diafiltration into a suitable buffer for cell culture such as Dulbeccos PBS or alternatively 20 mM Phosphate, 50 mM NaCl, and pH 7.0. The material is then sterile grade filtered into a sterile container. The sterile filtered material may be treated with detergent to destroy enveloped viruses and to aid in the removal of hydrophobic toxins and contaminants. In a preferred method, 0.5% v/v Triton X-114 or X-100 is added to the 15 to 25% albumin solution at room temperature (less than 23 C and greater than 18 C) and the solution is agitated or stirred for at least hour. The material is then passed over a hydrophobic resin with a molecular weight exclusion limit that is much less than the molecular weight of albumin. Many commercially available resins are available including those from Biorad and Pall Corporation.

The material that is passed over the column may then be tested in cells that are sensitive to detergent to confirm biological activity. The residual detergent that remains should typically be less than 0.005% with respect to the albumin solution. The detergent free flow through can then be sterile filtered into containers for direct shipment, or can have stabilizers added, or can be subjected to pasteurization with stabilizers, or can have stabilizers added before drying or dried directly. The material may be dried by lyophilization or spray drying. Prior to drying, in some instances, it may be useful to subject the material to a virus filtration step using a disposable, validated, virus removing capsule such as is available from GE, Pall, and Millipore. It is common in the art to understand that a prefiltration step may be necessary in order to effectively and economically pass the concentrated material through a 20 nm filter.

Results: Rice flour was extracted at 1:5 ratio in phosphate buffered saline and mixed for 20 minutes. The liquid was clarified using a Nalgene filter flask. The subsequent clarified extract was subjected to acid precipitation as is described in the methods. The solution was then filtered and neutralized to give a clarified filtrate. This material was diafiltered against 50 mM Tris/Cl pH 8.0 until the material and buffer were equilibrated. The material was then loaded (300-600 cmh) on a pre-equilibrated GE Q-sepharose column to allow for 50 g/L binding capacity. The loaded material was washed with the same buffer and the material was then eluted with 100 mM Phosphate, 10 mM NaCl, and pH 4.0 as described above. The material eluted in a sharp peak and the collected eluate had a stable pH of about 5.8. Albumin produced using this method was compared to other sources of Albumin as more fully disclosed below: The eluate was collected in a pool and 1M NaOH was added until the pH was greater than 6.0. The material was then concentrated on a 10 kDa regenerated cellulose membrane approximately 5 fold and approximately five equal volume diafiltrations were carried out with 100 mM phosphate, 10 mM NaCl, pH 7.0. The final diafiltered material was checked for albumin protein content (in relation to the expression level in the starting material should be greater than 80%) and endotoxin level (should be less than 100 EU/mg depending on the feed material). This material was passed (60-160 cmh) over a Q-sepharose column, equilibrated with 100 mM phosphate, 10 mM NaCl, pH 7.0, of sufficient size to allow for approximately 2-3 times loading volume. The material was washed through the resin with the same buffer and collected. The collected material was diafiltered on a 10 kDa regenerated cellulose membrane and concentrated approximately 10 fold or until the albumin concentration reaches at least 10% or not more than 20% and five equal volume diafiltrations were performed with 20 mM phosphate, 50 mM NaCl, pH 7.0. After sterile grade filtration (0.2 μm), the solution was agitated for 1 hour with 0.5% (v/v) Triton X-100 at 20+/−2° C. After the incubation, the material was passed through Pall SDR resin according to the manufacturer's directions. The flow through material was sterile grade filtered into sterile containers and refrigerated or freeze dried as is common for protein and salt solutions.

Example 6: Comparison of Recombinant Albumin Produced from Rice Using B0000C Process Compared to Other Sources of Albumin and Previous Methods for the Production of Albumin Methods: Albumin prepared using process B0000 described in Example 5, was compared to albumin prepared using an alternative process (B000) which was previously used to prepare recombinant albumin (Cellastim (Batches B202 to B217)).

Albumin Production (Old Process, B000):

Rice flour and 25 mM Sodium phosphate, 50 mM Sodium Chloride, was pH balanced to 6.5 with NaOH and mixed for 20 minutes at room temperature with a S/L ratio of approximately 1:10. Filter aid (Cellpure 300) was added at 10 g/L and the slurry was filtered by filter press, vacuum filtration, or centrifugation. The clarified filtrate was acid precipitated to about pH 5.0 with 1 M acetic acid. The resulting solution was filtered as described above with the addition of 5 g/L filter aid (Cellpure 300). The material was neutralized immediately to pH 6.5 to 7.0 with 1M NaOH. The material was diafiltered (10 kDa regenerated cellulose for all UFDF steps) with 5 equal diavolumes of the same buffer used for extraction. The material was loaded on a pre equilibrated Q-sepharose column (GE Healthcare) to allow for 8 g albumin binding per liter of resin at 60 cmh.

After washing the column with 5 column volumes of the same buffer, the albumin was eluted by increasing the salt concentration to 250 mM NaCl in one step. The resulting material was diafiltered against 100 mM Sodium Phosphate, 10 mM NaCl, pH 7.0 with 5-7 equal diavolumes. The resulting material was passed over a Q-sepharose column equilibrated with the 100 mM Sodium Phosphate, 10 mM NaCl, pH 7.0, and collected as flow-through. The flow-through material was then concentrated and diafiltered against 20 mM sodium phosphate, 10 mM NaCl, pH 7.0 with 5 diavolumes. The final concentrated material was sterile filtered and incubated with 10 g/L of the detergent CHAPS ((3-Cholamidopropyl)dimethylammonio)-1-Propanesulfonic Acid) and mixed at room temperature for 1 hour. After the one hour incubation, the material was passed over a Biorad SM-2 column. The material was sterile filtered and freeze dried.

Size Exclusion Chromatography Analysis.

Purity analysis by HPLC was carried out in 100 mM phosphate, pH 7.0 on a GF-250 column (Agilent Technologies) at a flow rate of 1 ml/min with the detector set at 214 and 280 nm. A standard curve was developed by injecting 5 different dilutions made by dry powder with a correction factor of 0.92 for salt and moisture. The main peak from 214 nm was integrated either by retention time or alternatively baseline. The unknown sample was injected at a concentration that is within the range of the standard injections. The unknown concentration of albumin per dry powder weight (purity) was calculated from the standard curve. In a typical experiment, the 0, 5, 8, 10, 15, and 20 μg of the standard was injected followed by approximately 10 μg of unknown sample in approximately 50 μL injection volume. The correlation coefficient for the standard curve after integrating the peaks was typically above 0.98.

SDS PAGE and Densitometry: (Sodium Dodecyl Sulfate Polyacrylamide Gel Electrophoresis). Samples were prepared by diluting the protein solutions to 1-2 mg/ml to enable a defined amount of each protein to be loaded on to each well. The sample was mixed 1:1 with Tris-Glycine SDS sample buffer (LC2673 Novex) containing reducing agent (Invitrogen NP0004) and heated to 70° C. for 5 minutes. The sample was loaded (10, 20, or 30 μg) onto a Novex 4-20% precast gel and separated at constant voltage (130V) in standard Tris-Glycine-SDS running buffer. The electrophoresis was ended when the tracking dye reached the end of the gel. A molecular weight marker was included in the first lane as a reference.

The gel was stained with G Bioscience (786-35G) and destained with water. A digital image was obtained with a Hewlett Packard Scanner (G4010). The image file was then opened with UN-SCAN-IT (Silk Scientific Corp.). The densitometry was carried out with positive image analysis in 256 grayscale in which all visible bands were included as individual segments. The background noise was corrected by four corner interpolation as specified in the software for each segment. The signal for each segment or band was then calculated from the product of the # of pixels and the average pixel intensity (0-255). The sum of the signals for an entire lane (all visible segments or bands) was taken as 100% and the impurity bands were subtracted to calculate the albumin purity. The percent of each contaminating protein in each band was calculated as the number of peptides identified for that contaminant protein as determined by peptide mapping divided by the total number of all peptides identified in a particular band. The image analysis was repeated 3 times such that the standard deviation is less than 0.5% out of 100%.

Determination of Endotoxin by the Pyrogene rFC Method.

Endotoxin content was determined by the Pyrogene rFC method. Lyophilized endotoxin standard was mixed with endotoxin free water as specified by the manufacturer (Lonza) to develop a standard curve. The protein samples were either diluted as is for liquid or alternatively, reconstituted with endotoxin free water for powder. Different dilutions were prepared such that the readings should appear within the range of the standard curve. The samples were heated to 100° C. for 10 minutes to dissociate unwanted molecular interactions. In a typical experiment, the sample and standard were added at 100 μl per well, with 0, 0.001, 0.005, 0.01, 0.05, and 0.1 endotoxin units per well. The samples were also added at 100 μl and extra samples were included such that spiking with 0.001-0.01 endotoxin units per well were added to test for assay inhibition or interference. The working reagent was prepared according to the manufacturer (Lonza) by mixing the rFC enzyme, assay buffer, and substrate in a 1:4:5 ratio, respectively. The working reagent was added to the wells at equal volume to the sample or standards. The fluorescence plate reader (Biotek FLX 800T) was set for excitation at 380 nm (bandwidth=20 nm) and the emission wavelength was set at 440 nm (bandwidth=30 nm). The reading taken at time zero is subtracted from the reading taken after 1 hour at 37° C. The readings were considered valid if the correlation coefficient, slope, and Y-intercept for the standards was within the set limits, and the spiking experiments show that the spiked endotoxin was measureable and recoverable within the set limits. In addition, the standard deviation for duplicate samples should be in reasonable agreement such that the standard deviation was within a specified arbitrarily chosen limit. All samples were collected aseptically and the tubes/vials/containers used for testing were verified to be extremely low endotoxin following good laboratory practices as they relate to accurate and precise endotoxin testing.

Determination of Cell Viability

The hybridoma cell line AE1 (ATCC) was maintained in DMEM basic media containing 5% fetal bovine serum (FBS). Albumin was tested under serum-free conditions (AFM6, KC Bio, Kansas) without supplementation of fetal bovine serum. The cells were subculture from 5% FBS to serum free media over multiple passages. At each subculture, the cells were analyzed for total cell count and viability in the presence of the indicated concentrations of albumin. (As assessed by trypsinization and direct counting using a Neubauer haemocytometer). The cells were grown under standard culture conditions (5% $CO_2$ and 37° C.) for approximately 70 hours after which the viability for the cultures was measured. The experiments were conducted in duplicate. Date show the number of viable cells/ml divided by $10^5$.

Determination of Detergent

The detergent concentration for the albumin was determined by a detergent (cell based) assay. Briefly, detergent sensitive cells were spiked with different amounts of detergent and the resulting cell viability cell determination used to generate a standard curve consisting of 16 independent data points. The change in viability with respect to the change in detergent concentration was plotted and fitted with a logarithmic function. This equation was then used to calculate the unknown detergent concentrations in samples tested in the same cell based assay. The correlation coefficient for the standard curve for the data given was 0.9816. Typically detergent concentrations of greater than about 10 ppm per Cellastim dry weight, result in noticeable toxic activity. By comparison in a 10% albumin solution, toxic effects of detergent become apparent when the detergent concentration is above about 100 ppm to 200 ppm or 0.01% to 0.02% (v/v).

Results & Discussion:

I. Analysis by Size Exclusion chromatography of plasma derived serum (Sigma Albumin), and recombinant HSA (Cellastim) produced using the new process (B0000) (Cellastim P0171) and the old process (Cellastim P0107).

Figure 8A:
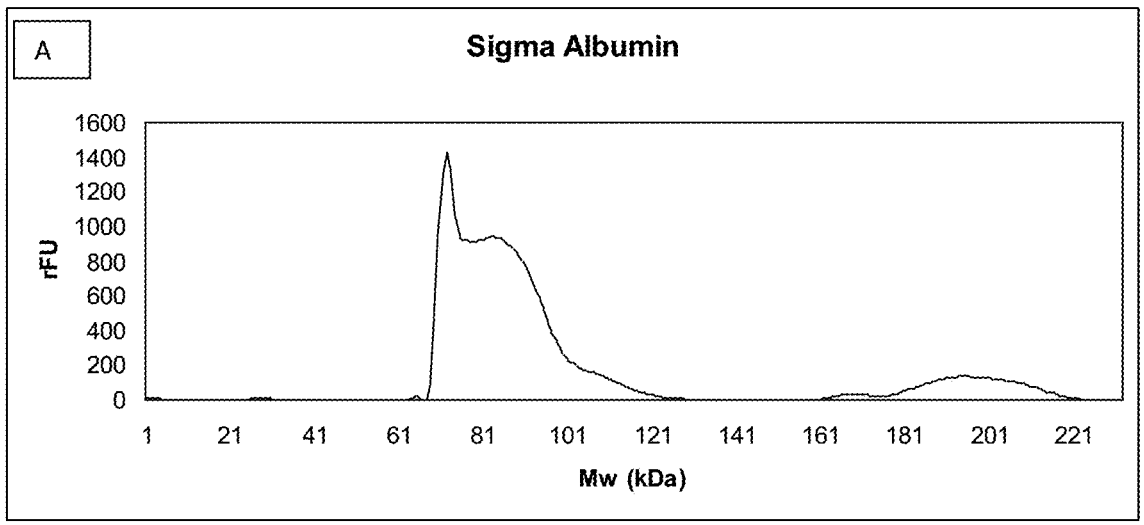
FIG. 8A-FIG. 8E Shows a comparison by HPLC size exclusion chromatography of recombinant HSA produced from rice compared to other sources of albumin and methods of purification.

The HPLC size exclusion profiles (FIGS. 8A, C & D) for the three types of albumin show that in terms of overall purity the different albumin preparations are generally similar. Specifically, the peaks at around 4.5 kDa and 240 kDa are the internal controls, while all three products contain a very small amount of an off main peak signal at about 10-12 kDa.

Figure 8B:
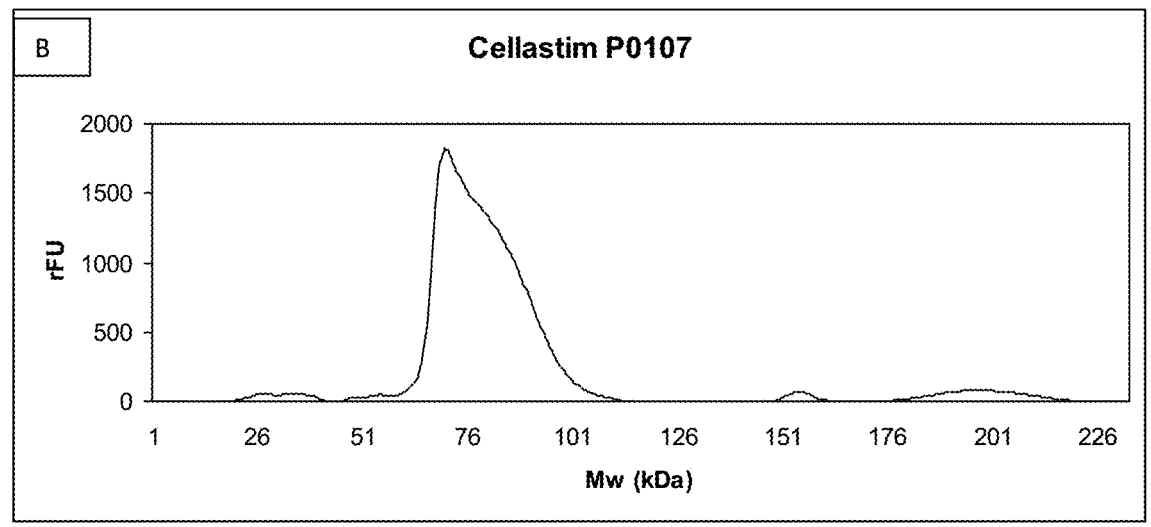
Figure 8C:
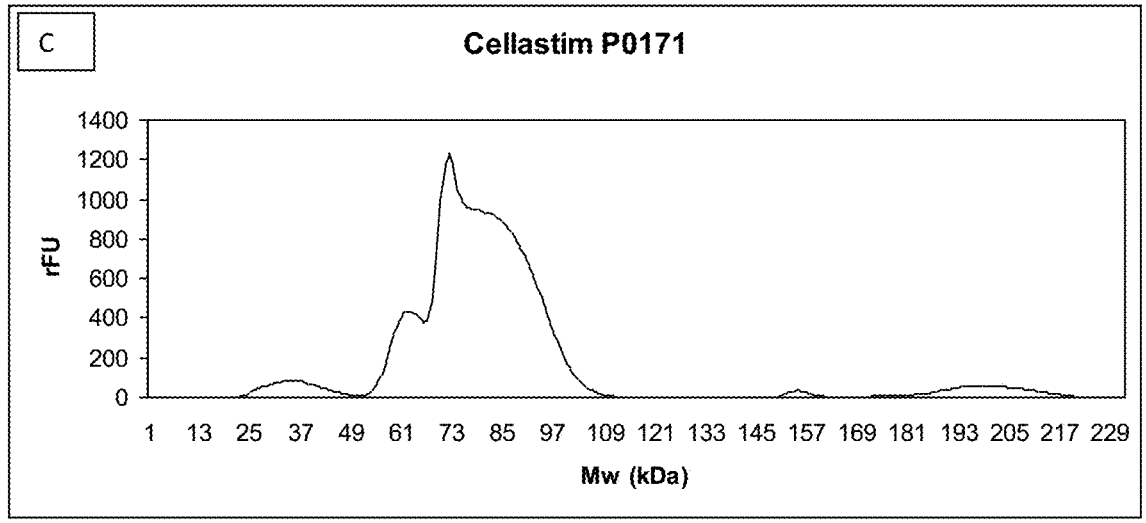
Figure 8D:
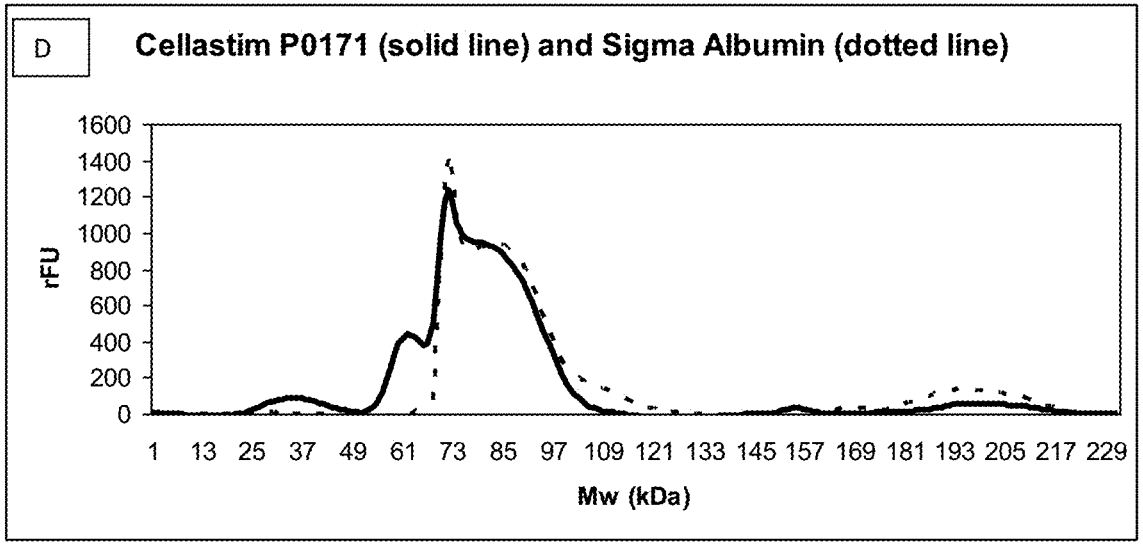
Figure 8E:
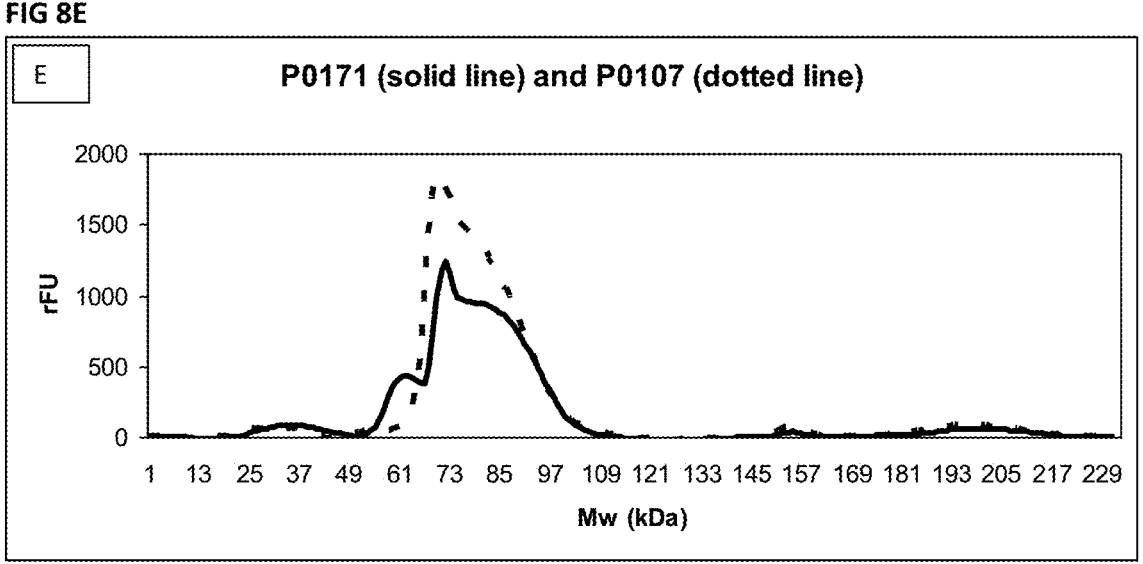

Human plasma derived albumin (Sigma Albumin) (FIG. 8A), contains a contaminant at around 17 kDa, by comparison the recombinant rice derived albumin using the new process (Cellastim P0171) (FIG. 8C) contains two protein contaminants of around 44 KDa and 55 kDa that occur in Cellastim made with the new process at significantly higher levels than when using the old process (Cellastim P0107) (FIG. 8B). These peaks are not completely resolved in the HPLC separations, but can be seen as more clearly in the overlaid profiles of Cellastim P0171 and Sigma albumin (FIG. 8D) and Cellastim made using the old and new processes shown in FIG. 8E.

The proteins corresponding to these peaks represent about 5% of all of the contaminant proteins identified by Peptide Mass Fingerprinting analysis of the main albumin peak in Cellastim produced using the process described in Example 5, as discussed further below.

All albumin products tested also contained a peak at around 130 kDa that most likely represents albumin dimers, it is noticeable that the Cellastim dimer peak is significantly smaller than the plasma derived albumin. The creation of aggregated albumin is an indicator of protein degradation which is used as one marker for degradation or loss of stability industry wide. It is likely that the Hsps present in Cellastim promote the disaggregation of the albumin, therefore reducing the number of dimers, since it is a commonly known function of Hsp 70 and other Hsp proteins.

II. Analysis by SDS PAGE of Cellastim batch P0171 (New process) compared to albumin produced by Millipore/Novozymes (Cat No. 9301-01).

Figure 9A:
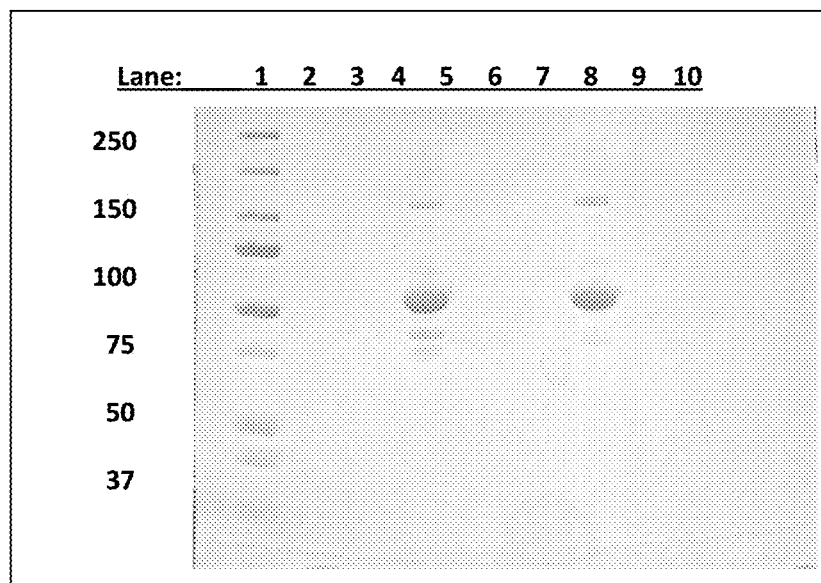
FIG. 9A-FIG. 9B Shows a comparison by SDS PAGE analysis of recombinant albumin produced from rice compared to other sources of HSA and methods of purification.
Figure 9B:
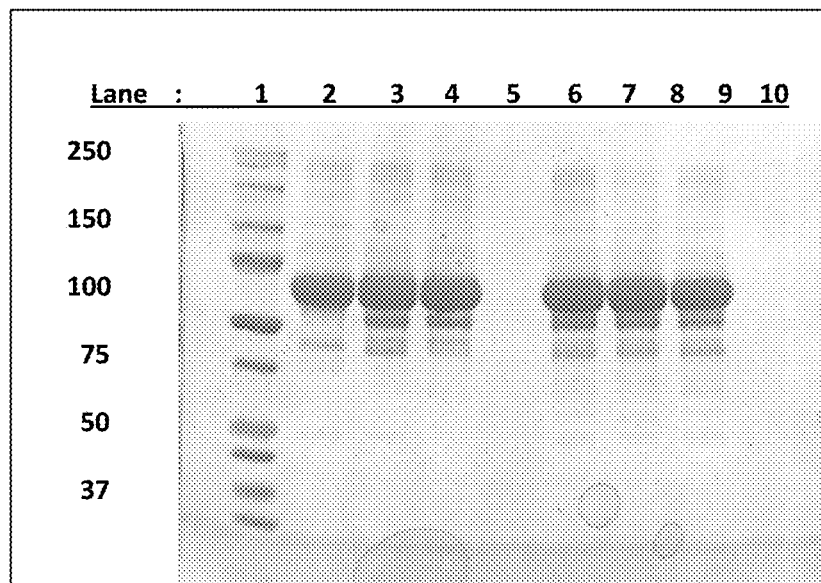

Results: SDS-PAGE analysis (FIGS. 9A & B) shows that in terms of overall purity the products are generally similar. FIG. 9A shows a comparison of Cellastim P0171 and Cellprime albumin (Millipore/Novozymes). Lane 1 is the molecular weight marker. Lane 4 is the Cellastim albumin (10 μg) and Lane 7 is the Cellprime albumin (10 μg). FIG. 9B shows a comparison by SDS PAGE analysis of three Cellastim lots from the previous process (B000) (Lane 2, 3, and 4), and the new Cellastim Process (B0000C) (Lane 6, 7, and 8). The six samples were loaded at 20 μg per lane.

Visual inspection of the gel shows that the new process which meets more rigorous specifications is more consistent among the 3 lots tested. (FIG. 9B, lane 2, 3, 4 vs. lane 6, 7, 8). The banding pattern is significantly different among the three samples from the previous process as compared to the new process. Importantly, the new process samples have significantly less aggregates at around 250 KDa than the old process samples have. (Average greater than 2% for the old process, and average less than 1% for the new process). The identity of the protein contaminates was that are enriched in Cellastim produced using the new process is discussed further below.

III. Analysis of endotoxin, detergent and growth promoting abilities of old and new batches of Cellastim. A comparison of the performance of the two different processes for preparing several different lots of albumin (Tables E3 and E4) demonstrates that the old process produced recombinant albumin that contained significantly more endotoxin, and detergent compared to the new process described in Example 5, and resulted in a product that significantly enhanced cell viability.

TABLE E3

| Cellastim - Old Process B000 | | | | | | | | |
|---|---|---|---|---|---|---|---|---|
| | | | | | \multicolumn{4}{c}{Viability (number of viable cells/ml/$10^5$)} |
| Production Date | Batch Number | Grams product | Dry Material | Detergent (ppm) EU/mg | 1 mg/ml | 2 mg/ml | 5 mg/ml | 10/ mg ml |
| Feb. 27, 2008 | B202 | 70.6 | 25.3 | 815.3 | 15 | 7.9 | 4.1 | 0.9 |
| Feb. 27, 2008 | B203 | 58.8 | 23.1 | 267.7 | 15.8 | 12.4 | 6.5 | 4.1 |
| Feb. 28, 2008 | B204 | 59.9 | 29.2 | 589.2 | 16.3 | 11.1 | 5.2 | 2.9 |
| Feb. 28, 2008 | B205 | 63 | 64.3 | 133.4 | 14 | 11.6 | 6.9 | 3.8 |
| Mar. 3, 2008 | B206 | 41.1 | 35.1 | 1182.2 | 14.9 | 2.3 | 0.0 | 0.0 |
| Mar. 3, 2008 | B207 | 94.2 | 28.7 | 388 | 16.5 | 12.7 | 7.6 | 4 |
| Mar. 4, 2008 | B208 | 24.5 | >80 | 467.2 | 15.3 | 11.4 | 7.1 | 2.7 |
| Mar. 4, 2008 | B209 | 66.1 | 91.8 | 406.4 | 16.7 | 15.2 | 6.9 | 4.1 |

TABLE E3-continued

Cellastim - Old Process B000

| Production Date | Batch Number | Grams product | Dry Material | Detergent (ppm) | Viability (number of viable cells/ml/$10^5$) | | | |
|---|---|---|---|---|---|---|---|---|
| | | | | | 1 mg/ml | 2 mg/ml | 5 mg/ml | 10/ mg ml |
| Mar. 4, 2008 | B210 | 87.3 | 67.8 | 76.4 | 17.5 | 19.1 | 15.4 | 8.5 |
| Mar. 11, 2008 | B217 | 62.09 | 4.4 | 127.3 | 16.7 | 18.7 | 13.2 | 6.6 |
| Averages | | | 44.97 | 445.31 | 15.87 | 12.24 | 7.29 | 3.76 |

TABLE E4

Cellastim - New Process B0000C

| Production Date | Batch Number | Grams product | Dry Material | Detergent (ppm) | Viability (number of viable cells/ml/$10^5$) | | | |
|---|---|---|---|---|---|---|---|---|
| | | | | | 0.5 mg/ml | 2 mg/ml | 5 mg/ml | 10/ mg ml |
| Feb. 2, 2009 | B0032C | 209.4 | 0.35 | 3.1 | 13.1 | 15.7 | 13.4 | 11.2 |
| Feb. 2, 2009 | B0033C | 271.4 | 0.26 | 7.9 | 18.4 | 17.4 | 15.1 | 14.3 |
| Feb. 10, 2009 | B0041C | 247.1 | 0.18 | 5.4 | 15.4 | 17.2 | 14.1 | 12.1 |
| Apr. 27, 2009 | B0118C | 617.4 | 0.11 | Less than 1 | 15.7 | 15.4 | 19.2 | 16.8 |
| May 14, 2009 | B0138C | 610.6 | 0.48 | Less than 1 | 12.5 | 15.8 | 15.1 | 14.6 |
| Jun. 9, 2009 | B0158C | 598.0 | 0.13 | 3.9 | 13.7 | 17.1 | 13.2 | 11 |
| Jun. 15, 2009 | B0162C | 618.6 | 0.20 | 2.0 | 15.5 | 17.5 | 17.2 | 14.7 |
| Jul. 28, 2009 | B0196C | 507.0 | 0.36 | 3.9 | 17.4 | 17.3 | 18.8 | 14.8 |
| Aug. 26, 2009 | B0219C | 851.4 | 0.86 | 8.2 | 17.9 | 16.3 | 16.6 | 13.7 |
| Aug. 31, 2009 | B0220C | 897.8 | 0.93 | Less than 1 | 13.5 | 16 | 15.5 | 15.1 |
| Sep. 9, 2009 | B0227C | 929.9 | 0.13 | Less than 1 | 11.1 | 14.4 | 12.5 | 11.4 |
| Averages | | | 0.36 | 3.45 | 14.92 | 16.37 | 15.52 | 13.6 |

Discussion: Re-engineering the old process to create the new process described in Example 5 resulted in significant changes in both overall product purity, and performance, as described more fully below.

The changes made it possible to make products that were lower in detergent, lower in endotoxin, and increased purity. Specifically, the new process routinely produced recombinant albumin with an overall purity of greater than about 95%. By comparison the old method routinely produced albumin with a maximum purity of about 90%. Surprisingly, despite the increased product purity, these changes in processing also resulted in enhanced co-purification of heat shock proteins, (see below) with the recombinant albumin. Without being bound by any particular theory of operation, it is believed that the combination of high albumin purity, relative lack of endotoxin and/or detergent, and co-purification of heat shock proteins results in a product that significantly out performs previous methods for preparing albumin.

Specifically Tables E3 and E4 demonstrate that the new process for producing recombinant albumin results in a product that, for example at 5 mg/ml, results in an average batch to batch 100 percent improvement in cell viability (at 5 mg/ml), and also results in a product with an average 100-fold less endotoxin, and 100 fold less detergent than the old process.

Example 7: Analysis of the Effects on Cell Growth and Viability

To compare the cell growth promoting abilities of the recombinant albumin prepared above, to other commercially available albumin products, the different sources of albumin they were compared side by side in a cell growth and viability assay. The three products tested were (Cellastim, Lot #P0153) Cellprime albumin (Millipore/Novozymes Cat No. #9301-01), and plasma derived albumin (Seracare Cat No. #HS-400-60).

Figure 10A:
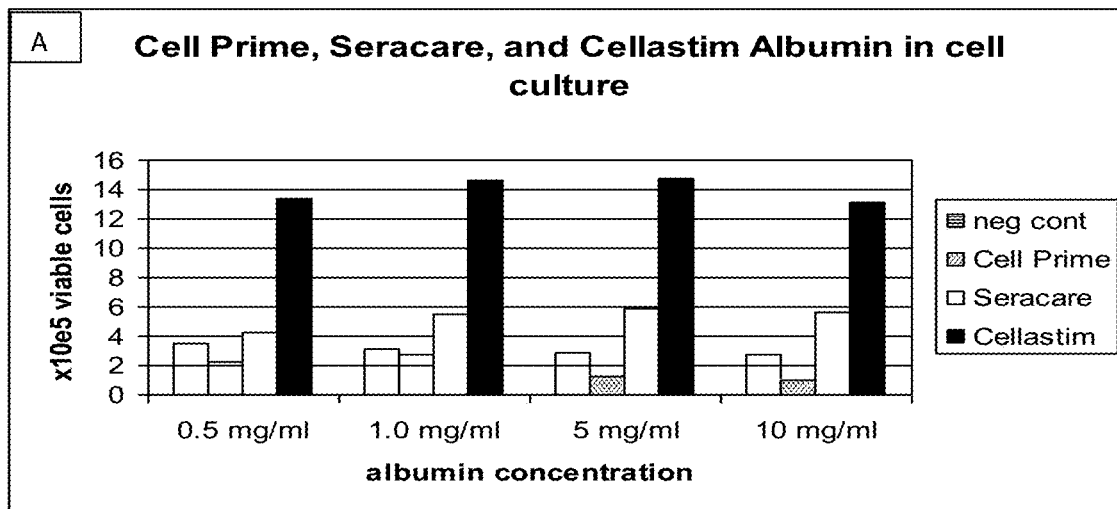
FIG. 10A: Shows a comparison of the effects of yeast recombinant HSA (Cellprime), human plasma derived HSA, (Seracare) and plant recombinant HSA (Cellastim P0171) with respect to their ability to promote cell growth and viability.
Figure 10B:
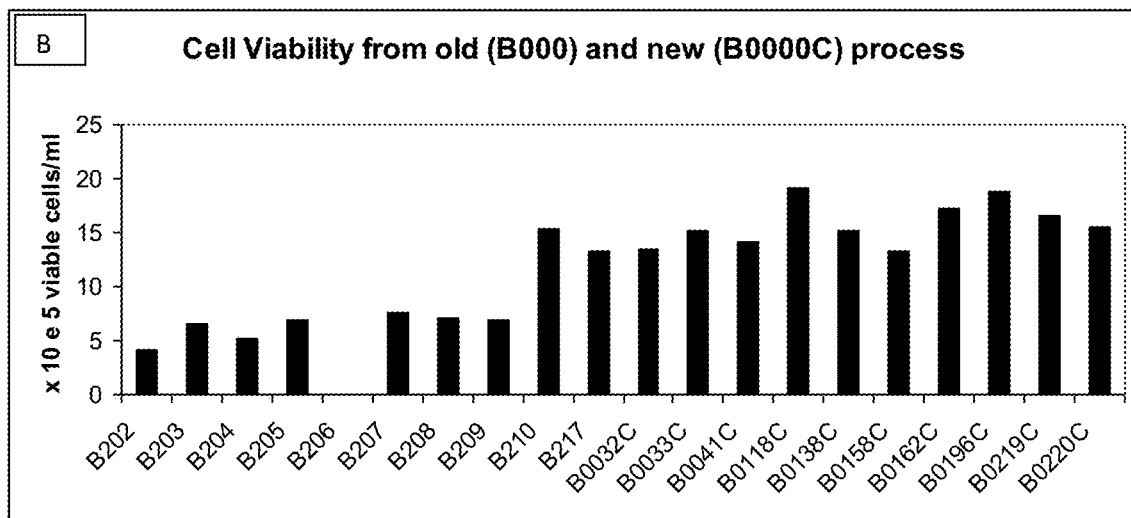
FIG. 10B shows a comparison of the endotoxin levels in batches of albumin produced using the old (B000) and new processes (B0000C) for recombinant albumin production.
Figure 10C:
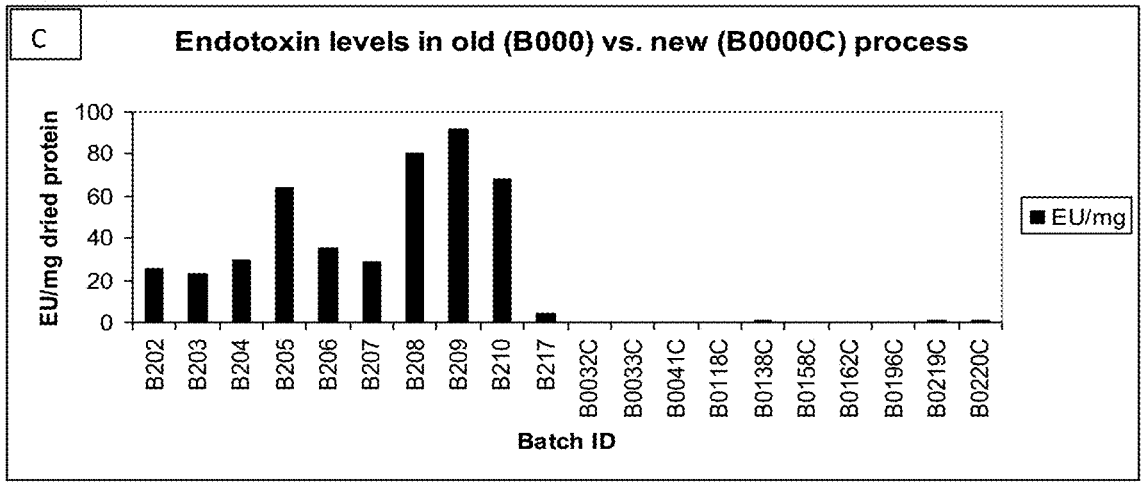
FIG. 10C shows a comparison of cell growth and viability of cells grown in the presence of the Cellastim HSA produced using the old (B000) and new processes (B0000C) for recombinant albumin production.

Methods: Specially conditioned Hybridoma cells AE1 were seeded in DF12/ITSE at a density of $0.5 \times 10^5$ cells per ml of media after washing twice with same media to remove residual media. The media and cells were then left untreated (negative control), treated with Seracare albumin, treated with Cellprime albumin, and treated with rice derived recombinant albumin at the concentrations shown in the figure legend. The cells were grown under standard culture conditions (5% $CO_2$ and 37° C.) for approximately 70 hours after which the viability for the cultures was measured. The experiments were conducted in duplicate. Results are shown in FIG. 10.

Results: Novazyme's Cellprime albumin caused a loss in viability (cross-hatch bars). Seracare albumin (white bars) caused a measureable increase in viability but not as large an increase as is seen with recombinant albumin made in rice with the new process (Cellastim) (black bars). Under these conditions the rice derived recombinant albumin was approximately 5 times as active in promoting cell viability compared to any of the other albumin products, at any concentration tested. The negative control is represented by the striped bars.

Discussion: Given the possibility that the other commercially available albumin products may have similar overall purity, endotoxin and detergent levels to rice derived recombinant albumin, the dramatically superior performance of the recombinant rice derived albumin compared to other commercially available albumins suggests that the previously un-identified protein contaminants identified in Cellastim compared to the plasma derived albumin (Example 5) could be having a positive impact on cell viability. To identify and then characterize the impact of these proteins on the properties of Cellastim, a sample of the recombinant albumin was subjected to peptide mass finger printing, as described below.

Example 8: Peptide Mass Finger Printing of Recombinant Human Serum Albumin

Methods: Samples of albumin were analyzed to determine significant protein contaminants using a NanoLCMS/MS peptide sequencing system (ProtTech, Inc.), and proprietary software to identify the proteins based on the molecular weight of the peptide fragments. In brief, samples of albumin were analyzed by SDS-PAGE, and each major band gel band was destained, cleaned, and digested in-gel with sequencing grade modified trypsin. The resulting peptide mixture was analyzed by a LC-MS/MS system, in which a high pressure liquid chromatography (HPLC) with a 75 micrometer inner diameter reverse phase C18 column was used in-line coupled with an ion trap mass spectrometer. The mass spectrometric data acquired was used to search the most recent non-redundant protein database with ProtTech's proprietary software suite. The output from the database search was manually validated before reporting.

Results: Upon testing of three representative lots of recombinant albumin, three Hsp70 proteins were identified by Peptide Mass Fingerprinting (Table E5). The three specific sequences identified: ABF95267, ABA97211, and BAD 07938 were compared to the non redundant database to identify highly related and homologous proteins. The results of the top hits from each of these comparisons is shown in Tables E6, E7 and E8 below.

TABLE E5

Peptides identified from Cellastim by mass finger printing

| Sequence | Peptide |
|---|---|
| ABF95267 | ATAGDTHLGGEDFDNRVVPGPADKSPMIV VTYKGEEK NAVITVPAYFN DSQRIINEPTAAAIAYGLDKK (SEQ. ID. No. 2) |
| AAB63469 | NQAAVNPER NGHVEIIANDQGNRIVNKD GKPYIQVK |
| BAD07938 | IINEPTAAAIAYGLDKK KLGTVIGIDLG TTYSCVGVYK |
| BAD07713 | VEIESLFDGTDSFSEPLTR (SEQ. ID. No. 3) |
| ABA97211 | NQADSVVYQTEK KQDITITGASTLPKDEVERDVVLLDVTPL SLSLGLET LGGVMTK (SEQ. ID. No. 4) |

Results of sequence comparisons to ABF95267 sequences in the non redundant database of protein sequences in Genbank® (Nucleic Acids Research, 2008 January; 36 (Database issue):D25-30) are shown in Table E6 below:

TABLE E6

Sequences producing significant alignments with ABF95267:

| Gene Refs | Gene description | (Bits) | Value |
|---|---|---|---|
| ref|NP_001140835.1| | hypothetical protein LOC100272911 [Zea ma . . . | 79.7 | 8e-14 |
| ref|XP_002465468.1| | hypothetical protein SORBIDRAFT_01g039390 . . . | 79.7 | 9e-14 |
| ref|NP_001049719.1| | Os03g0277300 [Oryza sativa (japonica cult . . . | 79.7 | 9e-14 |
| gb|ACJ54890.1| | heat shock protein 70 [Oryza sativa Japonica G . . . | 79.7 | 9e-14 |
| Sp|P09189.1| | HSP7C_PETHY RecName: Full = Heat shock cognate 70 k . . . | 77.0 | 5e-13 |
| emb|CAA31663.1| | hsp70 (AA 6 - 651) [Petunia x hybrida] | 77.0 | 5e-13 |
| ref|XP_002312089.1| | predicted protein [Populus trichocarpa] > . . . | 77.0 | 5e-13 |
| sp|P24629.1| | HSP71_SOLLC RecName: Full = Heat shock cognate 70 k . . . | 77.0 | 5e-13 |
| gb|AAB99745.1| | HSP70 [Triticum aestivum] | 76.6 | 6e-13 |
| gb|AAB42159.1| | Hsc70 [Lycopersicon esculentum] | 76.6 | 7e-13 |
| gb|ACD45076.1| | heat-shock protein 70 [Dactylis glomerata] | 76.3 | 8e-13 |
| ref|XP_002512741.1| | heat shock protein, putative [Ricinus com . . . | 75.9 | 1e-12 |
| ref|XP_002512742.1| | heat shock protein, putative [Ricinus com . . . | 75.9 | 1e-12 |
| gb|AAA82975.1| | PsHSP71.2 >emb|CAA67867.1| heat shock protein . . . | 75.9 | 1e-12 |
| gb|AAS09825.1| | heat shock cognate protein 70 [Thellungiella h . . . | 75.9 | 1e-12 |
| emb|CAA44820.1| | heat shock protein 70 [Nicotiana tabacum] | 75.5 | 2e-12 |
| ref|NP_001055754.1| | Os05g0460000 [Oryza sativa (japonica cult . . . | 75.5 | 2e-12 |
| ref|NP_001051724.1| | Os03g0821100 [Oryza sativa (japonica cult . . . | 75.1 | 2e-12 |
| ref|XP_002456611.1| | hypothetical protein SORBIDRAFT_03g039360 . . . | 75.1 | 2e-12 |
| ref|NP_001044757.1| | Os01g0840100 [Oryza sativa (japonica cult . . . | 75.1 | 2e-12 |
| gb|ACR35910.1| | unknown [Zea mays] | 75.1 | 2e-12 |
| ref|XP_002284017.1| | PREDICTED: similar to HSC70-1 (heat shock . . . | 75.1 | 2e-12 |
| ref|XP_002532297.1| | heat shock protein, putative [Ricinus com . . . | 75.1 | 2e-12 |
| ref|XP_002284008.1| | PREDICTED: similar to HSC70-1 (heat shock . . . | 75.1 | 2e-12 |
| ref|XP_002283532.1| | PREDICTED: similar to HSC70-1 (heat shock . . . | 74.7 | 3e-12 |
| ref|XP_002332067.1| | predicted protein [Populus trichocarpa | 74.7 | 3e-12 |
| gb|AAF34134.1| | high molecular weight heat shock protein [Malu . . . | 74.7 | 3e-12 |
| gb|EEC76425.1| | hypothetical protein OsI_14101 [Oryza sativa I . . . | 74.7 | 3e-12 |
| ref|XP_002316294.1| | predicted protein [Populus trichocarpa] > . . . | 74.7 | 3e-12 |
| ref|XP_002283516.1| | PREDICTED: similar to HSC70-1 (heat shock . . . | 74.3 | 3e-12 |
| ref|XP_002441219.1| | hypothetical protein SORBIDRAFT_09g022580 . . . | 74.3 | 4e-12 |

Results of sequence comparisons of ABB63469 to sequences in the non redundant database of protein sequences in GenBank® are shown in Table E7 below:

TABLE E7

Sequences producing significant alignments with AAB63469:

| Gene Refs | Gene description | (Bits) | Value |
|---|---|---|---|
| emb|CAP31983.1| | *C. briggsae* CBR-HSP-4 protein [*Caenorhabditis* . . . | 50.1 | 7e−05 |
| dbj|BAG60366.1| | unnamed protein product [*Homo sapiens*] | 49.7 | 8e−05 |
| ref|YP_002421952.1| | chaperone protein DnaK [*Methylobacterium* . . . | 49.7 | 9e−05 |
| ref|YP_001640420.1| | chaperone protein DnaK [*Methylobacterium* . . . | 49.7 | 9e−05 |
| ref|NP_001105893.1| | Binding protein homolog1 precursor [*Zea m* . . . | 49.3 | 1e−04 |
| gb|AAA62325.1| | HSP70 | 49.3 | 1e−04 |
| ref|YP_001756576.1| | chaperone protein DnaK [*Methylobacterium* . . . | 49.3 | 1e−04 |
| gb|AAB63469.1| | endosperm lumenal binding protein [*Oryza sativa*] | 49.3 | 1e−04 |
| ref|YP_001925829.1| | chaperone protein DnaK [*Methylobacterium* . . . | 49.3 | 1e−04 |
| ref|NP_001105894.1| | Binding protein homolog2 precursor [*Zea m* . . . | 49.3 | 1e−04 |
| gb|ACF86491.1| | unknown [*Zea mays*] | 49.3 | 1e−04 |
| ref|NP_001045675.1| | Os02g0115900 [*Oryza sativa* (*japonica* cult . . . | 49.3 | 1e−04 |
| ref|ZP_02191025.1| | Molecular chaperone [alpha proteobacterium . . . | 49.3 | 1e−04 |
| ref|XP_001701685.1| | binding protein 1 [*Chlamydomonas reinhard* . . . | 48.5 | 2e−04 |
| ref|XP_001701884.1| | binding protein 2 [*Chlamydomonas reinhard* . . . | 48.5 | 2e−04 |
| emb|CAC37635.1| | luminal binding protein, BiP [*Scherffelia dubia*] | 48.1 | 3e−04 |
| gb|AAM93256.1| | heat shock protein 70-C [*Heterodera glycines*] . . . | 48.1 | 3e−04 |

Results of sequence comparisons of sequence ABA97211 to sequences in the non redundant database of protein sequences in GenBank® are shown in Table E8 below:

TABLE E8

Sequences producing significant alignments with ABA97211

| Gene Refs | Gene description | (Bits) | Value |
|---|---|---|---|
| gb|AAK13022.1| | heat shock protein 70 [*Fibrobacter succinogene* . . . | 44.3 | 0.004 |
| ref|XP_002442079.1| | hypothetical protein SORBIDRAFT_08g009580 . . . | 44.3 | 0.004 |
| gb|EEC69073.1| | hypothetical protein OsI_37938 [*Oryza sativa* I . . . | 44.3 | 0.004 |
| ref|XP_001752769.1| | predicted protein [*Physcomitrella patens* . . . | 44.3 | 0.004 |
| ref|NP_001066486.1| | Os12g0244100 [*Oryza sativa* (*japonica* cult . . . | 44.3 | 0.004 |
| gb|ACT65562.1| | 70 kDa heat shock protein [*Triticum aestivum*] | 43.9 | 0.005 |
| ref|NP_001152528.1| | stromal 70 kDa heat shock-related protein . . . | 43.9 | 0.005 |
| gb|ACN31310.1| | unknown [*Zea mays*] | 43.9 | 0.005 |
| ref|XP_001772650.1| | predicted protein [*Physcomitrella patens* . . . | 43.9 | 0.005 |
| ref|NP_001146752.1| | hypothetical protein LOC100280354 [*Zea ma* . . . | 43.9 | 0.005 |
| gb|ABP65327.1| | chloroplast heat shock protein 70 [*Pennisetum* . . . | 43.9 | 0.005 |
| gb|AAO72585.1| | heat shock-related protein [*Oryza sativa* (*japo* . . . | 43.5 | 0.007 |
| ref|YP_001740846.1| | Chaperone protein dnaK (Heat shock protei . . . | 43.5 | 0.008 |
| ref|ZP_03728467.1| | chaperone protein DnaK [*Dethiobacter alkal* . . . | 43.1 | 0.009 |

Discussion: Peptide Mass Fingerprinting identified 3 rice heat shock protein super family members that co-purify with albumin, 2 Rice HSP70 genes, (gb|ACJ54890.1|), EEC69073, and AAB63469—a BiP homolog from rice endosperm tissue (endosperm lumenal binding protein). The complete amino acid sequences coded by these genes are listed below:

Gene gb|ACJ54890.1| heat shock protein 70 [*Oryza sativa Japonica* Group] HSP70 was found to occur in recombinant albumin in Cellastim at approximately 0.07% wt/wt. Its complete amino acid coding sequence (SEQ. ID. No. 5) is provided below:

```
    MAGNKGEGPA IGIDLGTTYS CVGVWQHDRV EIIANDQGNR TTPSYVAFTD TERLIGDAAK

NQVAMNPTNT VFDAKRLIGR RFSDPSVQAD MKMWPFKVVP GPADKPMIVV TYKGEEKKFS

121 AEEISSMVLT KMKEIAEAFL STTIKNAVIT VPAYFNDSQR QATKDAGVIS GLNVMRIINE

181 PTAAAIAYGL DKKAASTGEK NVLIFDLGGG TFDVSILTIE EGIFEVKATA GDTHLGGEDF

241 DNRMVNHFVQ EFKRKHKKDI TGNPRALRRL RTACERAKRT LSSTAQTTIE IESLYEGIDF

301 YATITRARFE ELNMDLFRRC MEPVEKCLRD AKMDKAQIHD VVLVGGSTRI PKVQQLLQDF

361 FNGKELCKSI NPDEAVAYGA AVQAAILSGE GNQRVQDLLL LDVTPLSLGL ETAGGVMTVL

421 IPRNTTIPTK KEQVFSTYSD NQPGVLIQVY EGERTRTKDN NLLGKFELTG IPPAPRGVPQ

481 INVTFDIDAN GILNVSAEDK TTGKKNKITI TNDKGRLSKE EIERMVQEAE KYKAEDEQVR

541 HKVEARNALE NYAYNMRNTV RDEKIASKLP ADDKKKIEDA IEDAIKWLDG NQLAEADEFE

601 DKMKELESLC NPIISKMYQG GAGGPAGMDE DAPNGSAGTG GGSGAGPKIE EVD
```

AAB63469 BiP homolog from rice endosperm tissue (endosperm lumenal binding protein [*Oryza sativa*]) BiP was found to occur in recombinant albumin in Cellastim at about 0.09% wt/wt. Its complete amino acid coding sequence (SEQ. ID. No. 6) is provided below:

```
    mdrvrgsafl lgvllagslf afsvakeetk klgtvigidl gttyscvgvy knghveiian
    dqgnritpsw vaftdserli geaaknqaav npertifdvk rdigrkfeek evqrdmklvp
121 ykivnkigkp yiqvkikdge nkvfspeevs amilgkmket aeaylgkkin davvtvpayf
181 ndaqrqatkd agviaglnva riineptaaa iaygldkkgg eknilvfdlg ggtfdvsilt
241 idngvfevla tngdthlgge dfdqrimeyf iklikkkysk diskdnralg klrreaerak
301 ralsnqhqvr veieslfdgt dfsepltrar feelnndlfr ktmgpvkkam ddagleksqi
361 heivlvggst ripkvqqllr dyfegkepnk gvnpdeavay gaavqgsils geggdetkdi
421 llldvapltl gietvggvmt kliprntvip tkksqvftty qdqqttvsiq vfegersmtk
481 dcrllgkfdl sgipaaprgt pqievtfevd angilnvkae dkgtgkseki titnekgrls
541 qeeidrmvre aeefaeedkk vkeridarnq letyvynmkn tvgdkdklad kleseekekv
601 eealkealew ldenqtaeke eyeeklkeve avcnpiisav yqrtggapgg rrrgrlddeh
661 del
```

EEC69073/OsI_37938 [*Oryza sativa* Indica Group] The stromal HSP70 was found to occur in recombinant albumin in Cellastim at about 0.06% wt/wt. Its complete amino acid coding sequence (SEQ. ID. No. 7) is provided below:

```
    masftsqlga macgaapsts plaarrsgql fvgrkpaaas vqmrvpragr argvamrvac
 61 ekvvgidlgt tnsavaameg gkptvitnae gqrttpsvva ytkggerlvg qiakrqavvn
121 pentffsvkr figrkmaevd deakqvsyhv vrddngnvkl dcpaigkqfa aeeisaqvlr
181 klvddaskfl ndkitkavvt vpayfndsqr tatkdagria glevlriine ptaaslaygf
241 ekknnetilv fdlgggtfdv svlevgdgvf evlstsgdth lggddfdkfy fcwvfyfgam
301 thetpkvvdw lasnfkkdeg idllkdkgal qrlteaaeka kmelstlsqt nislpfitat
361 adgpkhiett lsrakfeelc sdlidrlktp vtnalrdakl svdnldevil vggstripsv
421 qelvkkitgk dpnvtvnpde vvslgaavqg gvlagdvkdv vlldvtplsl gletlggvmt
481 kiiprnttlp tsksevfsta adgqtsvein vlqgerefvr dnkslgsfrl dgippaprgv
541 pqievkfdid angilsvaai dkgtgkkqdi titgastlpk devermveea dkfaqedkek
601 rdaidtknqa dsvvyqtekq lkelgdkvpa pvkekvdakl nelkeaiagg stqsmkdama
661 alneevmqig qamynqqpna gaagptpgad agptssggkg pndgdvidad ftdsn
```

Because these proteins only occur at low levels in the new batches of rice recombinant albumin relative to albumin, a pre-requisite for confirming that these contaminants are actually responsible for the superior growth promoting effects of the new batches of recombinant albumin is to determine whether the addition back of these components to albumin restores or enhances the growth promoting activities of the recombinant albumin at levels which are comparable to those actually identified for each component in Cellastim.

Example 9: Separation of Heat Shock Proteins from Recombinant Albumin by Affinity Chromatography Methods: Cellastim produced using the new process [Lots P0153, P0156, and or P0171] powder was mixed with purified water at approximately 20 g/L. The resulting solution was diafiltered against 50 mM Tris/Cl, pH 7.0 with at least 5 equal volumes of buffer. The resulting solution was passed over an ATP agarose column and the resulting flow through was labeled as fraction A. The column was washed with 5 column volumes of the equilibration buffer and the material bound to the ATP-agarose was eluted with 50 mM Tris/Cl, 1M KCl, pH7.0. The eluted material was labeled as fraction B. The wash was kept as fraction C. Fraction A was directly concentrated to 100 g/L and diafiltered with d-PBS. Fraction B was concentrated significantly, up to 20 fold or 100 fold in 50 mM Tris/Cl for further analysis. The wash fraction C was kept for further reference. For Western blotting, 10 µg of each protein fraction (by A280, where the e.c. (extinction coefficient) of albumin is 0.53 $cm^2$/mg and e.c. of Hsp70 is 0.41 $cm^2$/mg) were loaded on a 4-20% SDS PAGE gel in 2×SDS loading buffer. The samples were heated to 80° C. for approximately 5 minutes before loading. The separation was done at 200V (constant voltage) and ran for approximately 90 minutes. The resulting gel was rinsed in water for 30 minutes to 2 hours and then the proteins were transferred to a Nitrocellulose membrane at 30 mA (constant current) for 2 hours. The resulting blot contained the molecular weight marker proteins as a transfer control and was then blocked in 5% (w/v) milk powder in water. The primary monoclonal antibody (a mouse anti-bovine Hsp70 (Sigma/Aldrich #H5147)) was added in 5% milk solution to the blot (1:2500) and the blot was incubated on a rocker with gentle rocking overnight at 4° C. The blot was then washed 4 times for 10 minutes each in TDN and the secondary antibody (Pierce anti-mouse HRP conjugated) in 5% milk solution which was added at a dilution of 1:2500. After incubation at 4° C. for 2 to 3 hours, the blot was washed 4 times with TDN for 10 minutes each. The resulting blot was then incubated with pico (Pierce) chemiluminescent substrate for 5 minutes. Kodak photographic film was exposed to the blot in a dark room and the subsequent film was developed, rinsed, fixed, rinsed, and dried. To determine accurate transfer of the molecular weight marker position onto the film, a light emitting label was used.

Figure 11:
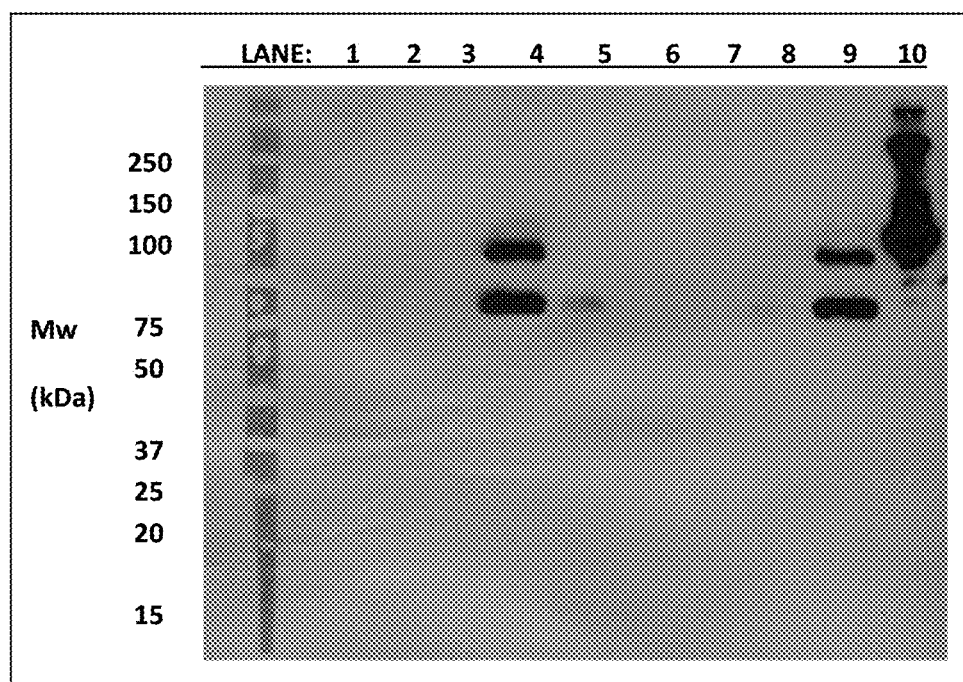
FIG. 11: Shows a western blot of two independent experiments showing that plant derived recombinant HSA comprises proteins that can be selectively concentrated by an ATP affinity column (Lanes 4 & 9) and react against an anti-HSP antibody. Lanes 3 and 7 show 10 ug of starting material; Lanes 4 and 9 show the fractions after elution and concentration from the ATP affinity column; Lanes 5 and 8 show the wash through after elution with ATP, and lane 10 is a hsp positive control. (See Example 9 for details).

Results: The results are shown in FIG. 11. The Western blot pictured shows that the separation scheme produces two populations of proteins in the A (flow through) and B (ATP binding) fractions. The starting material, (lane 2) the fraction A flow through, (lane 3) fraction C wash, (lane 4) and fraction B (lane 5) were tested for the ability to react to the monoclonal antibody. In addition, a commercially available Hsp70 protein that serves as a positive control was loaded in the last lane (lane 10). As shown in the blot in FIG. 11, the flow through fraction A (lane 3) does not contain significant amounts of Hsp70. The eluted and concentrated fraction B (lane 4) is highly reactive to the antibody as shown in the blot and indicates at least two distinct bands centered around the 75 kDa molecular weight marker. The wash fraction C (lane 5), indicates the presence of two bands that run at slightly below 75 kDa. In a separate independent experiment, the flow through fraction A (lane 7) again is not reactive to the antibody, and the wash fraction C (lane 8) is also not reactive to the antibody, but the fraction enriched in ATP binding proteins (Fraction B) shown in lane 9 gives the same banding pattern as was seen from the first separation.

Discussion: A separation protocol was developed to separate HSP70 proteins based on their ability to bind to ATP agarose affinity resin, and, was tested for its effectiveness. The procedure involved only minimal sample manipulation, using only ATP agarose, and ultrafiltration to concentrate and conduct buffer changes, and an anti-hsp70 antibody to detect the presence of hsps. The results of the procedure (FIG. 11) clearly demonstrates that while in 10 µg of starting material, 10 µg of flow through, or 10 µg of wash fraction there is insufficient hsp70 to be detected by the ant-Hsp antibody. By contrast, the fraction eluted from the ATP agarose column, contains at least two proteins that are clearly recognized by the anti-Hsp70 antibody. The results therefore show that the separation scheme was successful and reproducible on two independent chromatography runs and diafiltrations. Furthermore, the data substantiates the identification of heat shock proteins made by Peptide Mass Finger printing, as discussed earlier, and demonstrates that these proteins are functional and can be readily isolated and enriched by simple ATP agarose chromatography followed with diafiltration. It is concluded that the heat shock proteins co-purify with the recombinant albumin. Such co-purification is consistent with the hypothesis that the heat shock proteins are bound to the albumin, and that the albumin acts to stabilize the heat shock proteins in a stable conformation. Surprisingly, the recombinant albumin/heat shock protein complex retains significant ATPase activity (data not shown) consistent with the presence of function heat shock proteins. This increased activity was further confirmed as providing a growth promoting effect as described below.

Figure 12:
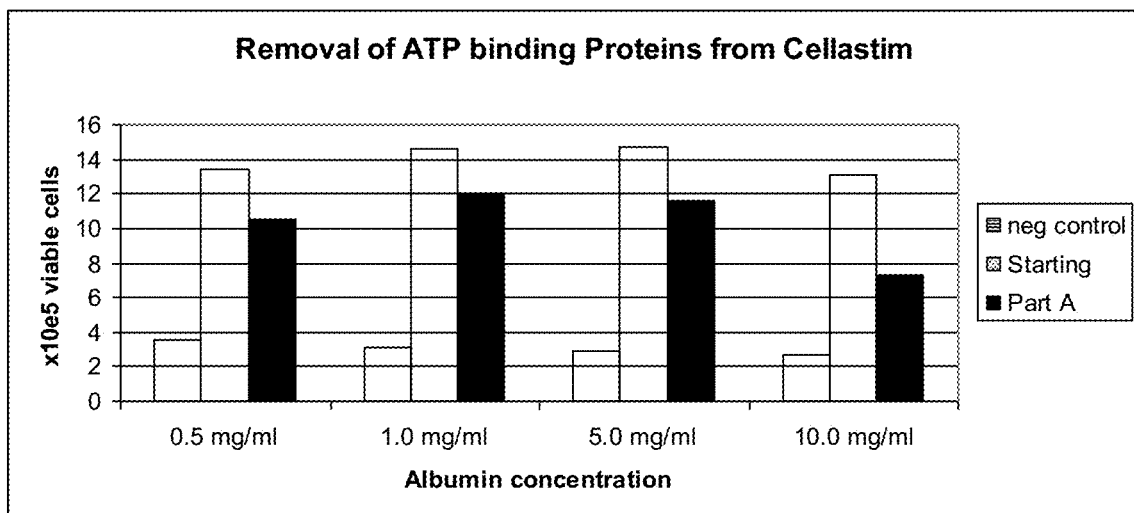
FIG. 12: Shows a comparison of the cell growth and viability effect of Cellastim recombinant albumin after passing the albumin produced using the new process over an ATP affinity column to remove heat shock proteins. (See text for details).

Example 10: Impact of the Removal of Hsps from Rice Recombinant Albumin on Cell Viability Methods: The separation scheme described in Example 9 was also used to produce fraction A suitable for cell culture testing (FIG. 12). The method involves minimal manipulation of fraction A, as it is flowed through an ATP agarose column and then concentrated by diafiltration and buffered with PBS that is suitable for cell culture. The intent of the method is to not introduce new variables into the experiment such that a loss of viability is seen but due to some other reason or cause beyond the removal of ATP binding proteins. Fraction A was tested against the unadulterated control (starting material) for ability to promote hybridoma cell culture viability. The results of the test are shown in FIG. 12.

Results: As shown in FIG. 12 the Cellastim starting material (cross hatched bars), and Part A (solid bars) were tested at the same concentration and compared to the negative control (striped bars). A statistically significant decrease is observable at all four concentrations tested. The result indicates that there was a significant loss in the performance of Cellastim after ATP agarose treatment. The treatment resulted in a 28.0, 21.7, 26.7, and 79.5% loss as compared to Cellastim before removal of ATP binding proteins. In this experiment, care was taken in the design and handling of the samples to ensure that any inadvertent losses in performance due to sample handling or the accidental introduction of new contaminants were minimized.

Discussion: The cell culture results (FIG. 12) demonstrate that it is possible to reduce the performance of the rice derived recombinant albumin by simply passing it over an ATP binding column. This data, when combined with the results shown in Example 9 demonstrates that the depletion of the hsps from albumin by the ATP agarose column directly reduces the cell growth promoting properties of the albumin. This result therefore demonstrates that the superior properties of the albumin arise, at least in part, from the contaminating heat shock proteins in the albumin.

Example 11: Effect of Rice Derived Recombinant Human Serum Albumin in Combination with Lactoferrin on the Proliferation of CHO K1 in Serum Free Culture To investigate whether the unique attributes of plant derived human serum albumin (Cellastim) could positively impact the growth promoting activities of other cell culture components when added in combination with these components, a series of additional experiments were designed to evaluate and identify optimum combinations of such components.

Methods: CHO K1 line DP12 clone 1934 (ATCC #CRL-12445) was maintained in SAFC 325 PF protein free CHO medium supplemented with 0.5% FBS, 1 µM methotrexate, 50 µg/mL penicillin/streptomycin, 1 mM Glutamax (Invitrogen) in 14 ml medium in 125 ml flasks. CHO K1 line DP12 expresses a humanized monoclonal antibody as a secreted product. The growth and productivity enhancing effect of plant derived recombinant human serum albumin (rHSA) (Examples 3 & 5) and plant derived recombinant lactoferrin (rLF) (Examples 1 & 4) alone or in combination were examined. Cells were washed twice in 325 PF CHO medium containing 200 nM methotrexate, 50 µg/mL penicillin/streptomycin and seeded in the same medium into 4 ml shake-batch cultures at $1.5 \times 10^5$ cells/ml. 4 ml shake cultures were further supplemented with various concentrations of rHSA or rLF or various mixtures of the two additives. Control cultures without added rHSA or rLF were used as the baseline. All culture conditions were performed as duplicates. The concentration of viable cells was determined daily for the 14-day batch period via a Guava PCA cell counter (Guava Technologies). Log-phase growth was judged by the relative proliferation of the cells after 6 days of culture. All cultures were grown at 37° C., 6% $CO_2$, in a humidified environment. The Observed Effect was calculated as the net viable cell concentration (observed-base medium). The Predictive Effect was calculated as the sum of the effect of the individual components.

Table E9 shows the number of viable cells after 6 days of culture. Cells in media without supplementation proliferated to $3.3 \times 10^5$ viable cells/ml. Addition of plant derived recombinant human serum albumin (rHSA) or recombinant lactoferrin (rLF), or a combination of the two increased the proliferation of cells as indicated below. Column two shows the Observed Effect of the respective additive(s) above baseline control culture. Column 3 shows the Predicted Effect using a model where the predictive additive effect equals the sum of additive1 and additive2.

TABLE E9

|  | Viable cells($e^5$)/ml | Observed Effect | Predicted Effect | Ratio of Lactoferrin to albumin |
|---|---|---|---|---|
| No Additives (Baseline) | 3.3 | 0 |  |  |
| rHSA 0.5 g/L | 7.3 | 4.0 |  |  |
| rHSA 1 g/L | 7.9 | 4.6 |  |  |
| rLF 0.1 g/L | 7.5 | 4.2 |  |  |
| rLF 0.8 g/L | 16.0 | 12.7 |  |  |
| rLF 0.1 g/L + rHSA 0.5 g/L | 18.9 | 15.6 | 8.2 | 1:5 |
| rLF 0.8 g/L + rHSA 0.5 g/L | 29.0 | 25.7 | 16.7 | 1:0.625 |
| rLF 0.1 g/L + rHSA 1 g/L | 23.6 | 20.3 | 8.8 | 1:10 |
| rLF 0.8 g/L + rHSA 1 g/L | 35.4 | 32.1 | 17.3 | 1:1.25 |

Discussion: Lactoferrin is an essential factor for serum free cell culture media, where it acts to transport iron; additionally Lactoferrin has more recently been identified as a growth factor and inhibitor of apoptosis in some cell types (Huang et al., In vitro Cell. Dev. Biol. Anim. (2008) 44(10) 464-71; Wong et al., Rheumatology 48(1) 39-44; Bi et al., Arch. Immunol. Ther. Exp. (1997)45(4) 315-20; Hashizume et al., Biochem. Biophys. Acta. (1983) 763(4) 377-82). In Table E9, the data shows that the addition of 0.1 g/L and 0.8 g/L recombinant lactoferrin resulted in a significant enhancement of cell growth compared to the baseline rate of cell growth consistent with lactoferrins growth stimulating properties.

The growth stimulating effect of lactoferrin was further enhanced by the addition of plant derived recombinant human serum albumin. Unexpectedly the combination of 0.1 g/L lactoferrin and 0.5 g/L plant derived recombinant human serum albumin (1 to five ratio) resulted in a stimulation in cell growth that was approximately 4 fold higher than either albumin alone or lactoferrin alone tested at the same concentrations. While the combination of 0.1 g/L lactoferrin and 1.0 g/L human serum albumin (1 to 10 ratio) resulted in a stimulation in cell growth that was approximately 4.4 to almost 5 fold higher than either albumin or lactoferrin alone at the same concentrations.

Synergism was also observed when plant derived recombinant human serum albumin was added to the lactoferrin at a concentration of 0.8 g/L. Even at this significantly higher concentration, the addition of plant derived recombinant human serum albumin further increased cell growth by 2 to 2.5 fold.

Albumin and lactoferrin are distinct protein families with little overlapping structural or functional similarity. Thus the fact the synergism was observed with these proteins is unexpected based on their dissimilar structure & function. Synergism provides the opportunity to develop improved supplements that provide for supplements with enhanced cell culturing properties (i.e. improved cell growth and viability) by using optimal ratios of lactoferrin and albumin.

Example 12: Effect of Rice Derived Recombinant Albumin in Combination with Lactoferrin on the Productivity of CHO K1 Cells Grown in Serum Free Culture Methods: CHO K1 line DP12 clone 1934 (ATCC #CRL-12445) was maintained in SAFC 325 PF protein free CHO medium supplemented with 0.5% FBS, 1 µM methotrexate, 50 µg/mL penicillin/streptomycin, 1 mM Glutamax (Invitrogen) in 14 ml medium in 125 ml flasks. CHO K1 line DP12 expresses a humanized monoclonal antibody as a secreted product. The growth and productivity enhancing effect of plant derived recombinant human serum albumin (rHSA) (Examples 3 & 5) and plant derived recombinant lactoferrin (rLF) (Examples 1 & 4) alone or in combination were examined. Cells were washed twice in 325 PF CHO medium containing 200 nM methotrexate, 50 µg/mL penicillin/streptomycin and seeded in the same medium into 4 ml shake-batch cultures at $1.5 \times 10^5$ cells/ml. 4 ml shake cultures were further supplemented with various concentrations of plant derived recombinant human serum albumin or LF or various mixtures of the two additives. Control cultures without added HSA or LF were used as the baseline. All culture conditions were performed as duplicates. The concentration of viable cells was determined daily for the 14-day batch period via a Guava PCA cell counter (Guava Technologies). Log-phase growth was judged by the relative proliferation of the cells after 6 days of culture. Antibody productivity was determined at the end of the batch culture when cell viability had declined to <10% (typically day 13 or 14) by quantitative ELISA (Bethyl Laboratories). All cultures were grown at 37° C., 6% $CO_2$, in a humidified environment. The Observed effect was calculated as the net viable cell concentration (observed-base medium). The Predictive Effect was calculated as the sum of the effect of the individual components.

TABLE E10

|  | Product Conc. (µg/ml) | Observed Effect | Predicted Effect | Ratio of HSA to Lactoferrin |
| --- | --- | --- | --- | --- |
| No Additives (Baseline) | 47.1 | 0 | | |
| rHSA 0.5 g/L | 114.6 | 67.5 | | |
| rHSA 1 g/L | 136.1 | 89.0 | | |
| rLF 0.1 g/L | 91.9 | 44.8 | | |
| rLF 0.8 g/L | 138.5 | 91.4 | | |
| rLF 0.1 g/L + rHSA 0.5 g/L | 183.7 | 136.6 | 112.3 | 1:5 |
| rLF 0.8 g/L + rHSA 0.5 g/L | 242.1 | 195.0 | 158.9 | 1:0.625 |
| rLF 0.1 g/L + rHSA 1 g/L | 219.3 | 172.2 | 133.8 | 1:10 |
| rLF 0.8 g/L + rHSA 1 g/L | 260.2 | 213.1 | 180.4 | 1:1.25 |

Table E10 shows the effect of plant derived recombinant human serum albumin and recombinant lactoferrin produced in monocot cells, and various combinations of the two proteins on the productivity of CHO K1 cells. Table E10 shows that the concentration of antibody product produced by the cells after 13 days of culture in the baseline medium (with no additives) produced 47.1 µg/ml of antibody product. Medium supplemented with recombinant albumin or recombinant lactoferrin alone or a combination of plant derived recombinant human serum albumin and lactoferrin produced significantly higher levels of antibody than the control medium with no additives. Column 2 shows the Observed Effect of the additive(s) over the baseline control medium. Column 3 shows the predictive additive effect of the combination of two additives using a model where the predictive additive equals the sum of each additive alone at the same concentration.

Discussion: Table E10 demonstrates that improvements in cell growth and viability directly translated into improved antibody expression and cell productivity. As was the case for cell viability and cell growth, maximal effects of the protein components was observed when these were added to the culture together.

Table E11 shows an additional data set showing the effect of the additives at an expanded range of concentrations, using the same conditions as in Example 12. Medium supplemented with recombinant albumin alone, or lactoferrin alone, or a combination of both proteins, produced higher levels of antibody than the control medium with no additives. Column 2 shows the Observed Effect of the additive(s) over the baseline control medium. Column 3 shows the Predicted Effect of the combination of two additives using a model where the Predicted Effect equals the sum of the effects of each additive when added alone at the same concentration. The data indicates that the actual effect of the combination is greater than the Predicted Effect over all of the ratios of the two proteins tested.

TABLE E11

|  | Product Conc. (µg/ml) | Observed Effect | Predicted Effect | % Improvement over predicted activity | Ratio of Lactoferrin to HSA |
| --- | --- | --- | --- | --- | --- |
| No additives (Baseline) | 56.9 | 0.0 | | | |
| Single additives | | | | | |
| HSA 0.5 g/L | 99.1 | 42.2 | | | |
| HSA 1 g/L | 126.3 | 69.4 | | | |
| HSA 2 g/L | 186.0 | 129.1 | | | |
| HSA 3 g/L | 212.9 | 156.0 | | | |
| LF 0.1 g/L | 123.1 | 66.2 | | | |
| LF 0.5 g/L | 173.5 | 116.6 | | | |
| LF 0.8 g/L | 182.0 | 125.1 | | | |
| LF 1.5 g/L | 196.3 | 139.4 | | | |
| Combinations | | | | | |
| LF 0.1 g/L + HSA 0.5 g/L | 212.4 | 155.5 | 108.5 | 143% | 1:5 |
| LF 0.5 g/L + HSA 0.5 g/L | 314.9 | 258.0 | 158.9 | 163% | 1:1 |
| LF 0.8 g/L + HSA 0.5 g/L | 302.8 | 245.9 | 167.4 | 147% | 1:0.625 |
| LF 1.5 g/L + HSA 0.5 g/L | 336.8 | 279.9 | 181.7 | 154% | 1:0.33 |
| LF 0.1 g/L + HSA 1.0 g/L | 239.7 | 182.8 | 135.7 | 133 | 1:10 |
| LF 0.5 g/L + HSA 1.0 g/L | 339.4 | 282.5 | 186.1 | 152 | 1:2 |
| LF 0.8 g/L + HSA 1.0 g/L | 357.7 | 300.8 | 194.6 | 155 | 1:1.2 |
| LF 1.5 g/L + HSA 1.0 g/L | 343.7 | 286.8 | 208.9 | 137 | 1:0.66 |
| LF 0.1 g/L + HSA 2.0 g/L | 261.3 | 204.4 | 195.4 | 105 | 1:20 |
| LF 0.5 g/L + HSA 2.0 g/L | 377.2 | 320.3 | 245.8 | 131 | 1:4 |
| LF 0.8 g/L + HSA 2.0 g/L | 414.8 | 357.9 | 254.3 | 141 | 1:2.4 |
| LF 1.5 g/L + HSA 2.0 g/L | 358.0 | 301.1 | 268.6 | 112 | 1:1.33 |

Discussion: Ratios of lactoferrin to albumin as low as 1 to 0.333 to as high as 1:20 produced synergistic stimulations of cell growth. Optimal ratios of lactoferrin to albumin were found at 1 to 0.333 wt/wt (at an albumin concentration of 0.5 g/L); at 1 to 1.2 wt/wt (at an albumin concentration of 1.0 g/L); and at 1:2.4 wt/wt (at an albumin concentration of 2.0 g/L).

Thus the stimulation of cell productivity occurs over a broad range of ratios of recombinant albumin and lactoferrin. Optimal ratios of lactoferrin and recombinant albumin vary to a certain extend on the absolute concentration of both protein components. Preferred ratios of Lactoferrin to Albumin range from about 1 (lactoferrin) to 0.33 (albumin) to about 1 (lactoferrin) to 3 (albumin) wt/wt.

Example 13: Evaluation of the Effect of Combinations of Albumin and Transferrin in the Presence of Other Cell Culture Components To determine the effect of other cell culture components on the synergistic effect of lactoferrin and albumin on cell growth and viability, a series of additional experiments were carried out with other cell culture components which have been previously shown to be essential for cell growth in serum free conditions.

Methods: Hybridoma cells actively growing in DMEM/F12 medium with 10% FBS were washed three times in DMEM/F12 without FBS to remove FBS. The growth and productivity enhancing effect of plant derived transferrin plant derived human recombinant serum albumin, sodium selenite and ethanolamine alone and in combination was examined on cells which were seeded into DMEM/F12 at an initial cell density of $0.4 \times 10^5$ viable cells/mL. In these experiments transferrin (TF) was used at an initial concentration of 5.5 µg/mL; Plant derived recombinant Human Serum Albumin (HSA) was used at initial concentrations of 100 µg/mL, 500 µg/mL, and 1000 µg/mL & Sodium Selenite (SE) and Ethanolamine were used at concentrations of 1:500,000 v/v and 6.7 µg/mL respectively. The Observed effect was calculated as the net viable cell concentration (observed-base medium). The Predictive Effect was calculated as the sum of the effect of the individual components.

Shake cultures were further supplemented with various concentrations of the supplements listed above, as described in Table E12 below. Control cultures without added supplements were used as the baseline. All culture conditions were performed as duplicates. The concentration of viable cells was determined after 3 days via a Guava PCA cell counter (Guava Technologies). All cultures were grown at 37° C., 6% $CO_2$, in a humidified environment.

Selenium is a well known essential trace element for cell growth and development, and its positive role in biological systems includes detoxification of free radicals by activating glutathione peroxidase. Additionally selenium can act as a highly effective iron carrier in serum free media, which helps to explain its synergistic impact on transferrin stimulated cell growth. (Zhang et al., Biotechnol. Bioeng. (2006) 95(6) 1188-97).

Example 14: Evaluation of the Effect of Combinations of Albumin, Transferrin and Insulin Methods: Hybridoma cells actively growing in DMEM/F12 medium with 10% FBS were washed three times in DMEM/F12 without FBS to remove FBS. The growth and productivity enhancing effect of plant derived transferrin, plant derived human recombinant serum albumin, sodium selenite and ethanolamine alone and in combination with insulin was examined on cells which were seeded into DMEM/F12 at an initial cell density of $0.4 \times 10^5$ viable cells/mL. In these experiments recombinant human Insulin (IN) (Millipore) was used at a concentration of 10 µg/mL, transferrin (TF) was used at an initial concentration of 5.5 µg/mL; plant derived recombinant Human Serum Albumin was used at initial concentrations of 0.1 g/L, 0.5 g/L, and 1 g/L & Sodium Selenite and Ethanolamine were used at concentrations of 6.7 µg/mL and 1:500,000 v/v and respectively. The Observed effect was calculated as the net viable

TABLE E12

|  | Viable cells/ml | Std | Observed Effect | Predicted Effect | Synergistic | Ratio of transferrin to albumin |
|---|---|---|---|---|---|---|
| DMEM/F12 alone | 0.01 | 0.01 |  |  |  |  |
| 10% FBS | 11.40 | 0.71 | 11.39 |  |  |  |
| TF 5.5 µg/L | 0.02 | 0.00 | 0.01 |  |  |  |
| SE 6.7 µg/L | 0.22 | 0.13 | 0.21 |  |  |  |
| HSA 0.1 g/L | 2.31 | 0.06 | 2.30 |  |  |  |
| HSA 0.5 g/L | 4.67 | 0.18 | 4.66 |  |  |  |
| HSA 1 g/L | 4.55 | 0.46 | 4.54 |  |  |  |
| doubles |  |  |  |  |  |  |
| TF + SE | 0.40 | 0.04 | 0.38 | 0.21 | yes |  |
| TF + HSA 0.1 g/L | 3.00 | 0.02 | 2.98 | 2.30 | yes | 1:18 |
| TF + HSA 0.5 g/l | 5.42 | 0.20 | 5.41 | 4.67 | yes | 1:90 |
| TF + HSA 1 g/L | 5.71 | 0.14 | 5.69 | 4.55 | yes | 1:181 |
| doubles |  |  |  |  |  |  |
| SE + HSA 0.1 g/l | 2.76 | 0.06 | 2.75 | 2.50 | Yes/no |  |
| SE + HSA 0.5 g/L | 4.15 | 0.16 | 4.14 | 4.87 | no |  |
| SE + HSA 1 g/L | 3.75 | 0.22 | 3.74 | 4.75 | no |  |
| Triples |  |  |  |  |  |  |
| TF + SE + HSA 0.1 g/L | 7.40 | 0.00 | 7.39 | 2.51 | yes | 1:18 |
| TF + SE + HSA 0.5 g/L | 9.48 | 0.31 | 9.46 | 4.87 | yes | 1:90 |
| TF + SE + HSA 1 g/L | 9.71 | 0.11 | 9.70 | 4.75 | yes | 1:181 |

Discussion: Recombinant human serum albumin in combination with recombinant transferrin showed synergistic effects when added to culture media together. This effect was further augmented in the presence of selenium. However the addition of selenium did not act synergistically with recombinant plant derived human serum albumin alone. Maximal synergistic effects of transferrin and plant derived recombinant human serum albumin occurred in the presence of selenium and at ratios of transferrin to plant derived recombinant human serum albumin of about 1 (transferrin) to 100 (albumin) wt/wt, and of about 1 (transferrin) to 200 (albumin).

cell concentration (observed-base medium). The Predictive Effect was calculated as the sum of the effect of the individual components.

Shake cultures were further supplemented with various concentrations of the factors listed above, as described in Table E13 below. Control cultures without added supplements were used as the baseline. All culture conditions were performed as duplicates. The concentration of viable cells was determined after 3 days via a Guava PCA cell counter (Guava Technologies). All cultures were grown at 37° C., 6% $CO_2$, in a humidified environment, and shaken with 2 cm rotational orbit at 120 RPM.

TABLE E13

|  | Viable cells/ml | Std | Observed Effect | Predicted Effect | Synergistic |
|---|---|---|---|---|---|
| D/F12 alone | 0.01 | 0.01 | | | |
| 10% FBS | 11.65 | 0.21 | 11.64 | | |
| Factors Alone | | | | | |
| Insulin (IN) 10 µg/L | 0.04 | 0.02 | 0.03 | | |
| Transferrin (TF) 5.5 µg/L | 0.02 | 0.00 | 0.01 | | |
| Sodium Selenite (SE) 6.7 µg/L | 0.22 | 0.13 | 0.21 | | |
| HSA 0.1 g/L | 2.31 | 0.06 | 2.30 | | |
| HSA 0.5 g/L | 4.67 | 0.18 | 4.66 | | |
| HSA 1 g/L | 4.55 | 0.46 | 4.54 | | |
| Doubles | | | | | |
| IN + TF | 0.03 | 0.02 | 0.02 | 0.06 | |
| IN + SE | 1.06 | 0.15 | 1.05 | 0.26 | Yes |
| IN + HSA 0.1 g/L | 2.54 | 0.08 | 2.53 | 2.35 | No |
| IN + HSA 0.5 g/L | 3.96 | 0.34 | 3.95 | 4.71 | No |
| IN + HSA 1 g/L | 4.61 | 0.16 | 4.60 | 4.59 | No |
| Triples | | | | | |
| IN + TF + SE | 2.13 | 0.49 | 2.12 | 0.28 | Yes |
| IN + TF + HSA 0.1 g/L | 3.29 | 0.03 | 3.28 | 2.37 | Yes |
| IN + TF + HSA 0.5 g/L | 5.84 | 0.49 | 5.83 | 4.73 | Yes |
| IN + TF + HSA 1 g/L | 6.84 | 0.34 | 6.83 | 4.61 | Yes |
| IN + SE + HSA 0.1 g/L | 2.21 | 0.17 | 2.19 | 2.37 | No |
| IN + SE + HSA 0.5 g/L | 3.41 | 0.21 | 3.39 | 4.73 | No |
| IN + SE + HSA 1 g/L | 3.62 | 0.23 | 3.60 | 4.61 | No |
| Quaternaries | | | | | |
| IN + TF + SE + HSA 0.1 g/L | 7.91 | 0.46 | 7.90 | 2.59 | Yes |
| IN + TF + SE + HSA 0.5 g/L | 9.14 | 0.63 | 9.13 | 4.95 | Yes |
| IN + TF + SE + HSA 1 g/L | 10.07 | 0.67 | 10.05 | 4.83 | Yes |

Discussion: In these studies the addition of insulin and plant derived recombinant human serum albumin did not produce a synergistic effect on cell growth. By contrast the addition of plant derived recombinant human serum albumin and transferrin and insulin did produce a synergistic effect on cell growth.

Example 15: Evaluation of the Effect of Combinations of Albumin, Transferrin and Insulin in the Presence of Selenium Methods: Hybridoma cells actively growing in DMEM/F12 medium with 10% FBS were washed three times in DMEM/F12 without FBS to remove FBS. The growth and productivity enhancing effect of plant derived transferrin (TF), plant derived recombinant human serum albumin, (HSA) insulin, sodium selenite and ethanolamine alone and in combination was examined in base medium containing 6.7 µg/m L Sodium Selenite at $0.4 \times 10^5$ viable cells/mL. In these experiments recombinant human Insulin (IN) (Millipore) was used at a concentration of 10 µg/mL, transferrin (TF) was used at an initial concentration of 5.5 µg/mL; plant derived recombinant human Serum Albumin was used at initial concentrations of 100 µg/mL, 500 µg/mL, and 1000 µg/mL Ethanolamine were used at a concentration of 1:500,000 v/v. The Observed effect was calculated as the net viable cell concentration (observed-base medium). The Predictive Effect was calculated as the sum of the effect of the individual components.

Shake cultures were further supplemented with various concentrations of the factors listed above, as described in Table E14 below. Control cultures without added supplements were used as the baseline. All culture conditions were performed as duplicates. The concentration of viable cells was determined after 3 days via a Guava PCA cell counter (Guava Technologies). All cultures were grown at 37° C., 6% $CO_2$, in a humidified environment.

TABLE E14

| Condition | Viable cell count 10e5 | Std | Observed Effect | Predicted Effect | % Improvement over predicted activity | Synergistic |
|---|---|---|---|---|---|---|
| Base medium of D/F12 + Selenium | 0.08 | 0.04 | 0.00 | | | |
| 10% FBS | 13.20 | 0.28 | 13.12 | | | |
| Insulin | 0.30 | 0.09 | 0.22 | | | |
| Factors Alone | | | | | | |
| TF | 0.27 | 0.04 | 0.19 | | | |
| HSA 0.1 g/L | 2.23 | 0.11 | 2.15 | | | |
| HSA 0.5 g/L | 6.21 | 0.20 | 6.13 | | | |
| HSA 1 g/L | 8.00 | 0.05 | 7.91 | | | |
| doubles | | | | | | |
| IN + TF | 0.48 | 0.02 | 0.40 | 0.41 | | No |
| IN + HSA 0.1 g/L | 1.81 | 0.02 | 1.72 | 2.37 | | No |
| IN + HSA 0.5 g/L | 6.00 | 0.09 | 5.91 | 6.35 | | No |
| IN + HSA 1 g/L | 7.43 | 0.19 | 7.35 | 8.13 | | No |
| doubles | | | | | | |
| TF + HSA 0.1 g/L | 4.29 | 0.04 | 4.20 | 2.34 | 179 | Yes |
| TF + HSA 0.5 g/L | 12.35 | 0.21 | 12.27 | 6.32 | 194 | Yes |
| TF + HSA 1 g/L | 15.48 | 0.71 | 15.39 | 8.1 | 190 | Yes |
| Triples | | | | | | |
| IN + TF + HSA 0.1 g/L | 4.18 | 0.21 | 4.09 | 2.56 | 159 | Yes |
| IN + TF + HSA 0.5 g/L | 13.60 | 0.00 | 13.52 | 6.54 | 206 | Yes |
| IN + TF + HSA 1 g/L | 15.38 | 0.22 | 15.29 | 8.32 | 184 | Yes |

Discussion: Again, as shown in the last experiment, combinations of plant derived recombinant human serum albumin and insulin did not produce a synergistic stimulation of cell growth when these two components were added to the cell culture media together. By comparison synergism was observed between mixtures of plant derived recombinant human serum albumin and transferrin over all concentration ranges tested. Synergism was also observed with plant derived recombinant human serum albumin and transferrin in the presence of insulin.

Example 16: Evaluation of the Effect of Combinations of Albumin and Transferrin in the Presence of Ethanolamine Methods: Hybridoma cells actively growing in DMEM/F12 medium with 10% FBS were washed three times in DMEM/F12 without FBS to remove FBS. The growth and productivity enhancing effect of plant derived transferrin (TF), plant derived recombinant human serum albumin (HSA), insulin, sodium selenite and ethanolamine alone and in combination was examined in base medium containing 1:500,000 Ethanolamine v/v at $0.4 \times 10^5$ viable cells/ml. In these experiments recombinant human Insulin (IN) (Millipore) was used at a concentration of 10 μg/mL, transferrin (TF) was used at an initial concentration of 5.5 μg/mL; plant derived recombinant Human Serum Albumin was used at initial concentrations of 100 μg/mL, 500 μg/mL, and 1000 μg/mL & Sodium Selenite was used at a concentration of 6.7 μg/mL. The Observed effect was calculated as the net viable cell concentration (observed-base medium). The Predictive Effect was calculated as the sum of the effect of the individual components.

Shake cultures were further supplemented with various concentrations of the factors listed above, as described in Table E15 below. Control cultures without added supplements were used as the baseline. All culture conditions were performed as duplicates. The concentration of viable cells was determined after 3 days via a Guava PCA cell counter (Guava Technologies). All cultures were grown at 37° C., 6% $CO_2$, in a humidified environment.

TABLE E15

| Condition | Observed Effect (Viable cells/ml) | Std | Predicted Effect (Viable cells/ml) | Synergistic |
|---|---|---|---|---|
| Base Medium of D/F12 + Ethanolamine | 0.51 | 0.16 | | |
| 10% FBS | 14.45 | 0.64 | | |
| IN | 1.41 | 0.24 | | |
| Factors Alone | | | | |
| TF | 2.08 | 0.15 | | |
| HSA 0.1 g/L | 2.16 | 0.07 | | |
| HSA 0.5 g/L | 5.66 | 0.35 | | |
| HSA 1 g/L | 7.08 | 0.21 | | |
| doubles | | | | |
| IN + TF | 3.12 | 0.11 | 3.48 | No |
| IN + HSA 0.1 g/L | 1.87 | 0.00 | 3.57 | No |
| IN + HSA 0.5 g/L | 4.48 | 0.25 | 7.07 | No |
| IN + HSA 1 g/L | 5.14 | 0.19 | 8.49 | No |
| TF + HSA 0.1 g/L | 6.72 | 0.35 | 4.24 | Yes |
| TF + HSA 0.5 g/L | 12.30 | 0.26 | 7.74 | Yes |
| TF + HSA 1 g/L | 16.20 | 0.65 | 9.16 | Yes |
| Triples | | | | |
| IN + TF + HSA 0.1 g/L | 7.46 | 0.28 | 5.64 | Yes |
| IN + TF + HSA 0.5 g/L | 13.30 | 0.36 | 9.15 | Yes |
| IN + TF + HSA 1 g/L | 16.60 | 0.48 | 10.57 | Yes |

Discussion: Again, as shown in the last experiment, combinations of plant derived recombinant human serum albumin and insulin did not produce a synergistic stimulation of cell growth when these two components were added to the cell culture media together. By comparison synergism was observed between mixtures of plant derived recombinant human serum albumin and transferrin, over all concentration ranges tested. Synergism was also observed with plant derived recombinant human serum albumin and transferrin in the presence of insulin under these conditions.

Surprisingly the combination of Insulin, transferrin and plant derived recombinant human serum albumin produced superior cell growth compared to 10% serum, demonstrating the superior properties of these combinations of proteins.

Example 17: Comparison of Rice Recombinantly Produced Albumin and Plasma Derived Albumin To directly compare the effect of rice derived recombinant human serum albumin (rHSA) to plasma derived serum albumin (pHSA), samples of both were directly compared at two ratios when mixed with rice derived recombinant transferrin for their ability to stimulate cell growth.

Methods: Hybridoma cells were grown in DMEM/F12 (Gibco) in 10% FBS. Cells in log-phase growth were harvested, washed three times in DMEM/F12 to remove FBS, and seeded in either 1) DMEM/F12 base medium, 2) DMEM/F12+sodium selenate base medium or 3) DMEM/F12 base medium at $0.75 \times 10^5$ viable cells/ml. Each base medium was further supplemented with either recombinant transferrin (TF), rice derived recombinant human serum albumin (rHSA), plasma derived human serum albumin (pHSA) or combinations of both transferrin and either form of albumin. After 3 days of incubation at 37° C., 5% $CO_2$, the concentration of viable cells was determined by a Guava PCA cell counter as instructed by the manufacturer. The Observed effect was calculated as the net viable cell concentration (observed-base medium). The Predictive Effect was calculated as the sum of the effect of the individual components. The Effect Factor was calculated as the observed effect divided by the expected effect. Effect factor of 1 is indicative of expected effect (additive). Effect factor >1 is indicative of more than additive or synergistic effect.

In these experiments transferrin (TF) was used at an initial concentrations of 1 and 3 mg/L; albumins were used at concentrations of 5 g/L, Sodium Selenite was used at a concentration of 6.7 μg/L & Ethanolamine was used at 1:500,000 v/v.

TABLE E16

| | Viable cells/ml 10e5 | Std | Observed Effect | Predicted Effect | Effect Factor (actual/expected) |
|---|---|---|---|---|---|
| Base Medium: DMEM/F12 | | | | | |
| Base Medium Components alone | 0.11 | 0.07 | | | |
| rTF 1 mg/L | 0.21 | 0.01 | 0.10 | | |
| rTF 3 mg/L | 0.28 | 0.09 | 0.18 | | |
| pHSA 5 g/L (Seracare) | 11.30 | 0.28 | 11.19 | | |
| rHSA 5 g/L (Cellastim) | 5.11 | 0.02 | 5.00 | | |
| pHSA combinations | | | | | |
| rTF 1 mg/L + pHSA 5 g/L | 12.85 | 0.49 | 12.74 | 11.51 | 1.1 |
| rTF3 mg/L + pHSA 5 g/L | 13.20 | 0.42 | 13.09 | 16.41 | 0.8 |
| rHSA combinations | | | | | |
| rTF1 mg/L + rHSA 5 g/L | 18.80 | 0.71 | 18.69 | 5.31 | 3.5 |
| rTF3 mg/L + rHSA 5 g/L | 18.85 | 0.92 | 18.74 | 5.39 | 3.5 |
| Base Medium: DMEM/F12 | | | | | |
| Base Medium Components alone | 0.04 | 0.02 | | | |
| rTF 1 mg/L | 0.14 | 0.01 | 0.10 | | |
| rTF 3 mg/L | 0.14 | 0.05 | 0.10 | | |
| pHSA 5 g/L | 6.08 | 0.13 | 6.04 | | |
| rHSA 5 g/L | 1.76 | 0.17 | 1.72 | | |
| pHSA combinations | | | | | |
| rTF 1 mg/L + pHSA 5 g/L | 7.46 | 0.49 | 7.42 | 6.22 | 1.2 |
| rTF3 mg/L + pHSA 5 g/L | 7.84 | 0.05 | 7.79 | 7.84 | 1.0 |
| rHSA combinations | | | | | |
| rTF1 mg/L + rHSA 5 g/L | 8.55 | 0.79 | 8.51 | 1.90 | 4.5 |
| rTF3 mg/L + rHSA 5 g/L | 8.37 | 0.23 | 8.33 | 1.90 | 4.4 |
| Base Medium: DMEM/F12 | | | | | |
| Base Medium Components alone | 1.01 | 0.02 | | | |
| rTF 1 mg/L | 3.45 | 0.27 | 2.44 | | |
| rTF 3 mg/L | 3.47 | 0.27 | 2.46 | | |
| pHSA 5 g/L | 13.15 | 0.49 | 12.14 | | |
| rHSA 5 g/L | 3.46 | 0.13 | 2.45 | | |
| pHSA combinations | | | | | |
| rTF 1 mg/L + pHSA 5 g/L | 14.83 | 0.49 | 13.82 | 16.60 | 0.8 |
| rTF3 mg/L + pHSA 5 g/L | 14.57 | 0.12 | 13.56 | 16.61 | 0.8 |
| rHSA combinations | | | | | |
| rTF1 mg/L + rHSA 5 g/L | 17.87 | 1.46 | 16.86 | 6.91 | 2.4 |
| rTF3 mg/L + rHSA 5 g/L | 20.20 | 1.13 | 19.19 | 6.93 | 2.8 |

Discussion: Table E14 shows the results of three independent experiments that confirm that the combinations of TF with rice derived recombinant human serum albumin produced Observed Effect values much greater than the Predicted Effect. By comparison, the combination of plasma-derived HSA and transferrin produced values that were similar to, or less than, the expected effect. Thus the ability of albumin to synergistically enhance the activity of transferrin and lactoferrin appears to be dependent on the source of albumin, rather than being an inherent characteristic of the albumin itself. Specifically the present experiments establish that the synergistic properties of human serum albumin with transferrin related proteins such as transferrin and lactoferrin is an unexpected and surprising property of rice derived recombinant human serum albumin. Significantly the combination of transferrin and plant derived recombinant albumin was more effective in stimulating cell growth than the combination of plasma derived albumin and transferrin, even though plasma derived albumin was more effective at 5 g/L alone than the same concentration of rice derived human serum albumin.

Example 18: Evaluation of Ability of Rice Derived Recombinant Albumin to Stimulate Cell Growth in Combination with Either Plasma Derived or Recombinant Transferrin To directly compare the effect of rice derived recombinant human transferrin (rTF) to plasma derived transferrin (pTF), samples of both were directly compared when mixed with rice derived recombinant human serum albumin for their ability to stimulate cell growth.

Methods: A base medium (BM) was composed that consisted of DMEM/F12+ with Sodium Selenite 0.0067 mg/L, Ethanolamine 1:500,000 v/v. Base medium included human plasma transferrin, pTF at a concentration of 5.5 mg/L in combination with either plasma HSA (pHSA, cell culture grade Seracare) or rice derived recombinant HSA (rHSA). Hybridoma cells in log-phase growth were harvested, washed three times in DMEM/F12 to remove FBS, and seeded in at $0.80 \times 10^5$ viable cells/ml and incubated at 37° C., 6% $CO_2$. The concentration of viable cells was determined daily by a Guava PCA cell counter as instructed by the manufacturer. The concentration of antibody produced by the cells and secreted into the medium was determined on day 6 by quantitative ELISA (Bethyl laboratories). Error bars indicate standard deviation. The production of antibody with the combination of pTF+rHSA was similar to that of DMEM/F12+10% FBS.

Figure 13:
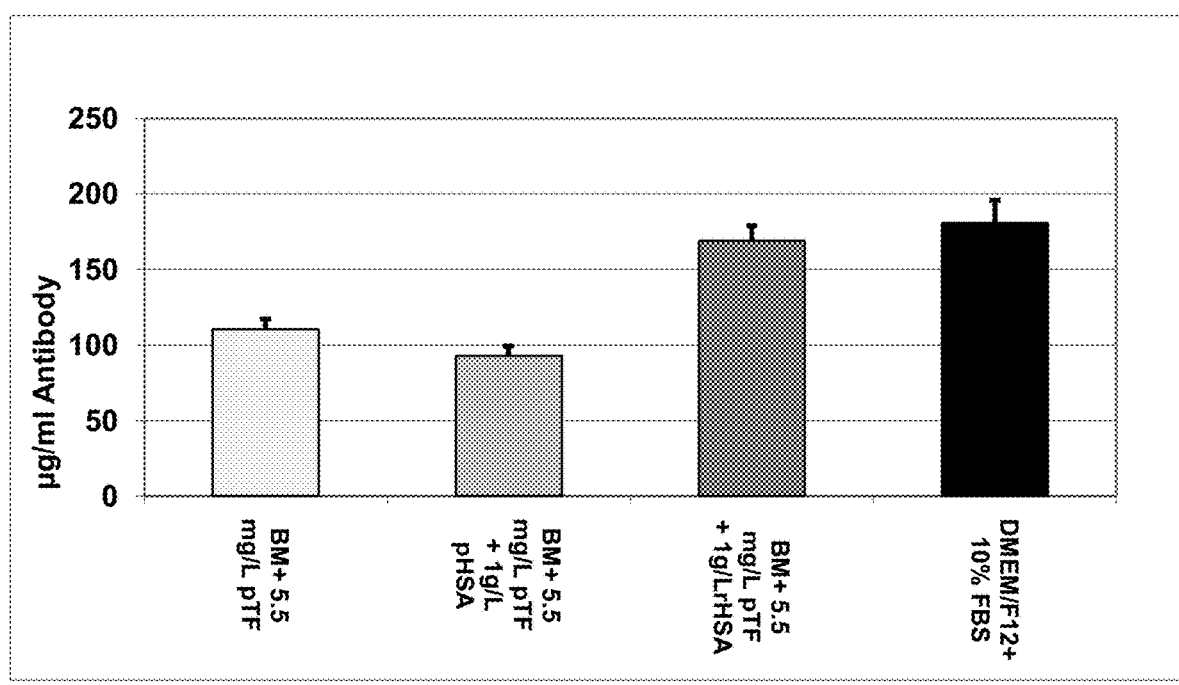
FIG. 13: Shows a comparison of the effect of 1 g/L recombinant plant derived human serum albumin (rHSA) in combination with transferrin (pTF) compared to the same concentration of plasma derived human serum albumin (pHSA) in combination with transferrin (pTF) on the production of antibody by hybridoma cells in culture.

Discussion: FIG. 13 shows that rice derived recombinant human serum albumin was able to act synergistically with plasma derived transferrin to significantly enhance the growth and productivity of the cells. By comparison, plasma derived serum albumin was unable to exert a similar stimulatory effect. Specifically the present experiments establish that the synergistic properties of rice derived human serum albumin are also effective with transferrin related proteins that were either plasma derived, or recombinant.

Example 19: Evaluation of Ability of Rice Derived Recombinant Albumin to Stimulate Cell Growth in Combination with Insulin Related Growth Factor-1

To investigate whether the unique attributes of plant derived human serum albumin (Cellastim) could positively impact the growth promoting activities of other cell culture components such as the growth factor IGF-1, additional experiments were performed to assess this possibility.

Methods: CHO K1 line DP12 clone 1934 (ATCC #CRL-12445) was maintained in SAFC 325 PF protein free CHO medium supplemented with 0.5% FBS, 1 µM methotrexate, 50 µg/mL penicillin/streptomycin, 1 mM Glutamax (Invitrogen) as described previously. The growth and productivity enhancing effect of plant derived recombinant human serum albumin (rHSA) (Examples 3 & 5) and recombinant insulin related growth factor 1 (IGF1) (Ajinomoto) alone or in combination were examined. Cells were washed twice in 325 PF CHO medium containing 200 nM methotrexate, 50 µg/mL penicillin/streptomycin and seeded in the same medium into 4 ml shake-batch cultures at $1.5 \times 10^5$ cells/ml. 4 ml shake cultures were further supplemented with various concentrations of rHSA or IGF-1 or various mixtures of the two additives. Control cultures without added rHSA or IGF-1 were used as the baseline. All culture conditions were performed as duplicates. The concentration of viable cells was determined daily for the 14-day batch period via a Guava PCA cell counter (Guava Technologies). Log-phase growth was judged by the relative proliferation of the cells after 6 days of culture. All cultures were grown at 37° C., 6% $CO_2$, in a humidified environment. Table E17 shows the results of the experiment. Here the Observed Effect was calculated as the net viable cell concentration (observed-base medium), and the Predictive Effect was calculated as the sum of the effect of the individual components.

TABLE E17

| | viable cells/ml 10e5 | Observed Effect (Cell count-baseline) | Predicted Effect |
|---|---|---|---|
| No Additive(baseline) | 3.3 | 0.0 | |
| HSA 0.5 g/L | 7.3 | 4.0 | |
| HSA 1 g/L | 7.9 | 4.6 | |
| IGF-1 30 nM | 12.0 | 8.7 | |
| HSA 0.5 g/L + IGF-1 30 nM | 23.5 | 15.6 | 12.7 |
| HSA 1 g/L + IGF-1 30 nM | 25.6 | 13.6 | 13.3 |

Results and Discussion: Table E17 shows that rice derived recombinant human serum albumin was able to act synergistically with recombinant IGF-1 to significantly enhance the growth and productivity of the cells. By comparison, recombinant albumin did not act synergistically with insulin (Table E15) suggesting that synergism is not a general effect across all cell culture components. Specifically the present experiments establish that the synergistic properties of rice derived human serum albumin are also effective in combination with IGF-1.

It will, of course, be appreciated that the above description has been given by way of example only and that modifications in detail may be made within the scope of the present invention.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

The invention claimed is:

1. A method for enhancing cell growth in culture, said method comprising:
    a) culturing cells in a cell culture media supplemented with a plant-produced recombinant mammalian albumin supplement, wherein said plant-produced recombinant mammalian albumin has less than 1 EU of endotoxin/mg of albumin and less than 2% aggregated albumin, wherein said cell growth in culture is enhanced relative to a culture without said plant-produced recombinant mammalian albumin supplement.

2. The method of claim 1, wherein said cell culture media is fetal bovine serum-free media.

3. The method of claim 1, wherein said albumin is recombinant human serum albumin.

4. The method of claim 1, wherein said plant-produced recombinant mammalian albumin supplement is a transgenic grain extract.

5. The method of claim 4, wherein the transgenic grain is transgenic rice.

6. The method of claim 1, wherein said plant-produced recombinant mammalian albumin supplement is added to said cell culture media at day 0 of said culturing.

7. The method of claim 1, wherein said plant-produced recombinant mammalian albumin supplement is added to said cell culture media before day 4 of said culturing.

8. The method of claim 1, wherein said plant-produced recombinant mammalian albumin supplement is added to said cell culture media daily during said culturing.

9. The method of claim 1, wherein said recombinant mammalian albumin comprises at least 0.01% wt/wt of a heat shock protein.

10. The method of claim 9, wherein said heat shock protein is a rice heat shock protein.

11. The method of claim 10, wherein said heat shock protein is selected from the group consisting of Rice HSP70 proteins, and homologs thereof selected from the group consisting of rice endosperm lumenal binding protein (Bip homolog) and rice stromal protein.

12. The method of claim 11, wherein said supplement comprises at least 0.04% wt/wt HSP70.

13. The method of claim 10, wherein said heat shock protein is selected from the group consisting of Rice (gb|ACJ54890.1|), EEC69073/OsI_37938, and AAB63469.

14. The method of claim 1, further comprising a recombinant transferrin related protein, wherein said transferrin related protein is lactoferrin.

15. The method of claim 14, wherein said ratio of said lactoferrin to said recombinant mammalian albumin is 1:3 to 1:0.33.

16. The method of claim 1, further comprising a recombinant transferrin related protein, wherein said transferrin related protein is transferrin.

17. The method of claim 16, wherein said ratio of said transferrin to said recombinant mammalian albumin is 1:50 to 1:5000.

18. The method of claim 3, wherein said plant-produced recombinant human serum albumin is an expression product of a transgenic monocot plant.

19. The method of claim 18, wherein said transgenic monocot plant is a transgenic rice plant (Oryza sativa).

20. The method of claim 19, wherein said plant-produced recombinant human serum albumin is a seed protein extract from a rice seed of said transgenic rice plant.

21. The method of claim 19, wherein said cell culture media is further supplemented with rice heat shock protein.

22. The method of claim 21, wherein said rice heat shock protein is a seed protein extract from a rice seed of said transgenic rice plant.

23. The method of claim 21, wherein said rice heat shock protein is co-purified from said transgenic rice plant with said plant-produced recombinant human serum albumin.

24. The method of claim 18, wherein said plant-produced recombinant human serum albumin has a purity of greater than about 95% as measured by SDS-PAGE.

25. The method of claim 1, wherein said cells are selected from the group consisting of tissue culture cells, CHO cells, hybridoma cells, VERO cells, stem cells, B-cells, T-cells, B-cell derived cells, and T-cell derived cells.

26. The method of claim 1, further comprising culturing said cells having enhanced growth for in vitro fertilization, testing an effect of a compound or drug on said cells, synthesizing biologics, propagation and differentiation of stem cells, vaccine production, or tissue engineering.

* * * * *

SEQUENCE LISTING

<160> NUMBER OF SEQ ID NOS: 12

<210> SEQ ID NO 1
<211> LENGTH: 609
<212> TYPE: PRT
<213> ORGANISM: Homo sapiens

<400> SEQUENCE: 1

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
```

```
            210                 215                 220
Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
            370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu
```

<210> SEQ ID NO 2
<211> LENGTH: 60

```
<212> TYPE: PRT
<213> ORGANISM: Artificial Sequence
<220> FEATURE:
<223> OTHER INFORMATION: Synthetic protein sequence

<400> SEQUENCE: 2

Ala Thr Ala Gly Asp Thr His Leu Gly Gly Glu Asp Phe Asp Asn Arg
1               5                   10                  15

Val Val Pro Gly Pro Ala Asp Lys Ser Pro Met Ile Val Val Thr Tyr
            20                  25                  30

Lys Gly Glu Glu Lys Asn Ala Val Ile Thr Val Pro Ala Tyr Phe Asn
        35                  40                  45

Asp Ser Gln Arg Ile Ile Asn Glu Pro Thr Ala Ala
    50                  55                  60

<210> SEQ ID NO 3
<211> LENGTH: 93
<212> TYPE: PRT
<213> ORGANISM: Artificial Sequence
<220> FEATURE:
<223> OTHER INFORMATION: Synthetic Sequence

<400> SEQUENCE: 3

Asn Gln Ala Ala Val Asn Pro Glu Arg Asn Gly His Val Glu Ile Ile
1               5                   10                  15

Ala Asn Asp Gln Gly Asn Arg Ile Val Asn Lys Asp Gly Lys Pro Tyr
            20                  25                  30

Ile Gln Val Lys Ile Ile Asn Glu Pro Thr Ala Ala Ala Ile Ala Tyr
        35                  40                  45

Gly Leu Asp Lys Lys Lys Leu Gly Thr Val Ile Gly Ile Asp Leu Gly
    50                  55                  60

Thr Thr Tyr Ser Cys Val Gly Val Tyr Lys Val Glu Ile Glu Ser Leu
65                  70                  75                  80

Phe Asp Gly Thr Asp Ser Phe Ser Glu Pro Leu Thr Arg
                85                  90

<210> SEQ ID NO 4
<211> LENGTH: 56
<212> TYPE: PRT
<213> ORGANISM: Artificial Sequence
<220> FEATURE:
<223> OTHER INFORMATION: Synthetic Sequence

<400> SEQUENCE: 4

Asn Gln Ala Asp Ser Val Val Tyr Gln Thr Glu Lys Lys Gln Asp Ile
1               5                   10                  15

Thr Ile Thr Gly Ala Ser Thr Leu Pro Lys Asp Glu Val Glu Arg Asp
            20                  25                  30

Val Val Leu Leu Asp Val Thr Pro Leu Ser Leu Ser Leu Gly Leu Glu
        35                  40                  45

Thr Leu Gly Gly Val Met Thr Lys
    50                  55

<210> SEQ ID NO 5
<211> LENGTH: 653
<212> TYPE: PRT
<213> ORGANISM: Oryza sativa

<400> SEQUENCE: 5

Met Ala Gly Asn Lys Gly Glu Gly Pro Ala Ile Gly Ile Asp Leu Gly
1               5                   10                  15
```

```
Thr Thr Tyr Ser Cys Val Gly Val Trp Gln His Asp Arg Val Glu Ile
            20                  25                  30

Ile Ala Asn Asp Gln Gly Asn Arg Thr Thr Pro Ser Tyr Val Ala Phe
        35                  40                  45

Thr Asp Thr Glu Arg Leu Ile Gly Asp Ala Ala Lys Asn Gln Val Ala
50                  55                  60

Met Asn Pro Thr Asn Thr Val Phe Asp Ala Lys Arg Leu Ile Gly Arg
65                  70                  75                  80

Arg Phe Ser Asp Pro Ser Val Gln Ala Asp Met Lys Met Trp Pro Phe
                85                  90                  95

Lys Val Val Pro Gly Pro Ala Asp Lys Pro Met Ile Val Val Thr Tyr
                100                 105                 110

Lys Gly Glu Glu Lys Lys Phe Ser Ala Glu Glu Ile Ser Ser Met Val
            115                 120                 125

Leu Thr Lys Met Lys Glu Ile Ala Glu Ala Phe Leu Ser Thr Thr Ile
    130                 135                 140

Lys Asn Ala Val Ile Thr Val Pro Ala Tyr Phe Asn Asp Ser Gln Arg
145                 150                 155                 160

Gln Ala Thr Lys Asp Ala Gly Val Ile Ser Gly Leu Asn Val Met Arg
                165                 170                 175

Ile Ile Asn Glu Pro Thr Ala Ala Ala Ile Ala Tyr Gly Leu Asp Lys
                180                 185                 190

Lys Ala Ala Ser Thr Gly Glu Lys Asn Val Leu Ile Phe Asp Leu Gly
            195                 200                 205

Gly Gly Thr Phe Asp Val Ser Ile Leu Thr Ile Glu Glu Gly Ile Phe
        210                 215                 220

Glu Val Lys Ala Thr Ala Gly Asp Thr His Leu Gly Gly Glu Asp Phe
225                 230                 235                 240

Asp Asn Arg Met Val Asn His Phe Val Gln Glu Phe Lys Arg Lys His
                245                 250                 255

Lys Lys Asp Ile Thr Gly Asn Pro Arg Ala Leu Arg Arg Leu Arg Thr
                260                 265                 270

Ala Cys Glu Arg Ala Lys Arg Thr Leu Ser Ser Thr Ala Gln Thr Thr
            275                 280                 285

Ile Glu Ile Glu Ser Leu Tyr Glu Gly Ile Asp Phe Tyr Ala Thr Ile
        290                 295                 300

Thr Arg Ala Arg Phe Glu Glu Leu Asn Met Asp Leu Phe Arg Arg Cys
305                 310                 315                 320

Met Glu Pro Val Glu Lys Cys Leu Arg Asp Ala Lys Met Asp Lys Ala
                325                 330                 335

Gln Ile His Asp Val Val Leu Val Gly Gly Ser Thr Arg Ile Pro Lys
                340                 345                 350

Val Gln Gln Leu Leu Gln Asp Phe Phe Asn Gly Lys Glu Leu Cys Lys
            355                 360                 365

Ser Ile Asn Pro Asp Glu Ala Val Ala Tyr Gly Ala Ala Val Gln Ala
    370                 375                 380

Ala Ile Leu Ser Gly Glu Gly Asn Gln Arg Val Gln Asp Leu Leu Leu
385                 390                 395                 400

Leu Asp Val Thr Pro Leu Ser Leu Gly Leu Glu Thr Ala Gly Gly Val
                405                 410                 415

Met Thr Val Leu Ile Pro Arg Asn Thr Thr Ile Pro Thr Lys Lys Glu
                420                 425                 430
```

```
Gln Val Phe Ser Thr Tyr Ser Asp Asn Gln Pro Gly Val Leu Ile Gln
            435                 440                 445

Val Tyr Glu Gly Glu Arg Thr Arg Thr Lys Asp Asn Asn Leu Leu Gly
450                 455                 460

Lys Phe Glu Leu Thr Gly Ile Pro Pro Ala Pro Arg Gly Val Pro Gln
465                 470                 475                 480

Ile Asn Val Thr Phe Asp Ile Asp Ala Asn Gly Ile Leu Asn Val Ser
            485                 490                 495

Ala Glu Asp Lys Thr Thr Gly Lys Lys Asn Lys Ile Thr Ile Thr Asn
            500                 505                 510

Asp Lys Gly Arg Leu Ser Lys Glu Glu Ile Glu Arg Met Val Gln Glu
            515                 520                 525

Ala Glu Lys Tyr Lys Ala Glu Asp Glu Gln Val Arg His Lys Val Glu
            530                 535                 540

Ala Arg Asn Ala Leu Glu Asn Tyr Ala Tyr Asn Met Arg Asn Thr Val
545                 550                 555                 560

Arg Asp Glu Lys Ile Ala Ser Lys Leu Pro Ala Asp Asp Lys Lys Lys
                    565                 570                 575

Ile Glu Asp Ala Ile Glu Asp Ala Ile Lys Trp Leu Asp Gly Asn Gln
            580                 585                 590

Leu Ala Glu Ala Asp Glu Phe Glu Asp Lys Met Lys Glu Leu Glu Ser
            595                 600                 605

Leu Cys Asn Pro Ile Ile Ser Lys Met Tyr Gln Gly Gly Ala Gly Gly
            610                 615                 620

Pro Ala Gly Met Asp Glu Asp Ala Pro Asn Gly Ser Ala Gly Thr Gly
625                 630                 635                 640

Gly Gly Ser Gly Ala Gly Pro Lys Ile Glu Glu Val Asp
                    645                 650

<210> SEQ ID NO 6
<211> LENGTH: 663
<212> TYPE: PRT
<213> ORGANISM: Oryza sativa

<400> SEQUENCE: 6

Met Asp Arg Val Arg Gly Ser Ala Phe Leu Leu Gly Val Leu Leu Ala
1               5                   10                  15

Gly Ser Leu Phe Ala Phe Ser Val Ala Lys Glu Glu Thr Lys Lys Leu
            20                  25                  30

Gly Thr Val Ile Gly Ile Asp Leu Gly Thr Thr Tyr Ser Cys Val Gly
            35                  40                  45

Val Tyr Lys Asn Gly His Val Glu Ile Ile Ala Asn Asp Gln Gly Asn
50                  55                  60

Arg Ile Thr Pro Ser Trp Val Ala Phe Thr Asp Ser Glu Arg Leu Ile
65                  70                  75                  80

Gly Glu Ala Ala Lys Asn Gln Ala Ala Val Asn Pro Glu Arg Thr Ile
                    85                  90                  95

Phe Asp Val Lys Arg Asp Ile Gly Arg Lys Phe Glu Glu Lys Glu Val
            100                 105                 110

Gln Arg Asp Met Lys Leu Val Pro Tyr Lys Ile Val Asn Lys Ile Gly
            115                 120                 125

Lys Pro Tyr Ile Gln Val Lys Ile Lys Asp Gly Glu Asn Lys Val Phe
            130                 135                 140

Ser Pro Glu Glu Val Ser Ala Met Ile Leu Gly Lys Met Lys Glu Thr
145                 150                 155                 160
```

```
Ala Glu Ala Tyr Leu Gly Lys Lys Ile Asn Asp Ala Val Val Thr Val
                165                 170                 175

Pro Ala Tyr Phe Asn Asp Ala Gln Arg Gln Ala Thr Lys Asp Ala Gly
            180                 185                 190

Val Ile Ala Gly Leu Asn Val Ala Arg Ile Ile Asn Glu Pro Thr Ala
        195                 200                 205

Ala Ala Ile Ala Tyr Gly Leu Asp Lys Lys Gly Gly Glu Lys Asn Ile
    210                 215                 220

Leu Val Phe Asp Leu Gly Gly Gly Thr Phe Asp Val Ser Ile Leu Thr
225                 230                 235                 240

Ile Asp Asn Gly Val Phe Glu Val Leu Ala Thr Asn Gly Asp Thr His
                245                 250                 255

Leu Gly Gly Glu Asp Phe Asp Gln Arg Ile Met Glu Tyr Phe Ile Lys
            260                 265                 270

Leu Ile Lys Lys Lys Tyr Ser Lys Asp Ile Ser Lys Asp Asn Arg Ala
        275                 280                 285

Leu Gly Lys Leu Arg Arg Glu Ala Glu Arg Ala Lys Arg Ala Leu Ser
    290                 295                 300

Asn Gln His Gln Val Arg Val Glu Ile Glu Ser Leu Phe Asp Gly Thr
305                 310                 315                 320

Asp Phe Ser Glu Pro Leu Thr Arg Ala Arg Phe Glu Glu Leu Asn Asn
                325                 330                 335

Asp Leu Phe Arg Lys Thr Met Gly Pro Val Lys Lys Ala Met Asp Asp
            340                 345                 350

Ala Gly Leu Glu Lys Ser Gln Ile His Glu Ile Val Leu Val Gly Gly
        355                 360                 365

Ser Thr Arg Ile Pro Lys Val Gln Gln Leu Leu Arg Asp Tyr Phe Glu
    370                 375                 380

Gly Lys Glu Pro Asn Lys Gly Val Asn Pro Asp Glu Ala Val Ala Tyr
385                 390                 395                 400

Gly Ala Ala Val Gln Gly Ser Ile Leu Ser Gly Gly Gly Asp Glu
                405                 410                 415

Thr Lys Asp Ile Leu Leu Leu Asp Val Ala Pro Leu Thr Leu Gly Ile
            420                 425                 430

Glu Thr Val Gly Gly Val Met Thr Lys Leu Ile Pro Arg Asn Thr Val
        435                 440                 445

Ile Pro Thr Lys Lys Ser Gln Val Phe Thr Thr Tyr Gln Asp Gln Gln
    450                 455                 460

Thr Thr Val Ser Ile Gln Val Phe Glu Gly Glu Arg Ser Met Thr Lys
465                 470                 475                 480

Asp Cys Arg Leu Leu Gly Lys Phe Asp Leu Ser Gly Ile Pro Ala Ala
                485                 490                 495

Pro Arg Gly Thr Pro Gln Ile Glu Val Thr Phe Glu Val Asp Ala Asn
            500                 505                 510

Gly Ile Leu Asn Val Lys Ala Glu Asp Lys Gly Thr Gly Lys Ser Glu
        515                 520                 525

Lys Ile Thr Ile Thr Asn Glu Lys Gly Arg Leu Ser Gln Glu Glu Ile
    530                 535                 540

Asp Arg Met Val Arg Glu Ala Glu Glu Phe Ala Glu Glu Asp Lys Lys
545                 550                 555                 560

Val Lys Glu Arg Ile Asp Ala Arg Asn Gln Leu Glu Thr Tyr Val Tyr
                565                 570                 575
```

Asn Met Lys Asn Thr Val Gly Asp Lys Asp Lys Leu Ala Asp Lys Leu
            580                 585                 590

Glu Ser Glu Glu Lys Glu Lys Val Glu Glu Ala Leu Lys Glu Ala Leu
            595                 600                 605

Glu Trp Leu Asp Glu Asn Gln Thr Ala Glu Lys Glu Glu Tyr Glu Glu
            610                 615                 620

Lys Leu Lys Glu Val Glu Ala Val Cys Asn Pro Ile Ile Ser Ala Val
625                 630                 635                 640

Tyr Gln Arg Thr Gly Gly Ala Pro Gly Gly Arg Arg Gly Arg Leu
            645                 650                 655

Asp Asp Glu His Asp Glu Leu
            660

<210> SEQ ID NO 7
<211> LENGTH: 715
<212> TYPE: PRT
<213> ORGANISM: Oryza sativa

<400> SEQUENCE: 7

Met Ala Ser Phe Thr Ser Gln Leu Gly Ala Met Ala Cys Gly Ala Ala
1               5                   10                  15

Pro Ser Thr Ser Pro Leu Ala Ala Arg Arg Ser Gly Gln Leu Phe Val
            20                  25                  30

Gly Arg Lys Pro Ala Ala Ala Ser Val Gln Met Arg Val Pro Arg Ala
            35                  40                  45

Gly Arg Ala Arg Gly Val Ala Met Arg Val Ala Cys Glu Lys Val Val
        50                  55                  60

Gly Ile Asp Leu Gly Thr Thr Asn Ser Ala Val Ala Ala Met Glu Gly
65                  70                  75                  80

Gly Lys Pro Thr Val Ile Thr Asn Ala Glu Gly Gln Arg Thr Thr Pro
            85                  90                  95

Ser Val Val Ala Tyr Thr Lys Gly Gly Glu Arg Leu Val Gly Gln Ile
            100                 105                 110

Ala Lys Arg Gln Ala Val Val Asn Pro Glu Asn Thr Phe Phe Ser Val
        115                 120                 125

Lys Arg Phe Ile Gly Arg Lys Met Ala Glu Val Asp Asp Glu Ala Lys
130                 135                 140

Gln Val Ser Tyr His Val Arg Asp Asp Asn Gly Asn Val Lys Leu
145                 150                 155                 160

Asp Cys Pro Ala Ile Gly Lys Gln Phe Ala Ala Glu Glu Ile Ser Ala
            165                 170                 175

Gln Val Leu Arg Lys Leu Val Asp Asp Ala Ser Lys Phe Leu Asn Asp
            180                 185                 190

Lys Ile Thr Lys Ala Val Val Thr Val Pro Ala Tyr Phe Asn Asp Ser
            195                 200                 205

Gln Arg Thr Ala Thr Lys Asp Ala Gly Arg Ile Ala Gly Leu Glu Val
            210                 215                 220

Leu Arg Ile Ile Asn Glu Pro Thr Ala Ala Ser Leu Ala Tyr Gly Phe
225                 230                 235                 240

Glu Lys Lys Asn Asn Glu Thr Ile Leu Val Phe Asp Leu Gly Gly Gly
            245                 250                 255

Thr Phe Asp Val Ser Val Leu Glu Val Gly Asp Gly Val Phe Glu Val
            260                 265                 270

Leu Ser Thr Ser Gly Asp Thr His Leu Gly Gly Asp Asp Phe Asp Lys
            275                 280                 285

```
Phe Tyr Phe Cys Trp Val Phe Tyr Phe Gly Ala Met Thr His Glu Thr
    290                 295                 300

Pro Lys Val Val Asp Trp Leu Ala Ser Asn Phe Lys Lys Asp Glu Gly
305                 310                 315                 320

Ile Asp Leu Leu Lys Asp Lys Gln Ala Leu Gln Arg Leu Thr Glu Ala
                325                 330                 335

Ala Glu Lys Ala Lys Met Glu Leu Ser Thr Leu Ser Gln Thr Asn Ile
            340                 345                 350

Ser Leu Pro Phe Ile Thr Ala Thr Ala Asp Gly Pro Lys His Ile Glu
        355                 360                 365

Thr Thr Leu Ser Arg Ala Lys Phe Glu Glu Leu Cys Ser Asp Leu Ile
    370                 375                 380

Asp Arg Leu Lys Thr Pro Val Thr Asn Ala Leu Arg Asp Ala Lys Leu
385                 390                 395                 400

Ser Val Asp Asn Leu Asp Glu Val Ile Leu Val Gly Gly Ser Thr Arg
                405                 410                 415

Ile Pro Ser Val Gln Glu Leu Val Lys Lys Ile Thr Gly Lys Asp Pro
            420                 425                 430

Asn Val Thr Val Asn Pro Asp Glu Val Val Ser Leu Gly Ala Ala Val
        435                 440                 445

Gln Gly Gly Val Leu Ala Gly Asp Val Lys Asp Val Val Leu Leu Asp
    450                 455                 460

Val Thr Pro Leu Ser Leu Gly Leu Glu Thr Leu Gly Gly Val Met Thr
465                 470                 475                 480

Lys Ile Ile Pro Arg Asn Thr Thr Leu Pro Thr Ser Lys Ser Glu Val
                485                 490                 495

Phe Ser Thr Ala Ala Asp Gly Gln Thr Ser Val Glu Ile Asn Val Leu
            500                 505                 510

Gln Gly Glu Arg Glu Phe Val Arg Asp Asn Lys Ser Leu Gly Ser Phe
        515                 520                 525

Arg Leu Asp Gly Ile Pro Pro Ala Pro Arg Gly Val Pro Gln Ile Glu
    530                 535                 540

Val Lys Phe Asp Ile Asp Ala Asn Gly Ile Leu Ser Val Ala Ala Ile
545                 550                 555                 560

Asp Lys Gly Thr Gly Lys Lys Gln Asp Ile Thr Ile Thr Gly Ala Ser
                565                 570                 575

Thr Leu Pro Lys Asp Glu Val Glu Arg Met Val Glu Glu Ala Asp Lys
            580                 585                 590

Phe Ala Gln Glu Asp Lys Glu Lys Arg Asp Ala Ile Asp Thr Lys Asn
        595                 600                 605

Gln Ala Asp Ser Val Val Tyr Gln Thr Glu Lys Gln Leu Lys Glu Leu
    610                 615                 620

Gly Asp Lys Val Pro Ala Pro Val Lys Glu Lys Val Asp Ala Lys Leu
625                 630                 635                 640

Asn Glu Leu Lys Glu Ala Ile Ala Gly Gly Ser Thr Gln Ser Met Lys
                645                 650                 655

Asp Ala Met Ala Ala Leu Asn Glu Glu Val Met Gln Ile Gly Gln Ala
            660                 665                 670

Met Tyr Asn Gln Gln Pro Asn Ala Gly Ala Ala Gly Pro Thr Pro Gly
        675                 680                 685

Ala Asp Ala Gly Pro Thr Ser Ser Gly Gly Lys Gly Pro Asn Asp Gly
    690                 695                 700
```

Asp Val Ile Asp Ala Asp Phe Thr Asp Ser Asn
705              710              715

<210> SEQ ID NO 8
<211> LENGTH: 2079
<212> TYPE: DNA
<213> ORGANISM: Homo sapiens

<400> SEQUENCE: 8

| | | | | | |
|---|---|---|---|---|---|
| ggccgtagga | gaaggagtgt | tcagtggtgc | gccgtatccc | aacccgaggc | cacaaaatgc | 60 |
| ttccaatggc | aaaggaatat | gagaaaagtg | cgtggccctc | ctgtcagctg | cataaagaga | 120 |
| gactccccca | tccagtgtat | ccaggccatt | gcggaaaaca | gggccgatgc | tgtgaccctt | 180 |
| gatggtggtt | tcatatacga | ggcaggcctg | gcccctaca | aactgcgacc | tgtagcggcg | 240 |
| gaagtctacg | ggaccgaaag | acagccacga | actcactatt | atgccgtggc | tgtggtgaag | 300 |
| aagggcggca | gctttcagct | gaacgaactg | caaggtctga | agtcctgcca | cacaggcctt | 360 |
| cgcaggaccg | ctggatggaa | tgtccctata | gggacacttc | gtccattctt | gaattggacg | 420 |
| ggtccacctg | agcccattga | ggcagctgtg | gccaggttct | tctcagccag | ctgtgttccc | 480 |
| ggtgcagata | aggacagtt | ccccaacctg | tgtcgcctgt | gtgcggggac | aggggaaaac | 540 |
| aaatgtgcct | tctcctccca | ggaaccgtac | ttcagctact | ctggtgcctt | caagtgtctg | 600 |
| agagacgggg | ctggagacgt | ggcttttatc | agagagagca | cagtgtttga | ggacctgtca | 660 |
| gacgaggctg | aaagggacga | gtatgagtta | ctctgcccag | acaacactcg | gaagccagtg | 720 |
| gacaagttca | agactgcca | tctggcccgg | gtcccttctc | atgccgttgt | ggcacgaagt | 780 |
| gtgaatggca | aggaggatgc | catctggaat | cttctccgcc | aggcacagga | aaagtttgga | 840 |
| aaggacaagt | caccgaaatt | ccagctcttt | ggctccccta | gtgggcagaa | agatctgctg | 900 |
| ttcaaggact | ctgccattgg | gttttcgagg | gtgccccga | ggatagattc | tgggctgtac | 960 |
| cttggctccg | gctacttcac | tgccatccag | aacttgagga | aaagtgagga | ggaagtggct | 1020 |
| gcccggcgtg | cgcgggtcgt | gtggtgtgcg | gtgggcgagc | aggagctgcg | caagtgtaac | 1080 |
| cagtggagtg | gcttgagcga | aggcagcgtg | acctgctcct | cggcctccac | cacagaggac | 1140 |
| tgcatcgccc | tggtgctgaa | aggagaagct | gatgccatga | gtttggatgg | aggatatgtg | 1200 |
| tacactgcag | gcaaatgtgg | tttggtgcct | gtcctggcag | agaactacaa | atcccaacaa | 1260 |
| agcagtgacc | ctgatcctaa | ctgtgtggat | agacctgtgg | aaggatatct | tgctgtggcg | 1320 |
| gtggttagga | gatcagacac | tagccttacc | tggaactctg | tgaaaggcaa | gaagtcctgc | 1380 |
| cacaccgccg | tggacaggac | tgcaggctgg | aatatcccca | tgggcctgct | cttcaaccag | 1440 |
| acgggctcct | gcaaatttga | tgaatatttc | agtcaaagct | gtgcccctgg | gtctgacccg | 1500 |
| agatctaatc | tctgtgctct | gtgtattggc | gacgagcagg | gtgagaataa | gtgcgtgccc | 1560 |
| aacagcaacg | agagatacta | cggctacact | ggggctttcc | ggtgcctggc | tgagaatgct | 1620 |
| ggagacgttg | catttgtgaa | agatgtcact | gtcttgcaga | acactgatgg | aaataacaat | 1680 |
| gaggcatggg | ctaaggattt | gaagctggca | gactttgcgc | tgctgtgcct | cgatggcaaa | 1740 |
| cggaagcctg | tgactgaggc | tagaagctgc | catcttgcca | tggcccccgaa | tcatgccgtg | 1800 |
| gtgtctcgga | tggataaggt | ggaacgcctg | aaacaggtgt | tgctccacca | acaggctaaa | 1860 |
| tttgggagaa | atggatctga | ctgcccggac | aagttttgct | tattccagtc | tgaaaccaaa | 1920 |
| aaccttctgt | tcaatgacaa | cactgagtgt | ctggccagac | tccatggcaa | acaacatat | 1980 |
| gaaaaatatt | tgggaccaca | gtatgtcgca | ggcattacta | atctgaaaaa | gtgctcaacc | 2040 | tccccccctcc tggaagcctg tgaattcctc aggaagtaa         2079

<210> SEQ ID NO 9
<211> LENGTH: 2076
<212> TYPE: DNA
<213> ORGANISM: Artificial Sequence
<220> FEATURE:
<223> OTHER INFORMATION: Synthetic Sequence

<400> SEQUENCE: 9
gggcggcggc ggcgctcggt gcagtggtgc gccgtgtccc agcccgaggc gaccaagtgc    60
ttccagtggc agcgcaacat gcggaaggtg cgcggcccgc cggtcagctg catcaagcgg   120
gactccccca tccaatgcat ccaggccatc gcggagaacc gcgccgacgc ggtcaccctg   180
gacggcgggt tcatctacga ggcggggctc gccccgtaca agctccgccc ggtggcggcg   240
gaggtgtacg gcaccgagcg ccagccgcgc acgcactact acgcggtggc cgtcgtcaag   300
aagggcgggt ccttccagct caacgagctg cagggcctga gtcgtgcca cacgggcctc    360
cggcggacgg cgggctggaa cgtgcccatc ggcaccctgc ccccttcct gaactggacc    420
ggcccgccgg agccgatcga ggccgccgtg gcccgcttct tcagcgcctc ctgcgtcccc   480
ggcgccgaca agggccagtt cccgaacctc tgccggctct gcgccgggac gggcgagaac   540
aagtgcgcct tctcctcgca ggagccgtac ttctcctact cgggcgcgtt caagtgcctc    600
cgcgacgggg ccggcgacgt ggcgttcatc cgcgagtcca ccgtgttcga ggacctctcc    660
gacgaggcgg agcgggacga gtacgagctg ctgtgccccg acaacacccg caagccggtg    720
gacaagttca aggactgcca cctgcgcggg gtgcccctcgc acgcggtcgt cgcccgcagc   780
gtcaacggca aggaggacgc gatctggaac ctcctccgcc aggcccagga gaagttcggc    840
aaggacaagt cccccaagtt ccagctcttc gggagcccca gcggcagaa ggacctcctc    900
ttcaaggact ccgcgatcgg cttctcccgc gtccccccgc gcatcgactc cggcctgtac    960
ctcggctccg ggtacttcac cgcgatccag aacctccgga gagcgagga ggaggtggcg   1020
gcgcggcggg cccgcgtcgt gtggtgcgcc gtgggcgagc aggagctgcg gaagtgcaac   1080
cagtggagcg gcctgagcga ggggtcggtg acctgctcgt ccgccagcac caccgaggac   1140
tgcatcgcgc tcgtcctcaa gggggaggcc gacgcgatga gcctcgacgg ggggtacgtc   1200
tacaccgccg gcaagtgcgg cctggtcccg gtcctggcgg agaactacaa gtcgcagcag   1260
tccagcgacc ccgacccgaa ctgcgtggac cgccccgtcg agggctacct cgccgtggcc   1320
gtcgtgcgcc ggtccgacac ctccctgacg tggaacagcg tcaagggcaa gaagagctgc   1380
cacaccgccg tggaccgcac cgccggctgg aacatcccga tgggcctcct cttcaaccag   1440
accggctcct gcaagttcga cgagtacttc tcccagtcct gcgccccggg ctcggacccc   1500
cgctccaacc tgtgcgccct ctgcatcggg gacgagcagg gcgagaacaa gtgcgtgccc   1560
aacagcaacg agcggtacta cggctacacg ggggccttcc gctgcctggc ggagaacgcc   1620
ggggacgtcg cgttcgtgaa ggacgtgacc gtgctgcaaa acacggacgg gaacaacaac   1680
gaggcgtggg cgaaggacct caagctcgcc gacttcgccc tgctgtgcct cgacggcaag   1740
cgcaagcccg tcaccgaggc gcggtcctgc cacctggcga tggcccccaa ccacgccgtc   1800
gtctcccgca tggacaaggt cgagcgcctc aagcaggtgc tcctgcacca gcaggccaag   1860
ttcggccgga acggcagcga ctgcccggac aagttctgcc tgttccagtc ggagaccaag   1920
aacctcctct tcaacgacaa caccgagtgc ctggcgcgcc tccacggcaa gaccacctac   1980
gagaagtacc tcggcccgca gtacgtcgcc ggcatcacca acctcaagaa gtgctccacc   2040

```
tccccccctcc tggaggcgtg cgagttcctc cgcaag                                        2076
```

<210> SEQ ID NO 10
<211> LENGTH: 692
<212> TYPE: PRT
<213> ORGANISM: Homo sapiens

<400> SEQUENCE: 10

```
Gly Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Val Arg Gly
                20                  25                  30

Pro Pro Val Ser Cys Ile Lys Arg Asp Ser Pro Ile Gln Cys Ile Gln
                35                  40                  45

Ala Ile Ala Glu Asn Arg Ala Asp Ala Val Thr Leu Asp Gly Gly Phe
50                      55                      60

Ile Tyr Glu Ala Gly Leu Ala Pro Tyr Lys Leu Arg Pro Val Ala Ala
65                  70                      75                  80

Glu Val Tyr Gly Thr Glu Arg Gln Pro Arg Thr His Tyr Tyr Ala Val
                85                  90                  95

Ala Val Val Lys Lys Gly Ser Phe Gln Leu Asn Glu Leu Gln Gly
                100                 105                 110

Leu Lys Ser Cys His Thr Gly Leu Arg Arg Thr Ala Gly Trp Asn Val
            115                 120                 125

Pro Ile Gly Thr Leu Arg Pro Phe Leu Asn Trp Thr Gly Pro Pro Glu
            130                 135                 140

Pro Ile Glu Ala Ala Val Ala Arg Phe Phe Ser Ala Ser Cys Val Pro
145                 150                 155                 160

Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
                180                 185                 190

Tyr Ser Gly Ala Phe Lys Cys Leu Arg Asp Gly Ala Gly Asp Val Ala
                195                 200                 205

Phe Ile Arg Glu Ser Thr Val Phe Glu Asp Leu Ser Asp Glu Ala Glu
            210                 215                 220

Arg Asp Glu Tyr Glu Leu Leu Cys Pro Asp Asn Thr Arg Lys Pro Val
225                 230                 235                 240

Asp Lys Phe Lys Asp Cys His Leu Ala Arg Val Pro Ser His Ala Val
                245                 250                 255

Val Ala Arg Ser Val Asn Gly Lys Glu Asp Ala Ile Trp Asn Leu Leu
                260                 265                 270

Arg Gln Ala Gln Glu Lys Phe Gly Lys Asp Lys Ser Pro Lys Phe Gln
            275                 280                 285

Leu Phe Gly Ser Pro Ser Gly Gln Lys Asp Leu Leu Phe Lys Asp Ser
            290                 295                 300

Ala Ile Gly Phe Ser Arg Val Pro Pro Arg Ile Asp Ser Gly Leu Tyr
305                 310                 315                 320

Leu Gly Ser Gly Tyr Phe Thr Ala Ile Gln Asn Leu Arg Lys Ser Glu
                325                 330                 335

Glu Glu Val Ala Ala Arg Arg Ala Arg Val Val Trp Cys Ala Val Gly
                340                 345                 350

Glu Gln Glu Leu Arg Lys Cys Asn Gln Trp Ser Gly Leu Ser Glu Gly
            355                 360                 365
```

Ser Val Thr Cys Ser Ser Ala Ser Thr Thr Glu Asp Cys Ile Ala Leu
    370                 375                 380

Val Leu Lys Gly Glu Ala Asp Ala Met Ser Leu Asp Gly Gly Tyr Val
385                 390                 395                 400

Tyr Thr Ala Gly Lys Cys Gly Leu Val Pro Val Leu Ala Glu Asn Tyr
                405                 410                 415

Lys Ser Gln Gln Ser Ser Asp Pro Asp Pro Asn Cys Val Asp Arg Pro
                420                 425                 430

Val Glu Gly Tyr Leu Ala Val Ala Val Val Arg Arg Ser Asp Thr Ser
                435                 440                 445

Leu Thr Trp Asn Ser Val Lys Gly Lys Lys Ser Cys His Thr Ala Val
    450                 455                 460

Asp Arg Thr Ala Gly Trp Asn Ile Pro Met Gly Leu Leu Phe Asn Gln
465                 470                 475                 480

Thr Gly Ser Cys Lys Phe Asp Glu Tyr Phe Ser Gln Ser Cys Ala Pro
                485                 490                 495

Gly Ser Asp Pro Arg Ser Asn Leu Cys Ala Leu Cys Ile Gly Asp Glu
                500                 505                 510

Gln Gly Glu Asn Lys Cys Val Pro Asn Ser Asn Glu Arg Tyr Tyr Gly
    515                 520                 525

Tyr Thr Gly Ala Phe Arg Cys Leu Ala Glu Asn Ala Gly Asp Val Ala
    530                 535                 540

Phe Val Lys Asp Val Thr Val Leu Gln Asn Thr Asp Gly Asn Asn Asn
545                 550                 555                 560

Glu Ala Trp Ala Lys Asp Leu Lys Leu Ala Asp Phe Ala Leu Leu Cys
                565                 570                 575

Leu Asp Gly Lys Arg Lys Pro Val Thr Glu Ala Arg Ser Cys His Leu
                580                 585                 590

Ala Met Ala Pro Asn His Ala Val Val Ser Arg Met Asp Lys Val Glu
    595                 600                 605

Arg Leu Lys Gln Val Leu Leu His Gln Gln Ala Lys Phe Gly Arg Asn
    610                 615                 620

Gly Ser Asp Cys Pro Asp Lys Phe Cys Leu Phe Gln Ser Glu Thr Lys
625                 630                 635                 640

Asn Leu Leu Phe Asn Asp Asn Thr Glu Cys Leu Ala Arg Leu His Gly
                645                 650                 655

Lys Thr Thr Tyr Glu Lys Tyr Leu Gly Pro Gln Tyr Val Ala Gly Ile
                660                 665                 670

Thr Asn Leu Lys Lys Cys Ser Thr Ser Pro Leu Leu Glu Ala Cys Glu
    675                 680                 685

Phe Leu Arg Lys
    690

<210> SEQ ID NO 11
<211> LENGTH: 1830
<212> TYPE: DNA
<213> ORGANISM: Artificial Sequence
<220> FEATURE:
<223> OTHER INFORMATION: Synthetic Sequence

<400> SEQUENCE: 11
atggcatcca taaatcgccc catagttttc ttcacagttt gcttgttcct cttgtgcgat        60
ggctccctag ccgacgccca caagagcgag gtggcccacc gcttcaagga cctcggcgag       120
gagaacttca aggccctcgt gctcatcgcc ttcgcccagt acctccagca gtgcccgttc       180

```
gaggaccacg tgaagctcgt gaacgaggtg accgagttcg ccaagacctg cgtggccgac    240
gagagcgccg agaactgcga caagagcctc cacaccctct cggcgacaa gctctgcacc     300
gtggccaccc tccgcgagac ctacggcgag atggccgact gctgcgccaa gcaggagccg    360
gagcgcaaca gtgcttcct ccagcacaag acgacaacc cgaacctccc cgcgcctcgtg     420
cgcccggagg tggacgtgat gtgcaccgcc ttccacgaca acgaggagac cttcctcaag    480
aagtacctct acgagatcgc ccgccgccac ccgtacttct acgccccgga gctcctcttc    540
ttcgccaagc gctacaaggc cgccttcacc gagtgctgcc aggccgccga caaggccgcc    600
tgcctcctcc cgaagctcga cgagctccgc gacgagggca aggcctccag cgccaagcag    660
cgcctcaagt gcgccagcct ccagaagttc ggcgagcgcg ccttcaaggc ctgggccgtg    720
gcccgcctca gccagcgctt cccgaaggcc gagttcgccg aggtgtccaa gctcgtgacc    780
gacctcacca aggtgcacac cgagtgctgc cacggcgacc tcctggagtg cgccgacgac    840
cgcgccgacc tcgccaagta catctgcgag aaccaggaca gcatctccag caagctcaag    900
gagtgctgcg agaagccgct cctggagaag tcccactgca tcgccgaggt ggagaacgac    960
gagatgccgg ccgacctccc gtccctcgcc gccgacttcg tggagagcaa ggacgtgtgc    1020
aagaactacg ccgaggccaa ggacgtcttc ctcggcatgt tcctctacga gtacgcccgc    1080
cgccacccgg actactccgt ggtgctcctc ctccgcctcg ccaagaccta cgagaccacc    1140
ctggagaagt gctgcgccgc cgccgacccg cacgagtgct acgccaaggt gttcgacgag    1200
ttcaagccgc tcgtggagga ccgcagaac ctcatcaagc agaactgcga gctcttcgag     1260
cagctcggcg agtacaagtt ccagaacgcc ctcctcgtgc gctacaccaa gaaggtgccg    1320
caggtgtcca ccccgaccct cgtggaggtg tcccgcaacc tcggcaaggt gggcagcaag    1380
tgctgcaagc acccggaggc caagcgcatg ccgtgcgccg aggactacct ctccgtggtg    1440
ctcaaccagc tctgcgtgct ccacgagaag accccggtga cgaccgcgt gaccaagtgc    1500
tgcaccgaga gcctcgtgaa ccgccgcccg tgcttctccg ccctggaggt cgacgagacc    1560
tacgtcccga aggagttcaa cgccgagacc ttcaccttcc acgccgacat ctgcaccctc    1620
tccgagaagg agcgccagat caagaagcag accgccctcg tcgagctcgt gaagcacaag    1680
ccgaaggcca ccaaggagca gctcaaggcc gtgatggacg acttcgccgc cttcgtggag    1740
aagtgctgca aggccgacga caaggagacc tgcttcgccg aggagggcaa gaagctcgtg    1800
gccgccagcc aggccgccct cggcctctga                                     1830
```

<210> SEQ ID NO 12
<211> LENGTH: 585
<212> TYPE: PRT
<213> ORGANISM: Artificial Sequence
<220> FEATURE:
<223> OTHER INFORMATION: Synthetic Peptide Sequence

<400> SEQUENCE: 12

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60
```

-continued

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
```

-continued

```
                    485                 490                 495
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585
```